US012611454B2

(12) United States Patent
Lozano-Dubernard et al.

(10) Patent No.: US 12,611,454 B2
(45) Date of Patent: Apr. 28, 2026

(54) RECOMBINANT VACCINE AGAINST COVID-19 BASED ON A PARAMYXOVIRUS VIRAL VECTOR

(71) Applicants: LABORATORIO AVI-MEX, S.A. DE C.V., Mexico City (MX); ICAHN SCHOOL OF MEDICINE AT MOUNT SINAI, New York, NY (US)

(72) Inventors: Bernardo Lozano-Dubernard, Mexico City (MX); Ernesto Soto-Priante, Mexico City (MX); David Sarfati-Mizrahi, Estado de Mexico (MX); Felipa Castro-Peralta, Juriquilla (MX); Georgina Paz-De La Rosa, Santiago de Queretaro (MX); Peter Palese, New York, NY (US); Adolfo Garcia-Sastre, New York, NY (US); Florian Krammer, New York, NY (US); Weina Sun, New York, NY (US)

(73) Assignees: LABORATORIO AVI-MEX, S.A. DE C.V., Mexico D.F. (MX); ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 535 days.

(21) Appl. No.: 17/998,737

(22) PCT Filed: Feb. 22, 2021

(86) PCT No.: PCT/IB2021/051491
§ 371 (c)(1),
(2) Date: Nov. 14, 2022

(87) PCT Pub. No.: WO2021/229311
PCT Pub. Date: Nov. 18, 2021

(65) Prior Publication Data
US 2023/0226171 A1     Jul. 20, 2023

(30) Foreign Application Priority Data

May 13, 2020    (WO) .................. PCT/IB2020/054545

(51) Int. Cl.
| | |
|---|---|
| *A61K 39/215* | (2006.01) |
| *A61K 39/00* | (2006.01) |
| *A61P 31/14* | (2006.01) |
| *C12N 15/86* | (2006.01) |

(52) U.S. Cl.
CPC ........... *A61K 39/215* (2013.01); *A61P 31/14* (2018.01); *C12N 15/86* (2013.01); *A61K 2039/5252* (2013.01); *A61K 2039/53* (2013.01); *C12N 2760/18143* (2013.01); *C12N 2770/20034* (2013.01)

(58) Field of Classification Search
CPC .......... A61K 39/215; A61K 2039/5252; A61K 2039/53; A61K 2039/51; A61K 2039/543;

A61K 2039/575; A61K 39/12; A61P 31/14; C12N 15/86; C12N 2760/18143; C12N 2770/20034; C12N 2770/20022; C12N 2760/18162; Y02A 50/30; C07K 14/005
See application file for complete search history.

(56) References Cited

U.S. PATENT DOCUMENTS

| | | | |
|---|---|---|---|
| 5,057,540 | A | 10/1991 | Kensil et al. |
| 5,166,057 | A | 11/1992 | Palese et al. |
| 5,786,199 | A | 7/1998 | Palese |
| 5,820,871 | A | 10/1998 | Palese et al. |
| 5,840,520 | A | 11/1998 | Palese et al. |
| 5,854,037 | A | 12/1998 | Palese et al. |
| 6,001,634 | A | 12/1999 | Palese et al. |
| 6,033,886 | A | 3/2000 | Conzelmann |
| 6,146,642 | A | 11/2000 | Garcia-Sastre et al. |
| 6,451,323 | B1 | 9/2002 | Garcia-Sastre et al. |
| 6,544,785 | B1 | 4/2003 | Palese et al. |
| 6,649,372 | B1 | 11/2003 | Palese et al. |
| 6,719,979 | B2 | 4/2004 | Peeters et al. |
| 6,887,699 | B1 | 5/2005 | Palese et al. |
| 7,244,558 | B1 | 7/2007 | Samal et al. |
| 7,332,169 | B2 | 2/2008 | Peeters et al. |
| 7,384,774 | B2 | 6/2008 | Palese et al. |
| 7,442,379 | B2 | 10/2008 | Garcia-sastre et al. |

(Continued)

FOREIGN PATENT DOCUMENTS

| | | |
|---|---|---|
| AU | 2002307971 B2 | 5/2008 |
| CA | 2118234 A1 | 10/1993 |

(Continued)

OTHER PUBLICATIONS

Amanat F, Stadlbauer D, Strohmeier S, Nguyen THO, Chromikova V, McMahon M, Jiang K, Asthagiri Arunkumar G, Jurczyszak D, et al. A serological assay to detect SARS-CoV-2 seroconversion in humans. medRxiv [Preprint]. Apr. 16, 2020: 2020.03.17.20037713. Update in: Nat Med. Jul. 2020;26(7):1033-1036. (Year: 2020).*

(Continued)

*Primary Examiner* — Rachel B Gill
(74) *Attorney, Agent, or Firm* — Bryan D. Zerhusen, Esq.; Nicholas R. Herrel, Esq.; CANTOR COLBURN LLP

(57) ABSTRACT

An active or inactivated recombinant vaccine against COVID-19 is described that comprises a Newcastle disease viral vector and a pharmaceutically acceptable carrier, adjuvant and/or excipient, characterized in that the viral vector is a virus capable of generating a cellular immune response that has a SARS-COV-2 exogenous nucleotide sequence inserted.

36 Claims, No Drawings
Specification includes a Sequence Listing.

(56)  References Cited

U.S. PATENT DOCUMENTS

| | | | |
|---|---|---|---|
| 7,547,442 | B2 | 6/2009 | Peeters et al. |
| 8,326,547 | B2 | 12/2012 | Liu et al. |
| 8,591,881 | B2 | 11/2013 | Palese et al. |
| 8,946,421 | B2 | 2/2015 | Johnson |
| 9,217,136 | B2 | 12/2015 | Palese et al. |
| 9,387,240 | B2 | 7/2016 | Palese et al. |
| 9,387,242 | B2 | 7/2016 | Palese et al. |
| 9,476,033 | B2 | 10/2016 | Samal et al. |
| 9,884,895 | B2 | 2/2018 | Baric et al. |
| 10,308,913 | B2 | 6/2019 | Palese et al. |
| 10,689,716 | B1 | 6/2020 | Daunert et al. |
| 11,510,977 | B2 | 11/2022 | Garcia-sastre et al. |
| 2003/0078410 | A1 | 4/2003 | Garcia-sastre et al. |
| 2003/0087417 | A1 | 5/2003 | Peeters et al. |
| 2003/0224017 | A1 | 12/2003 | Samal et al. |
| 2004/0142003 | A1 | 7/2004 | Palese et al. |
| 2004/0234552 | A1 | 11/2004 | Peeters et al. |
| 2005/0112554 | A1 | 5/2005 | Zhao et al. |
| 2005/0221489 | A1 | 10/2005 | Garcia-Sastre et al. |
| 2006/0057161 | A1 | 3/2006 | Huang et al. |
| 2006/0188519 | A1 | 8/2006 | Cheung et al. |
| 2007/0092938 | A1 | 4/2007 | Kwang et al. |
| 2008/0206201 | A1 | 8/2008 | Beier et al. |
| 2009/0061521 | A1 | 3/2009 | Palese et al. |
| 2009/0280144 | A1 | 11/2009 | Garcia-sastre et al. |
| 2010/0189745 | A1 | 7/2010 | Kistner et al. |
| 2011/0020282 | A1 | 1/2011 | Beier et al. |
| 2011/0311578 | A1 | 12/2011 | Lozano-Dubernard et al. |
| 2012/0058141 | A1 | 3/2012 | Palese et al. |
| 2012/0058538 | A1 | 3/2012 | Palese et al. |
| 2012/0064112 | A1 | 3/2012 | Samal et al. |
| 2012/0122185 | A1 | 5/2012 | Palese et al. |
| 2014/0044678 | A1 | 2/2014 | Palese et al. |
| 2014/0186303 | A1 | 7/2014 | Subbiah et al. |
| 2014/0271677 | A1 | 9/2014 | Palese et al. |
| 2015/0133531 | A1 | 5/2015 | Wiegand |
| 2016/0015760 | A1 | 1/2016 | Palese et al. |
| 2016/0068823 | A1 | 3/2016 | Palese et al. |
| 2017/0037379 | A1 | 2/2017 | Palese et al. |
| 2018/0078592 | A1 | 3/2018 | Palese et al. |
| 2018/0110874 | A1 | 4/2018 | Li |
| 2018/0256655 | A1 | 9/2018 | Palese et al. |
| 2018/0280455 | A1 | 10/2018 | Palese et al. |
| 2019/0351044 | A1 | 11/2019 | Jasny et al. |
| 2020/0040042 | A1 | 2/2020 | Chappell et al. |
| 2020/0061184 | A1 | 2/2020 | Palese et al. |
| 2020/0297787 | A1 | 9/2020 | Garcia-Sastre et al. |
| 2021/0198323 | A1 | 7/2021 | Durbin et al. |
| 2021/0260178 | A1 | 8/2021 | Jasny et al. |
| 2021/0379181 | A1 | 12/2021 | Rauch et al. |
| 2022/0040292 | A1 | 2/2022 | Tang et al. |
| 2022/0241358 | A1 | 8/2022 | Garcia-Sastre et al. |
| 2023/0220052 | A1 | 7/2023 | Cheng et al. |
| 2024/0210415 | A1* | 6/2024 | Krammer ......... G01N 33/54366 |

FOREIGN PATENT DOCUMENTS

| | | | | | |
|---|---|---|---|---|---|
| CN | 1177224 | C | 11/2004 | | |
| CN | 1184319 | C | 1/2005 | | |
| CN | 1216902 | C | 8/2005 | | |
| CN | 1806175 | C | 7/2006 | | |
| CN | 100467484 | C | 3/2009 | | |
| CN | 101522208 | A | 9/2009 | | |
| CN | 111187354 | A | 5/2020 | | |
| CN | 111208298 | A | 5/2020 | | |
| CN | 111233985 | A | 6/2020 | | |
| CN | 111239391 | A | 6/2020 | | |
| CN | 111273001 | A | 6/2020 | | |
| CN | 210894377 | U | 6/2020 | | |
| CN | 210894378 | U | 6/2020 | | |
| CN | 111366734 | A | 7/2020 | | |
| CN | 111366735 | A | 7/2020 | | |
| CN | 111413500 | A | 7/2020 | | |
| CN | 111426839 | A | 7/2020 | | |
| CN | 111505310 | A | 8/2020 | | |
| CN | 111521818 | A | 8/2020 | | |
| CN | 111562365 | A | 8/2020 | | |
| CN | 111610327 | A | 9/2020 | | |
| CN | 111690060 | A | 9/2020 | | |
| CN | 111707834 | A | 9/2020 | | |
| CN | 111856003 | A | 10/2020 | | |
| CN | 111879951 | A | 11/2020 | | |
| CN | 211905393 | U | 11/2020 | | |
| CN | 112011521 | A | 12/2020 | | |
| CN | 112098645 | A | 12/2020 | | |
| CN | 112114140 | A | 12/2020 | | |
| CN | 112114141 | A | 12/2020 | | |
| EP | 0702085 | A1 | 3/1996 | | |
| EP | 0780475 | A1 | 6/1997 | | |
| EP | 0780475 | B1 | 6/1997 | | |
| EP | 0974660 | A1 | 1/2000 | | |
| EP | 2085092 | A1 | 8/2009 | | |
| EP | 2251034 | A1 | 11/2010 | | |
| EP | 2393921 | B1 | 7/2015 | | |
| EP | 2987856 | A1 | 2/2016 | | |
| GB | 2220211 | A | 1/1990 | | |
| WO | 1996010632 | A1 | 4/1996 | | |
| WO | 1996034625 | A1 | 11/1996 | | |
| WO | 1997006270 | A1 | 2/1997 | | |
| WO | 1997012032 | A1 | 4/1997 | | |
| WO | 1998002530 | A1 | 1/1998 | | |
| WO | 1998013501 | A2 | 4/1998 | | |
| WO | 1998053078 | A1 | 11/1998 | | |
| WO | 1999002657 | A1 | 1/1999 | | |
| WO | 1999015672 | A1 | 4/1999 | | |
| WO | 1999018799 | A1 | 4/1999 | | |
| WO | 1999066045 | A1 | 12/1999 | | |
| WO | 2000015853 | A2 | 10/2000 | | |
| WO | 2000062735 | A2 | 10/2000 | | |
| WO | 2000067786 | A1 | 11/2000 | | |
| WO | 2001004333 | A1 | 1/2001 | | |
| WO | 2001020989 | A1 | 3/2001 | | |
| WO | 2002036617 | A2 | 5/2002 | | |
| WO | 2002081621 | A2 | 10/2002 | | |
| WO | 2003072725 | A2 | 9/2003 | | |
| WO | 2004109289 | A1 | 12/2004 | | |
| WO | 2005118813 | A2 | 12/2005 | | |
| WO | 2006050984 | A2 | 5/2006 | | |
| WO | 2006086561 | A2 | 8/2006 | | |
| WO | 2007064802 | A1 | 6/2007 | | |
| WO | 2007109812 | A2 | 9/2007 | | |
| WO | 2007109813 | A1 | 9/2007 | | |
| WO | 2009095167 | A1 | 8/2009 | | |
| WO | 2010058236 | A1 | 5/2010 | | |
| WO | 2010091262 | A1 | 8/2010 | | |
| WO | 2011059334 | A1 | 5/2011 | | |
| WO | 2013112942 | A1 | 8/2013 | | |
| WO | 2013166110 | A1 | 11/2013 | | |
| WO | 2013178344 | A1 | 12/2013 | | |
| WO | 2014158811 | A1 | 10/2014 | | |
| WO | 2015032755 | A1 | 3/2015 | | |
| WO | 2016205347 | A1 | 12/2016 | | |
| WO | WO-2018209194 | A2 * | 11/2018 | .............. | A61P 35/00 |
| WO | 2020014591 | A1 | 1/2020 | | |
| WO | 2020037215 | A1 | 2/2020 | | |
| WO | 2021163365 | A1 | 8/2021 | | |
| WO | 2021174121 | A1 | 9/2021 | | |
| WO | 2021194826 | A2 | 9/2021 | | |
| WO | 2021226348 | A2 | 11/2021 | | |
| WO | 2021229270 | A1 | 11/2021 | | |
| WO | 2021243122 | A2 | 12/2021 | | |
| WO | 2021253962 | A1 | 12/2021 | | |
| WO | 2022076723 | A1 | 4/2022 | | |
| WO | 2022101307 | A1 | 5/2022 | | |
| WO | 2022232052 | A1 | 11/2022 | | |
| WO | 2023042181 | A1 | 3/2023 | | |
| WO | 2023056351 | A2 | 4/2023 | | |
| WO | 2023173032 | A2 | 9/2023 | | |

(56) References Cited

FOREIGN PATENT DOCUMENTS

WO      2023196759 A2    10/2023
WO      2023196945 A2    10/2023

OTHER PUBLICATIONS

Samal S, Kumar S, Khattar SK, Samal SK. A single amino acid change, Q114R, in the cleavage-site sequence of Newcastle disease virus fusion protein attenuates viral replication and pathogenicity. J Gen Virol. Oct. 2011;92(Pt 10):2333-2338. Epub Jun. 15, 2011. (Year: 2011).*

Rangaswamy US, Wang W, Cheng X, McTamney P, Carroll D, Jin H. Newcastle Disease Virus Establishes Persistent Infection in Tumor Cells In Vitro: Contribution of the Cleavage Site of Fusion Protein and Second Sialic Acid Binding Site of Hemagglutinin-Neuraminidase. J Virol. Jul. 27, 2017;91(16):e00770-17. (Year: 2017).*

Wu F, et. al. RecName: Full=Spike glycoprotein; Short=S glycoprotein; AltName: Full=E2; AltName: Full=Peplomer protein; Contains: RecName: Full=Spike protein S1; Contains: RecName: Full=Spike protein S2; Contains: RecName: Full=Spike protein S2'; etc. GenBank: PODTC2.1. 1stDep. Apr. 29, 2020. (Year: 2020).*

Lamers S, Feehan A, Nolan D, Rose R, Cross S, Moraga Amador D, Garcia-Daiz J, Yang T, Caruso L, Navia W, Von Borstel L, Hui Zhou, X. ORF1ab polyprotein, partial [Severe acute respiratory syndrome coronavirus 2]. GenBank: QJQ84242.1. Dep May 8, 2020. (Year: 2020).*

Roychoudhury P, Greninger,A, Jerome K. Surface glycoprotein [Severe acute respiratory syndrome coronavirus 2]. GenBank: QIS30635.1. Dep. Mar. 30, 2020. (Year: 2020).*

Genbank Accession No. MT081068.1, "Severe acute respiratory syndrome coronavirus 2 isolate SARS-CoV-2/ human/CHN/HS_194/2020 nucleocapsid phosphoprotein (N) gene, complete cds," Apr. 6, 2020 (2 pages).

Genbank Accession No. MT334558.1, "Severe acute respiratory syndrome coronavirus 2 isolate SARS-CoV-2/ human/USA/UT-00291/2020 ORF1ab polyprotein (ORF1ab), ORF1a polyprotein (ORF1ab), surface glycoprotein (S), ORF3a protein (ORF3a), envelope protein (E), membrane glycoprotein (M), and ORF6 protein (ORF6) genes, complete cds; ORF7a protein (ORF7a) and ORF7b (ORF7b) genes, partial cds; and ORF8 protein (ORF8), nucleocapsid phosphoprotein (N), and ORF10 protein (ORF10) genes, complete cds ," Apr. 14, 2020 (18 pages).

GenBank Accession No. MT380725.1, "Synthetic construct SARS_CoV_2_ectoCSPP gene, complete cds," Apr. 27, 2020 [online]. [Retrieved on Oct. 4, 2021]. Retrieved from the Internet: <URL: https://www.ncbi.nlm.nih.gov/ nuccore/MT380725> (2 pages).

Genbank Accession No. MT444529.1, "Severe acute respiratory syndrome coronavirus 2 isolate SARS-CoV-2/ human/USA/UT-00085/2020 ORF1ab polyprotein (ORF1ab), ORF1a polyprotein (ORF1ab), surface glycoprotein (S), ORF3a protein (ORF3a), envelope protein (E), membrane glycoprotein (M), and ORF6 protein (ORF6) genes, complete cds; ORF7a protein (ORF7a) and ORF7b (ORF7b) genes, partial cds; and ORF8 protein (ORF8), nucleocapsid phosphoprotein (N), and ORF10 protein (ORF10) genes, complete cds," May 8, 2020 (18 pages).

Genbank Accession No. MT444593.1, "Severe acute respiratory syndrome coronavirus 2 isolate SARS-CoV-2/ human/USA/UT-00884/2020 ORF1ab polyprotein (ORF1ab), ORF1a polyprotein (ORF1ab), surface glycoprotein (S), ORF3a protein (ORF3a), envelope protein (E), membrane glycoprotein (M), ORF6 protein (ORF6), ORF7a protein (ORF7a), ORF7b (ORF7b), ORF8 protein (ORF8), nucleocapsid phosphoprotein (N), and ORF10 protein (ORF10) genes, complete cds," May 8, 2020 (18 pages).

Genbank Accession No. MT446360.1, "Severe acute respiratory syndrome coronavirus 2 isolate SARS-CoV-2/ human/USA/LA-BIE-093/2020 ORF1ab polyprotein (ORF1ab) and ORF1a polyprotein (ORF1ab) genes, partial cds; and surface glycoprotein (S), ORF3a protein (ORF3a), envelope protein (E), membrane glycoprotein (M), ORF6 protein (ORF6), ORF7a protein (ORF7a), ORF7b (ORF7b), ORF8 protein (ORF8), nucleocapsid phosphoprotein (N), and ORF10 protein (ORF10) genes, complete cds," May 8, 2020 (18 pages).

Genbank Accession No. MT447160.1, "Severe acute respiratory syndrome coronavirus 2 isolate SARS-CoV-2/ human/THA/SI200615-NT/2020 ORF1ab polyprotein (ORF1ab), ORF1a polyprotein (ORF1ab), surface glycoprotein (S), ORF3a protein (ORF3a), envelope protein (E), membrane glycoprotein (M), ORF6 protein (ORF6), ORF7a protein (ORF7a), ORF7b (ORF7b), ORF8 protein (ORF8), nucleocapsid phosphoprotein (N), and ORF10 protein (ORF10) genes, complete cds," May 8, 2020 (10 pages).

Genbank Accession No. NC_002617.1, "Newcastle disease virus B1, complete genome," Nov. 30, 2009.

Genbank Accession No. NC_034968.1, "Avian paramyxovirus 15 isolate APMV-15/calidris_fuscicollis/Brazil/RS-1177/2012, partial genome," Aug. 13, 2018 (9 pages).

Genbank Accession No. U25837.1, "Newcastle disease virus isolate Ulster matrix protein mRNA, complete cds," Jul. 12, 1996.

Goff et al., "A Majority of Infectious Newcastle Disease Virus Particles Contain a Single Genome, while a Minority Contain Multiple Genomes," J. Virol., 86(19):10852-10856 (2012).

Goff et al., "A Majority of Infectious Newcastle Disease Virus Particles Contain a Single Genome, while a Minority Contain Multiple Genomes," J. Virol., 86(19):10852-10856 (2012). Gogoi et al., 2017, "Avian Paramyxovirus: A Brief Review," Transbound. Emerg. Dis., 64(1):53-67 (Epub 2015).

Goldberg et al., 2021, "Waning immunity of the BNT162b2 vaccine: A nationwide study from Israel," medRxiv, /2021.08.24. 21262423 (21 pages).

Gonzalez-Dominguez et al., 2022, "Trivalent NDV-HXP-S vaccine protects against phylogenetically distant SARS-CoV-2 variants of concern in mice," bioRxiv, 2022.03.21.485247 (24 pages).

Gonzalez-Dominguez et al., 2022, "Trivalent NDV-HXP-S Vaccine Protects against Phylogenetically Distant SARS-CoV-2 Variants of Concern in Mice," Microbiol. Spectr., 10(3):e0153822 (14 pages).

Gonzalez-Reiche et al., 2020, "Introductions and early spread of SARS-CoV-2 in the New York City area," Science, 369(6501):297-301.

Gorbalenya et al., 2020, "The species Severe acute respiratory syndrome-related coronavirus: classifying 2019-nCoV and naming it SARS-CoV-2," Nat. Microbiol., 5(4):536-544.

Grifoni et al., 2020, "A Sequence Homology and Bioinformatic Approach Can Predict Candidate Targets for Immune Responses to SARS-CoV-2," Cell Host Microbe., 27(4):671-680.e2.

Gunn et al., 2018, "A Role for Fc Function in Therapeutic Monoclonal Antibody-Mediated Protection against Ebola Virus," Cell Host Microbe., 24(2):221-233.e5.

Hadfield et al., 2018, "Nextstrain: real-time tracking of pathogen evolution," Bioinformatics, 34(23):4121-4123.

Hains et al., 2020, "Asymptomatic Seroconversion of Immunoglobulins to SARS-CoV-2 in a Pediatric Dialysis Unit," JAMA, 323(23):2424-2425.

Haveri et al., 2020, "Serological and molecular findings during SARS-CoV-2 infection: the first case study in Finland, Jan. to Feb. 2020," Euro. Surveill., 25(11):2000266 (6 pages).

He et al., 2014, "Recent development of poly(ethylene glycol)-cholesterol conjugates as drug delivery systems," Int. J. Pharm., 469(1):168-178.

Hemmi et al., 2002, "Small anti-viral compounds activate immune cells via the TLR7 MyD88-dependent signaling pathway," Nat. Immunol., 3(2):196-200.

Herck et al., 2001, "Inactivated hepatitis A vaccine-induced antibodies: follow-up and estimates of long-term persistence," J. Med. Virol., 63(1):1-7.

Hoffmann et al., 2020, "The novel coronavirus 2019 (2019-nCoV) uses the SARS-coronavirus receptor ACE2 and the cellular protease TMPRSS2 for entry into target cells," bioRxiv, 2020.01.31.929042 (23 pages).

Hofmeyer et al., "The PD-1/PD-L1 (B7-H1) Pathway in Chronic Infection-Induced Cytotoxic T Lymphocyte Exhaustion," J. Biomed. Biotechnol., 2011:451694 (2011).

(56) References Cited

OTHER PUBLICATIONS

Holder, 2023, "Tracking Coronavirus Vaccinations Around the World," The New York Times, Mar. 13, 2023 [online]. [Retrieved on Oct. 8, 2023]. Retrieved from the Internet: <URL: https://www.nytimes.com/interactive/2021/world/covid-vaccinations-tracker.html> (9 pages).

Hsieh et al., 2020, "Structure-based Design of Prefusion-stabilized SARS-CoV-2 Spikes," bioRxiv, 2020.05.30.125484 (39 pages).

Hsieh et al., 2020, "Structure-based design of prefusion-stabilized SARS-CoV-2 spikes," Science, 369(6510):1501-1505 and Supplementary Materials (9 pages).

Hu et al., 2007, "Intranasal Protollin-formulated recombinant SARS S-protein elicits respiratory and serum neutralizing antibodies and protection in mice," Vaccine, 25(34):6334-6340.

Huang et al., "Newcastle disease virus V protein is associated with viral pathogenesis and functions as an alpha interferon antagonist," J. Virol., 77:8676-8685 (2003).

Huang et al., 2004, "The hemagglutinin-neuraminidase protein of Newcastle disease virus determines tropism and virulence," J Virol., 78(8):4176-4184.

Huang et al., 2020, "A systematic review of antibody mediated immunity to coronaviruses: antibody kinetics, correlates of protection, and association of antibody responses with severity of disease," medRxiv, 2020.04.14.20065771 (47 pages).

Huang et al., 2020, "A systematic review of antibody mediated immunity to coronaviruses: kinetics, correlates of protection, and association with severity," Nat. Commun., 11(1):4704 (16 pages).

Huang et al., 2020, "Fast assessment of human receptor-binding capability of 2019 novel coronavirus (2019-nCoV)," bioRxiv, 2020.02.01.930537 (14 pages).

Icahn School of Medicine At Mount Sinai, 2022, "Press Release—Mount Sinai Launches Phase 1 U.S. Trial of NDV-HXP-S, an Egg-Based Investigational COVID-19 Vaccine, in Healthy Adults Previously Immunized Against COVID-19," Mar. 21, 2022 (5 pages).

Ikegame et al., 2021, "Fitness selection of hyperfusogenic measles virus F proteins associated with neuropathogenic phenotypes," Proc. Natl. Acad. Sci. USA, 118(18):e2026027118 (12 pages).

Imai et al., 2020, "Syrian hamsters as a small animal model for SARS-CoV-2 infection and countermeasure development," Proc. Natl. Acad. Sci. USA, 117(28):16587-16595.

International Searching Authority, English Translation of International Search Report and Written Opinion for International Patent Application No. PCT/IB2020/054545 (Pub No. WO 2021229270) mailed Dec. 7, 2020 (15 pages).

International Searching Authority, English Translation of International Search Report and Written Opinion for International Patent Application No. PCT/IB2021/051491 (Pub No. WO 2021229311) mailed Jun. 4, 2021 (21 pages).

International Searching Authority, International Search Report and Written Opinion for International Patent Application No. PCT/IB2022/058886 (Pub No. WO 2023042181) mailed Feb. 9, 2023 (11 pages).

International Searching Authority, International Search Report and Written Opinion for International Patent Application No. PCT/US2021/022848 (Pub No. WO 2021194826) mailed Sep. 24, 2021 (26 pages).

International Searching Authority, International Search Report and Written Opinion for International Patent Application No. PCT/US2021/031110 (Pub No. WO 2021226348) mailed Oct. 29, 2021 (13 pages).

International Searching Authority, International Search Report and Written Opinion for International Patent Application No. PCT/US2021/054024 (Pub No. WO 2022076723) mailed Feb. 11, 2022 (7 pages).

International Searching Authority, International Search Report and Written Opinion for International Patent Application No. PCT/US2022/026185 (Pub No. WO 2022232052) mailed Feb. 9, 2023 (11 pages).

International Searching Authority, International Search Report and Written Opinion for International Patent Application No. PCT/US2022/077254 (Pub No. WO 2023056351) mailed Mar. 14, 2023 (18 pages).

International Searching Authority, International Search Report and Written Opinion for International Patent Application No. PCT/US2023/064063 (Pub No. WO 2023173032) mailed Aug. 4, 2023 (16 pages).

International Searching Authority, International Search Report and Written Opinion for International Patent Application No. PCT/US2023/065225 (Pub No. WO 2023196759) mailed Sep. 14, 2023 (12 pages).

Ahmed et al., 2020, "Preliminary identification of potential vaccine targets for the COVID-19 coronavirus (SARS-CoV-2) based on SARS-CoV immunological studies," bioRxiv, 2020.02.03.933226 (20 pages).

Ahmed et al., 2020, "Preliminary Identification of Potential Vaccine Targets for the COVID-19 Coronavirus (SARS-CoV-2) Based on SARS-CoV Immunological Studies," Viruses, 12(3):254 (15 pages).

Alexander et al., 1995, "The epidemiology and control of avian influenza and Newcastle disease," Journal of Comparative Pathology, 112:105-126.

Alexander, 1988, "Newcastle disease, Newcastle disease virus—an avian paramyxovirus," Kluwer Academic Publishers, Dordrecht, The Netherlands, pp. 1-22.

Alexander, 2000, "Newcastle disease and other avian paramyxoviruses," Rev. Sci. Tech., 19(2):443-462.

Amanat et al., 2018, "Antibodies to the Glycoprotein GP2 Subunit Cross-React between Old and New World Arenaviruses," mSphere, 3(3):e00189-18 (14 pages).

Amanat et al., 2019, "Cross-reactive antibodies binding to H4 hemagglutinin protect against a lethal H4N6 influenza virus challenge in the mouse model," Emerg. Microbes. Infect., 8(1):155-168.

Amanat et al., 2020, "A serological assay to detect SARS-CoV-2 seroconversion in humans," medRxiv, 2020.03.17.20037713 (18 pages).

Amanat et al., 2020, "A serological assay to detect SARS-CoV-2 seroconversion in humans," Nat. Med., 26(7):1033-1036 and Supplementary Materials (12 pages).

Amanat et al., 2020, "An In Vitro Microneutralization Assay for SARS-CoV-2 Serology and Drug Screening," Curr. Protoc. Microbiol., 58(1):e108 (15 pages).

Amanat et al., 2020, "Introduction of two prolines and removal of the polybasic cleavage site leads to optimal efficacy of a recombinant spike based SARS-CoV-2 vaccine in the mouse model," bioRxiv, 2020.09.16.300970 (15 pages).

Amanat et al., 2020, "SARS-CoV-2 Vaccines: Status Report," Immunity, 52(4):583-589.

AnyGo, 2020, "Beijing Anygo Provides Free COVID-19 Full-length S1-Fc Fusion Protein and New Corona Virus Total Antibody Test Kits," Feb. 18, 2020, in Chinese with machine English translation (6 pages).

Asogun et al., 2019, "Lassa Fever: Epidemiology, Clinical Features, Diagnosis, Management and Prevention," Infect. Dis. Clin. North Am., 33(4):933-951.

Ayllon et al., 2013, "Rescue of Recombinant Newcastle Disease Virus from cDNA," J. Vis. Exp., (80):e50830.

Bao et al., 2020, "Reinfection could not occur in SARS-CoV-2 infected rhesus macaques," bioRxiv., 2020.03.13.990226 (20 pages).

Barber et al. "Restoring function in exhausted CD8 T cells during chronic viral infection," Nature 439:682-687, with Supplemental Material attached (2006).

Benton et al., 2020, "Receptor binding and priming of the spike protein of SARS-CoV-2 for membrane fusion," Nature, 588(7837):327-330.

Berry et al., 2010, "Neutralizing epitopes of the SARS-CoV S-protein cluster independent of repertoire, antigen structure or mAb technology," MAbs, 2(1):53-66.

Bio-Rad Laboratories, Monolisa™ Anti-HBs EIA 25220; Monolisa™ Anti-HBs Calibrator Kit 25219, Biorad, Aug. 2006, pp. 1-28 [onlines]. [Retrieved on May 13, 2021]. Retrieved from the internet: <URL: https://www.accessdata.fda.gov/cdrh_docs/pdf5/P050048c.pdf> (28 pages).

(56)        References Cited

OTHER PUBLICATIONS

Bisht et al., 2004, "Severe acute respiratory syndrome coronavirus spike protein expressed by attenuated vaccinia virus protectively immunizes mice," Proc. Natl. Acad. Sci. USA, 101(17):6641-6646.

Bukreyev et al., 2005, "Recombinant newcastle disease virus expressing a foreign viral antigen is attenuated and highly immunogenic in primates," J. Virol., 79(21):13275-13284.

Calain et al., "The Rule of Six, a Basic Feature for Efficient Replication of Sendai Virus Defective Interfering RNA," J. Virol., 67(8):4822-4830 (1993).

Callaway, 2020, "The race for coronavirus vaccines: a graphical guide," Nature, 580(7805):576-577.

Callow et al., 1990, "The time course of the immune response to experimental coronavirus infection of man," Epidemiol. Infect., 105(2):435-446.

Carreno et al., 2021, "Evidence for retained spike-binding and neutralizing activity against emerging SARS-CoV-2 variants in serum of COVID-19 mRNA vaccine recipients," EBioMedicine, 73:103626 (9 pages).

Carreno et al., 2022, "Activity of convalescent and vaccine serum against SARS-CoV-2 Omicron," Nature, 602(7898):682-688 and Supplementary Materials (17 pages).

Carreno et al., 2022, "The inactivated NDV-HXP-S COVID-19 vaccine induces a significantly higher ratio of neutralizing to non-neutralizing antibodies in humans as compared to mRNA vaccines," medRxiv, 2022.01.25.22269808 (17 pages).

Carreno et al., 2023, "An inactivated NDV-HXP-S COVID-19 vaccine elicits a higher proportion of neutralizing antibodies in humans than mRNA vaccination," Science Translational Medicine, 15(683):eabo2847 (11 pages).

Casadevall et al., 2020, "The convalescent sera option for containing COVID-19," J. Clin. Invest., 130(4):1545-1548.

Chan et al., 2020, "Simulation of the Clinical and Pathological Manifestations of Coronavirus Disease 2019 (COVID-19) in a Golden Syrian Hamster Model: Implications for Disease Pathogenesis and Transmissibility," Clin. Infect. Dis., 71(9):2428-2446.

Chandrashekar et al., 2020, "SARS-CoV-2 infection protects against rechallenge in rhesus macaques," Science, 369(6505):812-817.

Chen et al., 2020, "Structure analysis of the receptor binding of 2019-nCoV," Biochem. Biophys. Res. Commun., 525(1):135-140.

Choe et al., 2017, "MERS-CoV Antibody Responses 1 Year after Symptom Onset, South Korea, 2015," Emerg. Infect. Dis., 23(7):1079-1084.

Choi et al., 2020, "Non-sterilizing, Infection-Permissive Vaccination With Inactivated Influenza Virus Vaccine Reshapes Subsequent Virus Infection-Induced Protective Heterosubtypic Immunity From Cellular to Humoral Cross-Reactive Immune Responses," Front Immunol., 11:1166 (18 pages).

Chromikova et al., 2017, "Generation of a serum free CHO DG44 cell line stably producing a broadly protective anti-influenza virus monoclonal antibody," PLoS One, 12(9):e0183315 (11 pages).

Chu et al., 2020, "Molecular Diagnosis of a Novel Coronavirus (2019-nCoV) Causing an Outbreak of Pneumonia," Clin. Chem., 66(4):549-555.

Chumbe et al., 2017, "Development of a novel Newcastle disease virus (NDV) neutralization test based on recombinant NDV expressing enhanced green fluorescent protein," Virol. J., 14(1):232 (11 pages).

ClinicalTrial NCT04764422 (v1), "A Phase 1/2 Randomized, Placebo-controlled, Observer-blind Trial to Assess the Safety and Immunogenicity of NDV-HXP-S Vaccine in Adults Aged 18-60 Years in Thailand," first posted Feb. 21, 2021, last update posted Feb. 21, 2021 (13 pages).

ClinicalTrial NCT04764422 (v10), "A Phase 1/2 Randomized, Placebo-controlled, Observer-blind Trial to Assess the Safety and Immunogenicity of NDV-HXP-S Vaccine in Thailand," first posted Feb. 21, 2021, last update posted Nov. 15, 2022 (11 pages).

ClinicalTrial NCT04764422 (v2), "A Phase 1/2 Randomized, Placebo-controlled, Observer-blind Trial to Assess the Safety and Immunogenic-ity of NDV-HXP-S Vaccine in Adults Aged 18-60 Years in Thailand," first posted Feb. 21, 2021, last update posted Feb. 23, 2021 (13 pages).

ClinicalTrial NCT04764422 (v3), "A Phase 1/2 Randomized, Placebo-controlled, Observer-blind Trial to Assess the Safety and Immunogenicity of NDV-HXP-S Vaccine in Thailand," first posted Feb. 21, 2021, last update posted Feb. 25, 2021 (13 pages).

ClinicalTrial NCT04764422 (v4), "A Phase 1/2 Randomized, Placebo-controlled, Observer-blind Trial to Assess the Safety and Immunogenicity of NDV-HXP-S Vaccine in Thailand," first posted Feb. 21, 2021, last update posted Mar. 3, 2021 (13 pages).

ClinicalTrial NCT04764422 (v5), "A Phase 1/2 Randomized, Placebo-controlled, Observer-blind Trial to Assess the Safety and Immunogenicity of NDV-HXP-S Vaccine in Thailand," first posted Feb. 21, 2021, last update posted Mar. 16, 2021 (13 pages).

ClinicalTrial NCT04764422 (v6), "A Phase 1/2 Randomized, Placebo-controlled, Observer-blind Trial to Assess the Safety and Immunogenicity of NDV-HXP-S Vaccine in Thailand," first posted Feb. 21, 2021, last update posted Apr. 1, 2021 (13 pages).

ClinicalTrial NCT04764422 (v7), "A Phase 1/2 Randomized, Placebo-controlled, Observer-blind Trial to Assess the Safety and Immunogenicity of NDV-HXP-S Vaccine in Thailand," first posted Feb. 21, 2021, last update posted Mar. 29, 2022 (11 pages).

ClinicalTrial NCT04764422 (v8), "A Phase 1/2 Randomized, Placebo-controlled, Observer-blind Trial to Assess the Safety and Immunogenicity of NDV-HXP-S Vaccine in Thailand," first posted Feb. 21, 2021, last update posted Aug. 25, 2022 (11 pages).

ClinicalTrial NCT04764422 (v9), "A Phase 1/2 Randomized, Placebo-controlled, Observer-blind Trial to Assess the Safety and Immunogenicity of NDV-HXP-S Vaccine in Thailand," first posted Feb. 21, 2021, last update posted Nov. 14, 2022 (12 pages).

ClinicalTrial NCT04830800 (v1), "A Phase 1/2 Randomized, Placebo-controlled, Observer-blind Trial to Assess the Safety and Immunogenicity of COVIVAC Vaccine Produced by IVAC in Adults Aged 18-75 Years in Vietnam," first posted Apr. 5, 2021, last update posted Apr. 5, 2021 (10 pages).

ClinicalTrial NCT04830800 (v2), "A Phase 1/2 Randomized, Placebo-controlled, Observer-blind Trial to Assess the Safety and Immunogenicity of COVIVAC Vaccine Produced by IVAC in Adults Aged 18-75 Years in Vietnam," first posted Apr. 5, 2021, last update posted Nov. 14, 2022 (9 pages).

Ehichioya et al., 2019, "Phylogeography of Lassa Virus in Nigeria," J. Virol., 93(21):e00929-19 (12 pages).

Erbelding et al., 2018, "A Universal Influenza Vaccine: The Strategic Plan for the National Institute of Allergy and Infectious Diseases," J. Infect. Dis., 218(3):347-354.

Escalera et al., 2022, "Mutations in SARS-CoV-2 variants of concern link to increased spike cleavage and virus transmission," Cell Host Microbe., 30(3):373-387.e7 (24 pages).

Escriou et al., 2014, "Protection from SARS coronavirus conferred by live measles vaccine expressing the spike glycoprotein," Virology, 452-453:32-41.

Faria et al., 2021, "Genomic characterisation of an emergent SARS-CoV-2 lineage in Manaus: preliminary findings," Virological (5 pages).

Fox et al., 2022, "The IgA in milk induced by SARS-CoV-2 infection is comprised of mainly secretory antibody that is neutralizing and highly durable over time," PLoS One, 17(3):e0249723 (14 pages).

Fox et al., 2020, "Evidence of a significant secretory-IgA-dominant SARS-CoV-2 immune response in human milk following recovery from COVID-19," medRxiv 2020.05.04.20089995 (13 pages).

Fox et al., 2020, "Robust and Specific Secretory IgA Against SARS-CoV-2 Detected in Human Milk," iScience, 23(11):101735 (13 pages).

Freeman et al., 2006, "Phase I/II trial of intravenous NDV-HUJ oncolytic virus in recurrent glioblastoma multiforme," Mol. Ther., 13:221-228.

Gagne et al., 2022, "mRNA-1273 or mRNA-Omicron boost in vaccinated macaques elicits comparable B cell expansion, neutralizing antibodies and protection against Omicron," bioRxiv, 2022.02.03.479037 (51 pages).

(56) References Cited

OTHER PUBLICATIONS

Gandhapudi et al., 2019, "Antigen Priming with Enantiospecific Cationic Lipid Nanoparticles Induces Potent Antitumor CTL Responses through Novel Induction of a Type I IFN Response," J. Immunol., 202(12):3524-3536.
Gao et al., "Expression of transgenes from newcastle disease virus with a segmented genome," J. Virol., 82(6):2692-2698 (2008).
Gao et al., 2003, "Effects of a SARS-associated coronavirus vaccine in monkeys," Lancet, 362(9399):1895-1896.
Gao et al., 2020, "Development of an inactivated vaccine candidate for SARS-CoV-2," Science, 369(6499):77-81 and Supplementary Materials (9 pages).
Garcia-Beltran et al., 2021, "Multiple SARS-CoV-2 variants escape neutralization by vaccine-induced humoral immunity," Cell, 184(9):2372-2383.e9.
Garcia-Sastre et al., "Introduction of foreign sequences into the genome of influenza A virus," Dev. Biol. Stand., 82:237-246 (1994).
Garcia-Sastre et al., "Use of a mammalian internal ribosomal entry site element for expression of a foreign protein by a transfectant influenza virus," J. Virol., 68:6254-6261 (1994).
Genbank Accession No. AAS67141.1, "fusion protein [Avian avulavirus 1]," Mar. 22, 2004.
Genbank Accession No. AAS67147.1, "fusion protein [Avian avulavirus 1]," Mar. 22, 2004.
Genbank Accession No. AAS67153.1, "fusion protein [Avian avulavirus 1]," Mar. 22, 2004.
Genbank Accession No. AAS67159.1, "fusion protein [Avian avulavirus 1]," Mar. 22, 2004.
Genbank Accession No. AAS67165.1, "fusion protein [Avian avulavirus 1]," Mar. 22, 2004.
Genbank Accession No. ACJ53752.1, "fusion protein [Avian avulavirus 1]," Nov. 25, 2008.
Genbank Accession No. ACJ53758.1, "fusion protein [Avian avulavirus 1]," Nov. 25, 2008.
Genbank Accession No. ACK57498.1, "fusion protein [Avian avulavirus 1]," Apr. 19, 2011.
Genbank Accession No. ADF59234.1, "fusion protein [Avian avulavirus 1]," Aug. 16, 2011.
Genbank Accession No. AF124443.1, "Newcastle disease virus isolate Roakin matrix protein mRNA, complete cds," Mar. 6, 2000.
Genbank Accession No. AF309418.1, "Newcastle disease virus B1, complete genome," Dec. 2, 2000.
Genbank Accession No. AF375823.1, Newcastle disease virus strain B1 isolate Takaaki, complete genome, dated Nov. 6, 2001.
Genbank Accession No. AIA66951.1, "fusion protein [Avian avulavirus 1]," Jun. 4, 2014.
Genbank Accession No. AY143159.1, "Newcastle disease virus strain MET95 hemagglutinin-neuraminidase protein HN gene, complete cds," Jul. 25, 2003.
Genbank Accession No. AY351959.1, "Newcastle disease virus hemagglutinin-neuraminidase gene, complete cds," Aug. 25, 2003.
Genbank Accession No. AY390310.1, "Newcastle disease virus strain YG97 from goose fusion protein gene, partial cds," Jul. 26, 2016.
Genbank Accession No. AY845400.2, "Newcastle disease virus strain LaSota, complete genome," Mar. 17, 2005,.
Genbank Accession No. EU293914.1, "Newcastle disease virus strain Italien, complete genome," Jun. 24, 2008.
Genbank Accession No. EU338414.1, "Avian paramyxovirus 2 strain APMV-2/Chicken/California/Yucaipa/56, complete genome," Sep. 3, 2008.
Genbank Accession No. EU622637.2, "Avian paramyxovirus 6 strain APMV-6/duck/HongKong/18/199/77, complete genome," Feb. 25, 2011.
Genbank Accession No. EU782025.1, "Avian paramyxovirus 3 strain turkey/Wisconsin/68, complete genome," Mar. 26, 2010.
Genbank Accession No. EU910942.1, "Avian paramyxovirus 9 strain duck/New York/22/1978, complete genome," May 8, 2009 (8 pages).
Genbank Accession No. FJ177514.1, "Avian paramyxovirus 4 strain APMV-4/duck/Hongkong/D3/75, complete genome," Nov. 4, 2008.
Genbank Accession No. FJ215863.2, "Avian paramyxovirus 8 strain goose/Delaware/1053/76, complete genome," Mar. 20, 2015 (8 pages).
Genbank Accession No. FJ231524.1, "Avian paramyxovirus 7 strain APMV-7/dove/Tennessee/4/75, complete genome," Sep. 10, 2009.
Genbank Accession No. JF950510.1, Newcastle disease virus strain LaSota, complete genome, Aug. 10, 2011.
Genbank Accession No. JQ886184.1, "Avian paramyxovirus 11 isolate common_snipe/France/100212/2010, complete genome," Jul. 4, 2012 (9 pages).
Genbank Accession No. KC333050.1, "Avian paramyxovirus 12 isolate Wigeon/Italy/3920_1/2005, complete genome," Mar. 24, 2013 (8 pages).
Genbank Accession No. MK167211.1, "*Avulavirus* sp. isolate AAvV-17/Adelie penguin/Antarctica/107/2013, partial genome," Mar. 13, 2019 (8 pages).
Genbank Accession No. MK677433.1, "Avian metaavulavirus 21 isolate APMV/pigeon/Taiwan/AHRI128/2017, complete genome," Sep. 23, 2019 (8 pages).
Genbank Accession No. MN908947.3, "Severe acute respiratory syndrome coronavirus 2 isolate Wuhan-Hu-1, complete genome," Mar. 18, 2020 (11 pages).
Genbank Accession No. MT020880.1, "Severe acute respiratory syndrome coronavirus 2 isolate SARS-CoV-2/human/USA/WA-CDC-02982585-001/2020, complete genome," Jan. 7, 2022 (11 pages).
Genbank Accession No. MT081066.1, "Severe acute respiratory syndrome coronavirus 2 isolate SARS-CoV-2/human/CHN/HS_86/2020 nucleocapsid phosphoprotein (N) gene, complete cds," Apr. 6, 2020 (2 pages).
Riehl et al., 2017, "Combining R-DOTAP and a particulate antigen delivery platform to trigger dendritic cell activation: Formulation development and in-vitro interaction studies," Int. J. Pharm., 532(1):37-46.
Rima et al., 2019, "ICTV Virus Taxonomy Profile: Paramyxoviridae," J. Gen. Virol., 100(12):1593-1594.
Roberts et al., 1998, "Recovery of Negative-Strand RNA Virus from Plasmid DNAs: A Positive Approach Revitalizes a Negative Field," Virology 247:1-6.
Rohaim et al., 2020, "A Scalable Topical Vectored Vaccine Candidate against SARS-CoV-2," Vaccines (Basel), 8(3):472 (16 pages).
Romer-Oberdorfer et al., 1999, "Generation of recombinant lentogenic Newcastle disease virus from cDNA" J Gen Virol., 80(Pt 11):2987-2995.
Rose, 1996, "Positive strands to the rescue again: a segmented negative-strand RNA virus derived from cloned cDNAs," Proc. Natl. Acad. Sci. USA, 93(26):14998-15000.
Sagulenko et al., 2018, "TreeTime: Maximum-likelihood phylodynamic analysis," Virus Evol., 4(1):vex042 (9 pages).
Sahin et al., 2020, "COVID-19 vaccine BNT162b1 elicits human antibody and TH1 T cell responses," Nature, 586(7830):594-599 and Supplementary Materials (23 pages).
Salam et al., 2021, "Time to reconsider the role of ribavirin in Lassa fever," PLoS Negl. Trop. Dis., 15(7):e0009522 (5 pages).
Salami et al., 2019, "A review of Lassa fever vaccine candidates," Curr. Opin. Virol., 37:105-111.
Samuel et al., 2011, "Experimental infection of hamsters with avian paramyxovirus serotypes 1 to 9," Vet. Res., 42(1):38 (12 pages).
Santry et al., 2017, "Production and Purification of High-Titer Newcastle Disease Virus for Use in Preclinical Mouse Models of Cancer," Mol. Ther. Methods Clin. Dev., 9:181-191.
Saphire et al., 2018, "Antibody-mediated protection against Ebola virus," Nat. Immunol., 19(11):1169-1178.
Schirrmacher et al., "Newcastle disease virus: a promising vector for viral therapy, immune therapy, and gene therapy of cancer," Methods Mol. Biol., 542: 565-605 (2009).
Schirrmacher, 2016, "Fifty Years of Clinical Application of Newcastle Disease Virus: Time to Celebrate!" Biomedicines, 4(3), 14 pages.
Schlesinger, 1995, "RNA viruses as vectors for the expression of heterologous proteins," Mol. Biotechnol., 3(2):155-165.

(56) References Cited

OTHER PUBLICATIONS

Sergel et al., "A Single Amino Acid Change in the Newcastle Disease Virus Fusion Protein Alters the Requirement for HN Protein in Fusion," J. Virol., 74(11):5101-5107 (2000).

Sharpet et al., 2001, "Induction of simian immunodeficiency virus (SIV)-specific CTL in rhesus macaques by vaccination with modified vaccinia virus Ankara expressing SIV transgenes: influence of pre-existing anti-vector immunity," J. Gen. Virol., 82(Pt 9):2215-2223.

Shen et al., 2020, "Treatment of 5 Critically Ill Patients With COVID-19 With Convalescent Plasma," JAMA, 323(16):1582-1589.

Shen et al., 2021, "Neutralization of SARS-CoV-2 Variants B.1.429 and B.1.351," N. Engl. J. Med., 384(24):2352-2354.

Shi et al., 2020, "A human neutralizing antibody targets the receptor-binding site of SARS-CoV-2," Nature, 584(7819):120-124 and Supplementary Materials (23 pages).

Shivarov et al., 2020, "Potential SARS-CoV-2 Preimmune IgM Epitopes," Front Immunol., 11:932 (5 pages).

Shortridge et al., 1978, "Incidence and preliminary characterisation of a hitherto unreported, serologically distinct, avian paramyxovirus isolated in Hong Kong," Res. Vet Sci., 25(1):128-130.

Shukla et al., 2010, "Structure-activity relationships in human toll-like receptor 7-active imidazoquinoline analogues," J. Med. Chem., 53(11):4450-4465.

Shukla et al., 2011, "Toward self-adjuvanting subunit vaccines: model peptide and protein antigens incorporating covalently bound toll-like receptor-7 agonistic imidazoquinolines," Bioorg. Med. Chem. Lett., 21(11):3232-3236.

Sinkovics et al., "Newcastle disease virus (NDV): brief history of its oncolytic strains," J. Clin. Virol., 16:1-15 (2000).

Slamanig et al., 2022, "Intranasal administration of NDV-HXP-S COVID19 vaccines induces robust protective mucosal and systemic immunity in mice," Engineering Conferences International, Jun. 12, 2022 (2 pages).

Smalley Rumfield et al., 2020, "Immunomodulation to enhance the efficacy of an HPV therapeutic vaccine," J. Immunother. Cancer, 8(1):e000612 (12 pages).

Sparrow et al., 2021, "Global production capacity of seasonal and pandemic influenza vaccines in 2019," Vaccine, 39(3):512-520 (Epub 2020).

Stadlbauer et al., 2020, "SARS-CoV-2 Seroconversion in Humans: A Detailed Protocol for a Serological Assay, Antigen Production, and Test Setup," Curr. Protoc. Microbiol., 57(1):e100 (15 pages).

Stadlbauer et al., 2020, "Seroconversion of a city: Longitudinal monitoring of SARS-CoV-2 seroprevalence in New York City," medRxiv, 2020.06.28.20142190 (17 pages).

State Key Laboratory of Respiratory Disease, 2020, "Laboratories Jointly Developed a Rapid Detection Kit for New Coronavirus IgM Antibodies," Research Progress, Feb. 14, 2020, in Chinese with machine English translation (6 pages).

Steglich et al., 2013, "Chimeric newcastle disease virus protects chickens against avian influenza in the presence of maternally derived NDV immunity," PLoS One, 8(9):e72530 (14 pages).

Stoute et al., 1997, "A preliminary evaluation of a recombinant circumsporozoite protein vaccine against Plasmodium falciparum malaria. RTS,S Malaria Vaccine Evaluation Group," N. Engl. J. Med., 336(2):86-91.

Sun et al., 2020, "A Newcastle Disease Virus (NDV) Expressing a Membrane-Anchored Spike as a Cost-Effective Inactivated SARS-CoV-2 Vaccine," Vaccines (Basel), 8(4):771 (14 pages).

Sun et al., 2020, "A Newcastle disease virus (NDV) expressing membrane-anchored spike as a cost-effective inactivated SARS-CoV-2 vaccine," bioRxiv, 2020.07.30.229120 (23 pages).

Sun et al., 2020, "Generation of a Broadly Useful Model for COVID-19 Pathogenesis, Vaccination, and Treatment," Cell, 182(3):734-743.e5 (17 pages).

Sun et al., 2020, "Newcastle disease virus (NDV) expressing the spike protein of SARS-CoV-2 as a live virus vaccine candidate," EBioMedicine, 62:103132 (9 pages).

Sun et al., 2020, "Newcastle disease virus (NDV) expressing the spike protein of SARS-CoV-2 as vaccine candidate," bioRxiv, 2020.07.26.221861 (22 pages).

Sun et al., 2020, "SARS-CoV-2 and SARS-CoV Spike-RBD Structure and Receptor Binding Comparison and Potential Implications on Neutralizing Antibody and Vaccine Development ," bioRxiv, 2020.02.16.951723 (18 pages).

Sun et al., 2021, "A Newcastle disease virus expressing a stabilized spike protein of SARS-CoV-2 induces protective immune responses," Nat. Commun., 12(1):6197 (14 pages).

Sun et al., 2021, "A Newcastle disease virus-vector expressing a prefusion-stabilized spike protein of SARS-CoV-2 induces protective immune responses against prototype virus and variants of concern in mice and hamsters," bioRxiv, 2021.07.06.451301 (35 pages).

Swayne et al., "Recombinant paramyxovirus type 1-avian influenza-H7 virus as a vaccine for protection of chickens against influenza and Newcastle disease," Avian Dis., 47:1047-1050 (2003).

Takeda, 2022, "Proteolytic activation of SARS-CoV-2 spike protein," Microbiol. Immunol., 66(1):15-23 (Epub 2021).

Taylor et al., 1990, "Newcastle Disease Virus Fusion Protein Expressed in a Fowlpox Virus Recombinant Confers Protection in Chickens," J. Virol. 64:1441-1450.

Tcheou et al., 2021, "Safety and Immunogenicity Analysis of a Newcastle Disease Virus (NDV-HXP-S) Expressing the Spike Protein of SARS-CoV-2 in Sprague Dawley Rats," Front Immunol., 12:791764 (12 pages).

Ter Meulen et al., 2006, "Human monoclonal antibody combination against SARS coronavirus: synergy and coverage of escape mutants," PLoS Med., 3(7):e237 (9 pages).

Thulin et al., 2018, "The Role of Fc Gamma Receptors in Broad Protection against Influenza Viruses," Vaccines (Basel), 6(3):36 (10 pages).

Tian et al., 2020, "Potent binding of 2019 novel coronavirus spike protein by a SARS coronavirus-specific human monoclonal antibody," Emerg. Microbes. Infect., 9(1):382-385.

To et al., 2020, "Consistent Detection of 2019 Novel Coronavirus in Saliva," Clin. Infect. Dis., 71(15):841-843.

Tseng et al., 2012, "Immunization with SARS coronavirus vaccines leads to pulmonary immunopathology on challenge with the SARS virus," PLoS One, 7(4):e35421 (13 pages).

UniProtKB Accession No. P0DTC2, "Spike glycoprotein," Apr. 22, 2020 [online]. [Retrieved on Oct. 4, 2021]. Retrieved from the Internet: <URL: https://www.uniprot.org/uniprotkb/PODTC2> (30 pages).

Urlaub et al., 1983, "Deletion of the diploid dihydrofolate reductase locus from cultured mammalian cells," Cell, 33(2):405-412.

Van Herck et al., 2018, "Lymph-Node-Targeted Immune Activation by Engineered Block Copolymer Amphiphiles-TLR7/8 Agonist Conjugates," J. Am. Chem. Soc., 140(43):14300-14307.

Vasievich et al., 2012, "Trp2 peptide vaccine adjuvanted with (R)-DOTAP inhibits tumor growth in an advanced melanoma model," Mol. Pharm., 9(2):261-268.

Veits et al., 2006, "Newcastle disease virus expressing H5 hemagglutinin gene protects chickens against Newcastle disease and avian influenza," Proceedings of the National Academy of Sciences of the United States of America, 103:8197-8202.

Vigil et al., 2008, "Recombinant Newcastle disease virus as a vaccine vector for cancer therapy," Molecular Therapy, 16(11):1883-1890.

Vijayakumar et al., 2019, "Oncolytic Newcastle disease virus expressing a checkpoint inhibitor as a radioenhancing agent for murine melanoma," EBioMedicine, 49:96-105.

Vijayakumar et al., 2020, "Design and Production of Newcastle Disease Virus for Intratumoral Immunomodulation," Methods Mol. Biol., 2058:133-154.

Wajnberg et al., 2020, "Humoral immune response and prolonged PCR positivity in a cohort of 1343 SARS-CoV 2 patients in the New York City region," medRxiv, 2020.04.30.20085613 (17 pages).

Wakamatsu et al., "The effect on pathogenesis of Newcastle disease virus LaSota strain from a mutation of the fusion cleavage site to a virulent sequence," Avian Dis., 50(4):483-488 (2006).

(56) References Cited

OTHER PUBLICATIONS

Walls et al., 2016, "Cryo-electron microscopy structure of a coronavirus spike glycoprotein trimer," Nature, 531(7592):114-117 and Supplementary Materials (17 pages).

Walls et al., 2020, "Structure, Function, and Antigenicity of the SARS-CoV-2 Spike Glycoprotein," Cell, 181(2):281-292.e6.

Wang et al., 2016, "Immunogenicity and Safety of an Inactivated Quadrivalent Influenza Vaccine in US Children 6-35 Months of Age During 2013-2014: Results From A Phase II Randomized Trial," J. Pediatric Infect. Dis. Soc., 5(2):170-179 (Epub 2015).

Wang et al., 2020, "Remdesivir in adults with severe COVID-19: a randomised, double-blind, placebo-controlled, multicentre trial," Lancet, 395(10236):1569-1578.

Wang et al., 2021, "Antibody resistance of SARS-CoV-2 variants B.1.351 and B.1.1.7," Nature, 593(7857):130-135 and Supplementary Materials (18 pages).

Wang et al., 2021, "mRNA vaccine-elicited antibodies to SARS-CoV-2 and circulating variants," Nature, 592(7855):616-622 and Supplementary Materials (23 pages).

Wang et al., 2021, "Resistance of SARS-CoV-2 Delta variant to neutralization by BNT162b2-elicited antibodies in Asians," Lancet Reg. Health West Pac., 15:100276 (4 pages).

Warke et al., 2008, "Comparative study on the pathogenicity and immunogenicity of wild bird isolates of avian paramyxovirus 2, 4, and 6 in chickens," Avian Pathol., 37(4):429-434.

Wei et al., 2020, "Redox-Responsive Polycondensate Neoepitope for Enhanced Personalized Cancer Vaccine," ACS Cent. Sci., 6(3):404-412.

Wignall-Fleming et al., 2019, "Analysis of Paramyxovirus Transcription and Replication by High-Throughput Sequencing," J. Virol., 93(17):e00571-19 (17 pages).

Wohlbold et al., 2017, "Broadly protective murine monoclonal antibodies against influenza B virus target highly conserved neuraminidase epitopes," Nat. Microbiol., 2(10):1415-1424.

Wolfel et al., 2020, "Virological assessment of hospitalized patients with COVID-2019," Nature, 581(7809):465-469 and Supplementary Materials (12 pages).

Woo et al., 2004, "Longitudinal profile of immunoglobulin G (IgG), IgM, and IgA antibodies against the severe acute respiratory syndrome (SARS) coronavirus nucleocapsid protein in patients with pneumonia due to the SARS coronavirus," Clin. Diagn. Lab Immunol., 11(4):665-668.

Wrapp et al., 2020, "Cryo-EM Structure of the 2019-nCOV Spike in the Prefusion Conformation," bioRxiv, 2020.02.11.944462 (30 pages).

Wrapp et al., 2020, "Cryo-EM structure of the 2019-nCoV spike in the prefusion conformation," Science, 367(6483):1260-1263.

Wu et al., 2009, "Crystal structure of NL63 respiratory coronavirus receptor-binding domain complexed with its human receptor," Proc. Natl. Acad. Sci. USA, 106(47):19970-19974.

Wu et al., 2020, "A new coronavirus associated with human respiratory disease in China," Nature, 579(7798):265-269 and Supplementary Materials (20 pages).

Wu et al., 2020, "Immunological detection method for new coronavirus—ELISA method," Chinese Society of Immunology, Feb. 14, 2020, in Chinese with machine English translation (8 pages).

Wu et al., 2021, "mRNA-1273 vaccine induces neutralizing antibodies against spike mutants from global SARS-CoV-2 variants," bioRxiv, 2021.01.25.427948 (20 pages).

Wu et al., 2021, "Preliminary Analysis of Safety and Immunogenicity of a SARS-CoV-2 Variant Vaccine Booster," medRxiv, 2021.05.05.21256716 (31 pages).

Wurm et al., 2011, "First CHO genome," Nat. Biotechnol., 29(8):718-720.

Xia et al., 2020, "The role of furin cleavage site in SARS-CoV-2 spike protein-mediated membrane fusion in the presence or absence of trypsin," Signal Transduct Target Ther., 5(1):92 (3 pages).

Xia, 2021, "Domains and Functions of Spike Protein in Sars-Cov-2 in the Context of Vaccine Design," Viruses, 13 (1):109 (16 pages).

Yang et al., 2021, "Newcastle Disease Virus-Like Particles Displaying Prefusion-Stabilized SARS-CoV-2 Spikes Elicit Potent Neutralizing Responses," Vaccines (Basel), 9(2):73 (17 pages).

Yap et al., 2011, "Use of saliva for early dengue diagnosis," PLoS Negl. Trop. Dis., 5(5):e1046 (7 pages).

Ye et al., 2020, "Current Status of COVID-19 (Pre)Clinical Vaccine Development," Angew Chem. Int. Ed. Engl., 59(43):18885-18897.

Yu et al., 2020, "DNA vaccine protection against SARS-CoV-2 in rhesus macaques," Science, 369(6505):806-811.

Yuan et al., 2020, "A highly conserved cryptic epitope in the receptor binding domains of SARS-CoV-2 and SARS-CoV," Science, 368(6491):630-633.

Yusoff et al., 1987, "Nucleotide Sequence Analysis of the L Gene of Newcastle Disease Virus: Homologies with Sendai and Vesicular Stomatitis Viruses," Nucleic Acids Res., 15:3961-3976.

Zamarin et al., 2012, "Oncolytic Newcastle disease virus for cancer therapy: old challenges and new directions," Future Microbiol., 7:347-367.

Zhang et al., 2020, "Molecular and serological investigation of 2019-nCoV infected patients: implication of multiple shedding routes," Emerg. Microbes. Infect., 9(1):386-389.

Zhao et al., "P and M gene junction is the optimal insertion site in Newcastle disease virus vaccine vector for foreign gene expression," J. Gen. Virol., 96(Pt 1):40-45 (2015) (Epub Oct. 1, 2014).

Zhao et al., 2020, "Antibody Responses to SARS-CoV-2 in Patients With Novel Coronavirus Disease 2019," Clin. Infect. Dis., 71(16):2027-2034.

Zhi et al., 2006, "Efficacy of severe acute respiratory syndrome vaccine based on a nonhuman primate adenovirus in the presence of immunity against human adenovirus," Hum. Gene. Ther., 17(5):500-506.

Zhou et al., 2020, "A pneumonia outbreak associated with a new coronavirus of probable bat origin," Nature, 579(7798):270-273 and Supplementary Materials (20 pages).

Zhou et al., 2022, "Neutralization against Omicron SARS-CoV-2 from previous non-Omicron infection," Nat. Commun., 13(1):852 (4 pages).

Zhu et al., 2020, "A Novel Coronavirus from Patients with Pneumonia in China, 2019," N. Engl. J. Med., 382(8):727-733.

Zhu et al., 2020, "Safety, tolerability, and immunogenicity of a recombinant adenovirus type-5 vectored COVID-19 vaccine: a dose-escalation, open-label, non-randomised, first-in-human trial," Lancet, 395(10240):1845-1854.

ClinicalTrial NCT04871737 (v1), "Dose-escalation, Open-label, Non-randomized Phase I Study to Evaluate the Safety and Immunogenicity of Three Concentrations of a rNDV Vaccine Against SARS-CoV-2 Administered by the Intranasal and Intramuscular Route to Healthy Volunteers," first posted May 4, 2021, last update posted May 4, 2021 (13 pages).

ClinicalTrial NCT04871737 (v2), "Dose-escalation, Open-label, Non-randomized Phase I Study to Evaluate the Safety and Immunogenicityof Three Concentrations of a rNDV Vaccine Against SARS-CoV-2 Administered by the Intranasal andIntramuscular Route to Healthy Volunteers," first posted May 4, 2021, last update posted May 27, 2021 (19 pages).

ClinicalTrial NCT04871737 (v3), "Dose-escalation, Open-label, Non-randomized Phase I Study to Evaluate the Safety and Immunogenicity of Three Concentrations of a rNDV Vaccine Against SARS-CoV-2 Administered by the Intranasal and Intramuscular Route to Healthy Volunteers," first posted May 4, 2021, last update posted Feb. 8, 2022 (13 pages).

ClinicalTrial NCT04871737 (v4), "Dose-escalation, Open-label, Non-randomized Phase I Study to Evaluate the Safety and Immunogenicity of Three Concentrations of a rNDV Vaccine Against SARS-CoV-2 Administered by the Intranasal and Intramuscular Route to Healthy Volunteers," first posted May 4, 2021, last update posted Dec. 9, 2022 (13 pages).

ClinicalTrial NCT04871737 (v5), "Dose-escalation, Open-label, Non-randomized Phase I Study to Evaluate the Safety and Immunogenicity of Three Concentrations of a rNDV Vaccine Against SARS-CoV-2 Administered by the Intranasal and Intramuscular Route to Healthy Volunteers," first posted May 4, 2021, last update posted Jul. 25, 2023 (13 pages).

(56) References Cited

OTHER PUBLICATIONS

ClinicalTrial NCT04993209 (v1), "Phase I/II Double-blind, Randomized, Stepwise, Adaptive, Controlled Clinical Trial to Assess the Safety and Immunogenicity of the COVID-19 Vaccine (Recombinant, Inactivated) in Adults, in Brazil—ADAPTCOV," first posted Aug. 6, 2021, last update posted Aug. 6, 2021 (16 pages).

ClinicalTrial NCT04993209 (v2), "Double-blind, Randomized, With an Active Control Vaccine, Phase I Clinical Trial for Evaluation of Safety and Immunogenicity of a Recombinant Inactivated COVID-19 Vaccine in Adults in Brazil—ADAPTCOV," first posted Aug. 6, 2021, last update posted Jun. 3, 2022 (9 pages).

ClinicalTrial NCT04993209 (v3), "Double-blind, Randomized, With an Active Control Vaccine, Phase I Clinical Trial for Evaluation of Safety and Immunogenicity of a Recombinant Inactivated COVID-19 Vaccine in Adults in Brazil—ADAPTCOV," first posted Aug. 6, 2021, last update posted Jun. 6, 2022 (9 pages).

ClinicalTrial NCT04993209 (v4), "Double-blind, Randomized, With an Active Control Vaccine, Phase I Clinical Trial for Evaluation of Safety and Immunogenicity of a Recombinant Inactivated COVID-19 Vaccine in Adults in Brazil—ADAPTCOV," first posted Aug. 6, 2021, last update posted Aug. 21, 2023 (9 pages).

ClinicalTrial NCT05181709 (v1), "A Phase-1, Open-Label, Placebo-Controlled Evaluation of a Live, Recombinant Newcastle Disease Virus Expressing the Spike Protein of SARS-CoV-2 (NDV-HXP-S), an Investigational Product for Intranasal (IN) and/or Intramuscular (IM) Vaccination in Healthy Adults Previously Immunized Against COVID-19," first posted Jan. 6, 2022, last update posted Jan. 6, 2022 (10 pages).

ClinicalTrial NCT05181709 (v2), "A Phase-1, Open-Label, Placebo-Controlled Evaluation of a Live, Recombinant Newcastle Disease Virus Expressing the Spike Protein of SARS-CoV-2 (NDV-HXP-S), an Investigational Product for Intranasal (IN) and/or Intramuscular (IM) Vaccination in Healthy Adults Previously Immunized Against COVID-19," first posted Jan. 6, 2022, last update posted Apr. 5, 2022 (10 pages).

ClinicalTrial NCT05181709 (v3), "A Phase-1, Open-Label, Placebo-Controlled Evaluation of a Live, Recombinant Newcastle Disease Virus Expressing the Spike Protein of SARS-CoV-2 (NDV-HXP-S), an Investigational Product for Intranasal (IN) and/or Intramuscular (IM) Vaccination in Healthy Adults Previously Immunized Against COVID-19," first posted Jan. 6, 2022, last update posted May 20, 2022 (10 pages).

ClinicalTrial NCT05181709 (v4), "A Phase-1, Open-Label, Placebo-Controlled Evaluation of a Live, Recombinant Newcastle Disease Virus Expressing the Spike Protein of SARS-CoV-2 (NDV-HXP-S), an Investigational Product for Intranasal (IN) and/or Intramuscular (IM) Vaccination in Healthy Adults Previously Immunized Against COVID-19," first posted Jan. 6, 2022, last update posted Jul. 5, 2022 (10 pages).

ClinicalTrial NCT05181709 (v5), "A Phase-1, Open-Label, Placebo-Controlled Evaluation of a Live, Recombinant Newcastle Disease Virus Expressing the Spike Protein of SARS-CoV-2 (NDV-HXP-S), an Investigational Product for Intranasal (IN) and/or Intramuscular (IM) Vaccination in Healthy Adults Previously Immunized Against COVID-19," first posted Jan. 6, 2022, last update posted Dec. 8, 2022 (10 pages).

ClinicalTrial NCT05181709 (v6), "A Phase-1, Open-Label, Placebo-Controlled Evaluation of a Live, Recombinant Newcastle Disease Virus Expressing the Spike Protein of SARS-CoV-2 (NDV-HXP-S), an Investigational Product for Intranasal (IN) and/or Intramuscular (IM) Vaccination in Healthy Adults Previously Immunized Against COVID-19," first posted Jan. 6, 2022, last update posted Mar. 29, 2023 (10 pages).

ClinicalTrial NCT05181709 (v7), "A Phase-1, Open-Label, Placebo-Controlled Evaluation of a Live, Recombinant Newcastle Disease Virus Expressing the Spike Protein of SARS-CoV-2 (NDV-HXP-S), an Investigational Product for Intranasal (IN) and/or Intramuscular (IM) Vaccination in Healthy Adults Previously Immunized Against COVID-19," first posted Jan. 6, 2022, last update posted Apr. 21, 2023 (10 pages).

ClinicalTrial NCT05354024 (v1), "Phase II/III Double-blind, Randomized Clinical Trial With Active Vaccine Control to Evaluate the Safety, Immunogenicity, and Consistency of the Lots of Booster Dose of COVID-19 (Recombinant, Inactivated) Vaccine in Adults in Brazil," first posted Apr. 29, 2022, last update posted Apr. 29, 2022 (10 pages).

ClinicalTrial NCT05354024 (v2), "Phase II/III Double-blind, Randomized Clinical Trial With Active Vaccine Control to Evaluate the Safety, Immunogenicity, and Consistency of the Lots of Booster Dose of COVID-19 (Recombinant, Inactivated) Vaccine in Adults in Brazil," first posted Apr. 29, 2022, last update posted May 5, 2022 (10 pages).

ClinicalTrial NCT05354024 (v3), "Phase II/III Double-blind, Randomized Clinical Trial With Active Vaccine Control to Evaluate the Safety, Immunogenicity, and Consistency of the Lots of Booster Dose of COVID-19 (Recombinant, Inactivated) Vaccine in Adults in Brazil," first posted Apr. 29, 2022, last update posted May 20, 2022 (10 pages).

ClinicalTrial NCT05354024 (v4), "Phase II/III Double-blind, Randomized Clinical Trial With Active Vaccine Control to Evaluate the Safety, Immunogenicity, and Consistency of the Lots of Booster Dose of COVID-19 (Recombinant, Inactivated) Vaccine in Adults in Brazil," first posted Apr. 29, 2022, last update posted Mar. 10, 2023 (10 pages).

ClinicalTrial NCT05354024 (v5), "Phase II/III Double-blind, Randomized Clinical Trial With Active Vaccine Control to Evaluate the Safety, Immunogenicity, and Consistency of the Lots of Booster Dose of COVID-19 (Recombinant, Inactivated) Vaccine in Adults in Brazil," first posted Apr. 29, 2022, last update posted Apr. 27, 2023 (10 pages).

ClinicalTrial NCT05354024 (v6), "Phase II/III Double-blind, Randomized Clinical Trial With Active Vaccine Control to Evaluate the Safety, Immunogenicity, and Consistency of the Lots of Booster Dose of COVID-19 (Recombinant, Inactivated) Vaccine in Adults in Brazil," first posted Apr. 29, 2022, last update posted Aug. 2, 2023 (11 pages).

ClinicalTrial NCT05354024 (v7), "Phase II/III Double-blind, Randomized Clinical Trial With Active Vaccine Control to Evaluate the Safety, Immunogenicity, and Consistency of the Lots of Booster Dose of COVID-19 (Recombinant, Inactivated) Vaccine in Adults in Brazil," first posted Apr. 29, 2022, last update posted Sep. 5, 2023 (10 pages).

ClinicalTrial NCT05940194 (v1), "A Phase 1/2 Randomized, Placebo-controlled (Phase 1) and Active-Controlled (Phase 2), Observer-blind Trial to Assess the Safety and Immunogenicity of COVIVAC Vaccine Produced by IVAC in Adults ≥ 18 and ≥ 60 Years Old in Vietnam," first posted Jul. 11, 2023, last update posted Jul. 11, 2023 (8 pages).

ClinicalTrial NCT05940194 (v2), "A Phase 1/2 Randomized, Active-Controlled, Observer-blind Trial to Assess the Safety and Immunogenicity of COVIVAC Vaccine Produced by IVAC in Adults ≥ 18 and ≥ 60 Years Old in Vietnam," first posted Jul. 11, 2023, last update posted Jul. 13, 2023 (8 pages).

ClinicalTrial NCT05940194 (v3), "A Phase 1/2 Randomized, Active-Controlled, Observer-blind Trial to Assess the Safety and Immunogenicity of COVIVAC Vaccine Produced by IVAC in Adults ≥ 18 and ≥ 60 Years Old in Vietnam," first posted Jul. 11, 2023, last update posted Jul. 14, 2023 (8 pages).

Coffman et al., 2010, "Vaccine adjuvants: putting innate immunity to work," Immunity, 33(4):492-503.

Colonetti et al., 2018, "Accuracy of immunoglobulin M and immunoglobulin A of saliva in early diagnosis of dengue: Systematic Review and Meta-analysis," An. Acad. Bras. Cienc., 90(3):3147-3154.

Corbett et al., 2020, "SARS-CoV-2 mRNA Vaccine Development Enabled by Prototype Pathogen Preparedness," bioRxiv., 2020.06.11.145920 (39 pages).

Corman et al., 2020, "Detection of 2019 novel coronavirus (2019-nCoV) by real-time RT-PCR," Euro. Surveill., ;25(3):2000045 (8 pages).

Czub et al., 2005, "Evaluation of modified vaccinia virus Ankara based recombinant SARS vaccine in ferrets," Vaccine, 23(17-18):2273-2279.

(56) References Cited

OTHER PUBLICATIONS

Dang et al., 2022, "Safety and Immunogenicity of An Egg-Based Inactivated Newcastle Disease Virus Vaccine Expressing SARS-CoV-2 Spike: Interim Results of a Randomized, Placebo-Controlled, Phase 1/2 Trial in Vietnam," medRxiv, 2022.02.01. 22270253 (27 pages).

Dang et al., 2022, "Safety and immunogenicity of an egg-based inactivated Newcastle disease virus vaccine expressing SARS-CoV-2 spike: Interim results of a randomized, placebo-controlled, phase 1/2 trial in Vietnam," Vaccine, 40(26):3621-3632.

De Leeuw et al., "Virulence of Newcastle disease virus is determined by the cleavage site of the fusion protein and by both the stem region and globular head of the haemagglutinin-neuraminidase protein," J. Gen. Virol., 86(5): 1759-1769 (2005).

De Vrieze et al., 2019, "Potent Lymphatic Translocation and Spatial Control Over Innate Immune Activation by Polymer-Lipid Amphiphile Conjugates of Small-Molecule TLR7/8 Agonists," Angew Chem. Int. Ed. Engl., 58(43):15390-15395.

De Vrieze et al., 2021, "Lipid Nature and Alkyl Length Influence Lymph Node Accumulation of Lipid-Polyethylene Glycol Amphiphiles," Adv. Ther., 4(8):2100079 (9 pages).

Deming et al., 2006, "Vaccine efficacy in senescent mice challenged with recombinant SARS-CoV bearing epidemic and zoonotic spike variants," PLoS Med., 3(12):e525 (17 pages).

Deng et al., 1995, "Localization of a domain on the paramyxovirus attachment protein required for the promotion of cellular fusion by its homologous fusion protein spike," Virology, 209(2):457-469.

Deng et al., 2020, "Primary exposure to SARS-CoV-2 protects against reinfection in rhesus macaques," Science, 369(6505):818-823.

Diamond et al., 2021, "SARS-CoV-2 variants show resistance to neutralization by many monoclonal and serum-derived polyclonal antibodies," Res. Sq., rs.3.rs-228079 (17 pages).

Dinapoli et al., 2007, "Newcastle disease virus, a host range-restricted virus, as a vaccine vector for intranasal immunization against emerging pathogens," Proc. Natl. Acad. Sci. USA., 104(23):9788-9793.

Dinapoli et al., 2007, "Immunization of primates with a Newcastle disease virus-vectored vaccine via the respiratory tract induces a high titer of serum neutralizing antibodies against highly pathogenic avian influenza virus," J. Virol. 2007:11560-11568.

Dingens et al., 2020, "Serological identification of SARS-CoV-2 infections among children visiting a hospital during the initial Seattle outbreak," Nat. Commun., 11(1):4378 (6 pages).

Dinnon et al., 2020, "A mouse-adapted SARS-CoV-2 model for the evaluation of COVID-19 medical countermeasures," bioRxiv., 2020. 05.06.081497 (35 pages).

Dong et al., 2020, "Genomic and protein structure modelling analysis depicts the origin and infectivity of 2019-nCoV, a new coronavirus which caused a pneumonia outbreak in Wuhan, China," bioRxiv, 2020.01.20.913368 (14 pages).

Dortmans et al., "Virulence of Newcastle disease virus: what is known so far?" Vet. Res., 42:122 (2011).

Duan et al., 2020, "The SARS-CoV-2 Spike Glycoprotein Biosynthesis, Structure, Function, and Antigenicity: Implications for the Design of Spike-Based Vaccine Immunogens," Front Immunol., 11:576622 (12 pages).

ECDC (European Centre for Disease Prevention and Control) World Health Organization (Europe), 2021, "Methods for the detection and characterisation of SARS-CoV-2 variants—first update," Dec. 20, 2021 (13 pages).

ECDC (European Centre for Disease Prevention and Control) World Health Organization (Europe), 2021, "Methods for the detection and characterisation of SARS-CoV-2 variants—second update," Aug. 2, 2022 (14 pages).

ECDC (European Centre for Disease Prevention and Control) World Health Organization (Europe), 2021, "Methods for the detection and identification of SARS-CoV-2 variants," Mar. 2021 (7 pages).

Long et al., 2020, "Clinical and immunological assessment of asymptomatic SARS-CoV-2 infections," Nat. Med., 26(8):1200-1204 and Supplementary Materials (12 pages).

Lubinski et al., 2022, "Spike protein cleavage-activation mediated by the SARS-CoV-2 P681R mutation: a case-study from its first appearance in variant of interest (VOI) A.23.1 identified in Uganda," bioRxiv, 2021.06.30.450632 (27 pages).

Lv et al., 2020, "Cross-reactive antibody response between SARS-CoV-2 and SARS-CoV infections," bioRxiv, 2020.03.15.993097 (20 pages).

Lynn et al., 2015, "In vivo characterization of the physicochemical properties of polymer-linked TLR agonists that enhance vaccine immunogenicity," Nat. Biotechnol., 33(11):1201-1210.

Macgowan et al., 2020, "Missense variants in ACE2 are predicted to encourage and inhibit interaction with SARS-CoV-2 Spike and contribute to genetic risk in COVID-19," bioRxiv, 2020.05.03. 074781 (38 pages).

Madan et al., 2017, "Immunogenicity and safety of an AS03-adjuvanted H7N1 vaccine in adults 65years of age and older: A phase II, observer-blind, randomized, controlled trial," Vaccine, 35(15):1865-1872.

Mahase, 2022, "Omicron sub-lineage BA.2 may have "substantial growth advantage," UKHSA reports," BMJ, 376:o263.

Mantlo et al., 2019, "Differential Immune Responses to Hemorrhagic Fever-Causing Arenaviruses," Vaccines (Basel), 7(4):138 (16 pages).

Manuel Carreno et al., 2022, "Activity of convalescent and vaccine serum against SARS-CoV-2 Omicron," Nature, 602(7898):682-688 and Supplementary Materials (17 pages).

Margine et al., 2013, "Expression of functional recombinant hemagglutinin and neuraminidase proteins from the novel H7N9 influenza virus using the baculovirus expression system," J. Vis. Exp., (81):e51112 (10 pages).

Mathieu et al., 2020, "Coronavirus Pandemic (COVID-19)," OurWorldInData.org, [online]. [Retrieved on Oct. 8, 2023]. Retrieved from the Internet: <URL: https://ourworldindata.org/coronavirus> (45 pages).

Mulligan et al., 2020, "Phase I/II study of COVID-19 RNA vaccine BNT162b1 in adults," Nature, 586(7830):589-593.

Muramatsu et al., 2014, "Comparison of antiviral activity between IgA and IgG specific to influenza virus hemagglutinin: increased potential of IgA for heterosubtypic immunity," PLoS One, 9(1):e85582 (8 pages).

Murawski et al., "Newcastle disease virus-like particles containing respiratory syncytial virus G protein induced protection in BALB/c mice, with no evidence of immunopathology", J. Virol., 84(2):1110-1123 (2010).

Nachbagauer et al., 2016, "Age Dependence and Isotype Specificity of Influenza Virus Hemagglutinin Stalk-Reactive Antibodies in Humans," mBio, 7(1):e01996-15 (10 pages).

Nakaya et al., 2001, "Recombinant Newcastle disease virus as a vaccine vector," J. Virol., 75:11868-11873.

Nayak et al., 2008, "Molecular characterization and complete genome sequence of avian paramyxovirus type 4 prototype strain duck/Hong Kong/D3/75," Virol. J., 5:124 (11 pages).

Nayak et al., 2009, "Immunization of chickens with Newcastle disease virus expressing H5 hemagglutinin protects against highly pathogenic H5N1 avian influenza viruses," PLoS One, 4(8):e6509 (10 pages).

Nestola et al., 2015, "Improved virus purification processes for vaccines and gene therapy," Biotechnol. Bioeng., 112(5):843-857.

Nuhn et al., 2016, "pH-degradable imidazoquinoline-ligated nanogels for lymph node-focused immune activation" Proc. Natl. Acad. Sci. USA, 113(29):8098-8103.

Oestereich et al., 2016, "Efficacy of Favipiravir Alone and in Combination With Ribavirin in a Lethal, Immunocompetent Mouse Model of Lassa Fever," J. Infect. Dis., 213(6):934-938.

OIE Terrestrial Manual 2012, Chapter 2.3.14—Newcastle Disease (19 pages).

Okba et al., 2020, "Severe Acute Respiratory Syndrome Coronavirus 2-Specific Antibody Responses in Coronavirus Disease Patients," Emerg. Infect. Dis., 26(7):1478-1488.

(56) References Cited

OTHER PUBLICATIONS

Ou et al., 2020, "Characterization of spike glycoprotein of SARS-CoV-2 on virus entry and its immune cross-reactivity with SARS-CoV," Nat. Commun., 11(1):1620 (12 pages).

Palese et al., 1996, "Negative-strand RNA viruses: genetic engineering and applications," Proc. Natl. Acad. Sci. USA, 93(21):11354-11358.

Palese, 1995, "Genetic engineering of infectious negative-strand RNA viruses," Trends Microbiol., 3(4):123-125.

Pallesen et al., 2017, "Immunogenicity and structures of a rationally designed prefusion MERS-CoV spike antigen," Proc. Natl. Acad. Sci. USA, 114(35):E7348-E7357.

Park et al., "Newcastle disease virus V protein is a determinant of host range restriction," J. Virol., 77(17):9522-9532 (2003).

Park et al., 2006, "Engineered viral vaccine constructs with dual specificity: avian influenza and Newcastle disease," Proc. Natl. Acad. Sci. USA, 103(21):8203-8208.

Park et al., 2021, "Immunogenicity and Protective Efficacy of an Intranasal Live-attenuated Vaccine Against SARS-CoV-2 in Preclinical Animal Models," bioRxiv, 2021.01.08.425974 (51 pages).

Patent Cooperation Treaty, International Search Report for PCT/US2006/045859, dated Mar. 28, 2007.

Patent Cooperation Treaty, Written Opinion for PCT/US2006/045859, dated Mar. 28, 2007.

Pecora et al., 2002, "Phase I trial of intravenous administration of PV701, an oncolytic virus, in patients with advanced solid cancers," J. Clon. Oncol., 20:2251-2266.

Peeters et al., 1999, "Rescue of Newcastle disease virus from cloned cDNA: evidence that cleavability of the fusion protein is a major determinant for virulence," J. Virol., 73(6):5001-5009.

Peeters et al., 2001, "Generation of a recombinant chimeric Newcastle disease virus vaccine that allows serological differentiation between vaccinated and infected animals," Vaccine, 19:1616-1627.

Perdomo-Celis et al., 2019, "T-Cell Response to Viral Hemorrhagic Fevers," Vaccines (Basel), 7(1):11 (29 pages).

Pinto et al., 2020, "Cross-neutralization of SARS-CoV-2 by a human monoclonal SARS-CoV antibody," Nature, 583(7815):290-295 and Supplementary Materials (19 pages).

Pitisuttithum et al., 2021, "Safety and Immunogenicity of an Inactivated Recombinant Newcastle Disease Virus Vaccine Expressing SARS-CoV-2 Spike: Interim Results of a Randomised, Placebo-Controlled, Phase 1/2 Trial," medRxiv, 2021.09.17.21263758 (34 pages).

Pitisuttithum et al., 2022, "Safety and immunogenicity of an inactivated recombinant Newcastle disease virus vaccine expressing SARS-CoV-2 spike: Interim results of a randomised, placebo-controlled, phase 1 trial," eClinicalMedicine, 45:101323 (16 pages).

Planas et al., 2021, "Reduced sensitivity of SARS-CoV-2 variant Delta to antibody neutralization," Nature, 596(7871):276-280 and Supplementary Materials (20 pages).

Plotkin, 2010, "Correlates of protection induced by vaccination," Clin. Vaccine Immunol., 17(7):1055-1065.

Poh et al., 2020, "Two linear epitopes on the SARS-CoV-2 spike protein that elicit neutralising antibodies in COVID-19 patients," Nat. Commun., 11(1):2806 (7 pages).

Ponce-De-Leon et al., 2022, "Safety and immunogenicity of a live recombinant Newcastle disease virus-based COVID-19 vaccine (Patria) administered via the intramuscular or intranasal route: Interim results of a non-randomized open label phase I trial in Mexico," medRxiv, 2022.02.08.22270676 (28 pages).

Press Release, Antai, 2020, "The first in the world! CCIC Antai's exclusive product COVID-19 IgA/IgM/IgG antibody joint detection is emerging!," Mar. 25, 2020, in Chinese with machine English translation (19 pages).

Press Release, CNR, 2020, "The country's first single-use chemiluminescent novel coronavirus antibody detection kit was successfully developed and clinically tested in Shenzhen," Feb. 11, 2020, in Chinese with machine English translation (8 pages).

Press Release, Shenzhen Special Zone News, 2020, "Shenzhen Third People's Hospital issued another new coronavirus antibody test kit," Feb. 17, 2020, in Chinese with machine English translation (7 pages).

Press Release, Xinmin Evening News, 2020, "Rapid Testing Kit for the New Coronavirus IgM Antibody Jointly Developed by the Team of Academician Ge Junbo has passed Registration Test," Feb. 18, 2020, in Chinese with machine English translation (13 pages).

Qu et al., 2005, "Intranasal immunization with inactivated SARS-CoV (SARS-associated coronavirus) induced local and serum antibodies in mice," Vaccine, 23(7):924-931.

Rajendran et al., 2017, "Analysis of Anti-Influenza Virus Neuraminidase Antibodies in Children, Adults, and the Elderly by ELISA and Enzyme Inhibition: Evidence for Original Antigenic Sin," mBio, 8(2):e02281-16 (12 pages).

Reynolds et al., 1999, "A rapid virus neutralization assay for Newcastle disease virus with the swine testicular continuous cell line," Avian Dis., 43(3):564-571.

International Searching Authority, International Search Report and Written Opinion for International Patent Application No. PCT/US2023/065491 (Pub No. WO 2023196945) mailed Sep. 13, 2023 (15 pages).

Iwai et al., "PD-1 Inhibits Antiviral Immunity at the Effector Phase in the Liver," J. Exp. Med., 198(1):39-50 (2003).

Iwasaki et al., 2010, "Regulation of adaptive immunity by the innate immune system," Science, 327(5963):291-295.

Jackson et al., 2020, "An mRNA Vaccine against SARS-CoV-2—Preliminary Report," N. Engl. J. Med., 383(20):1920-1931.

Jaimes et al., 2020, "Structural modeling of 2019-novel coronavirus (nCoV) spike protein reveals a proteolytically sensitive activation loop as a distinguishing feature compared to SARS-CoV and related SARS like coronaviruses," bioRxiv, 2020.02.10.942185 (36 pages).

Jangra et al., 2021, "Sterilizing Immunity against SARS-CoV-2 Infection in Mice by a Single-Shot and Lipid Amphiphile Imidazoquinoline TLR7/8 Agonist-Adjuvanted Recombinant Spike Protein Vaccine," Angew Chem. Int. Ed. Engl., 60(17):9467-9473.

Jeyanathan et al., 2020, "Immunological considerations for COVID-19 vaccine strategies," Nat. Rev. Immunol., 20(10):615-632.

Jiang et al., 2020, "Neutralizing Antibodies against SARS-CoV-2 and Other Human Coronaviruses," Trends Immunol., 41(5):355-359.

Jilin Surge Medical Technology Co., Ltd., 2020, "Shuangzheng medical has successfully developed the Novel coronavirusIgG/IgM antibody detection kit," Feb. 17, 2020, in Chinese with machine English translation (9 pages).

Juraszek et al., 2021, "Stabilizing the closed SARS-CoV-2 spike trimer," Nat. Commun., 12(1):244 (8 pages).

Kanesa-Thasan et al., 2000, "Safety and immunogenicity of NYVAC-JEV and ALVAC-JEV attenuated recombinant Japanese encephalitis virus—poxvirus vaccines in vaccinia-nonimmune and vaccinia-immune humans," Vaccine, 19(4-5):483-491.

Kasturi et al., 2011, "Programming the magnitude and persistence of antibody responses with innate immunity," Nature, 470(7335):543-547 and Methods (8 pages).

Khan et al., 2020, "Analysis of Serologic Cross-Reactivity Between Common Human Coronaviruses and SARS-CoV-2 Using Coronavirus Antigen Microarray," bioRxiv, 2020.03.24.006544 (10 pages).

Khattar et al., "A Y526Q mutation in the Newcastle disease virus HN protein reduces its functional activities and attenuates virus replication and pathogenicity," J. Virol., 83:7779-7782 (2009).

Kim et al., 2016, "Newcastle Disease Virus as a Vaccine Vector for Development of Human and Veterinary Vaccines," Viruses, 8(7):183 (15 pages).

Kirchdoerfer et al., 2016, "Pre-fusion structure of a human coronavirus spike protein," Nature, 531(7592):118-121.

Kirchdoerfer et al., 2018, "Stabilized coronavirus spikes are resistant to conformational changes induced by receptor recognition or proteolysis," Sci. Rep., 8(1): 15701 and Publisher Correction, Sci. Rep., 8(1):17823 (12 pages).

Koch et al., 2020, "Safety and immunogenicity of a modified vaccinia virus Ankara vector vaccine candidate for Middle East respiratory syndrome: an open-label, phase 1 trial," Lancet Infect. Dis., 20(7):827-838.

(56) References Cited

OTHER PUBLICATIONS

Krammer et al., 2012, "A carboxy-terminal trimerization domain stabilizes conformational epitopes on the stalk domain of soluble recombinant hemagglutinin substrates," PLoS One, 7(8):e43603 (10 pages).

Krammer et al., 2020, "Meeting report and review: Immunological assays and correlates of protection for next-generation influenza vaccines," Influenza Other Respir. Viruses, 14(2):237-243 (Epub 2019).

Krammer et al., 2020, "Serology assays to manage COVID-19," Science, 368(6495):1060-1061.

Krammer, 2020, "SARS-CoV-2 vaccines in development," Nature, 586(7830):516-527.

Krause et al., 2021, "Considerations in boosting COVID-19 vaccine immune responses," Lancet, 398(10308):1377-1380 and Supplementary Appendix (15 pages).

Krishnamurthy et al., 2000, "Recovery of a Virulent Strain of Newcastle Disease Virus from Cloned cDNA: Expression of a Foreign Gene Results in Growth Retardation and Attenuation," Virology, 278:168-182.

Kuai et al., 2017, "Designer vaccine nanodiscs for personalized cancer immunotherapy," Nat. Mater, 16(4):489-496 and Methods (10 pages).

Lalonde et al., 2017, "Therapeutic glycoprotein production in mammalian cells," J. Biotechnol., 251:128-140.

Lamb et al., 1996, "Chapter 20—Paramyxoviridae: The Viruses and Their Replication," in Fundamental Virology, Third Edition, edited by Fields et al., Philadelphia, PA, pp. 577-604.

Lamers et al., 2020, "SARS-CoV-2 productively infects human gut enterocytes," Science, 369(6499):50-54.

Langley et al., 2015, "Immunogenicity and Reactogenicity of an Inactivated Quadrivalent Influenza Vaccine Administered Intramuscularly to Children 6 to 35 Months of Age in 2012-2013: A Randomized, Double-Blind, Controlled, Multicenter, Multicountry, Clinical Trial," J. Pediatric Infect. Dis. Soc., 4(3):242-251 (Epub 2014).

Lara-Puente et al., 2021, "Safety and Immunogenicity of a Newcastle Disease Virus Vector-Based SARS-CoV-2 Vaccine Candidate, AVX/COVID-12-HEXAPRO (Patria), in Pigs," mBio, 12(5):e0190821 (16 pages).

Letko et al., 2020, "Functional assessment of cell entry and receptor usage for SARS-CoV-2 and other lineage B betacoronaviruses," Nat. Microbiol., 5(4):562-569 and Supplementary Materials (17 pages).

Li et al., 2005, "Decreased dependence on receptor recognition for the fusion promotion activity of L289A-mutated newcastle disease virus fusion protein correlates with a monoclonal antibody-detected conformational change," J. Virol., 79(2):1180-1190.

Li et al., 2005, "Structure of SARS coronavirus spike receptor-binding domain complexed with receptor," Science, 309(5742):1864-1868.

Li et al., 2020, "Early Transmission Dynamics in Wuhan, China, of Novel Coronavirus-Infected Pneumonia," N. Engl. J. Med., 382(13):1199-1207.

Li et al., 2020, "Effect of Convalescent Plasma Therapy on Time to Clinical Improvement in Patients With Severe and Life-threatening COVID-19: A Randomized Clinical Trial," JAMA, 324(5):460-470.

Li et al., 2020, "Single-Dose, Intranasal Immunization with Recombinant Parainfluenza Virus 5 Expressing Middle East Respiratory Syndrome Coronavirus (MERS-CoV) Spike Protein Protects Mice from Fatal MERS-CoV Infection," mBio., 11(2):e00554-20 (12 pages).

Li et al., 2022, "Omicron and S-gene target failure cases in the highest COVID-19 case rate region in Canada—Dec. 2021," J. Med. Virol., 94(5):1784-1786.

Lienenklaus et al., 2009, "Novel reporter mouse reveals constitutive and inflammatory expression of IFN-beta in vivo," J. Immunol., 183(5):3229-3236.

Liniger et al., 2008, "Induction of neutralising antibodies and cellular immune responses against SARS coronavirus by recombinant measles viruses," Vaccine, 26(17):2164-2174.

Liu et al., 2005, "Adenoviral expression of a truncated S1 subunit of SARS-CoV spike protein results in specific humoral immune responses against SARS-CoV in rats," Virus Res., 112(1-2):24-31.

Liu et al., 2006, "Two-year prospective study of the humoral immune response of patients with severe acute respiratory syndrome," J. Infect. Dis., 193(6):792-795.

Liu et al., 2011, "Epithelial cells lining salivary gland ducts are early target cells of severe acute respiratory syndrome coronavirus infection in the upper respiratory tracts of rhesus macaques," J. Virol., 85(8):4025-4030.

Liu et al., 2014, "Structure-based programming of lymph-node targeting in molecular vaccines," Nature, 507(7493):519-522 and Supplementary Materials (15 pages).

Liu et al., 2017, "Newcastle disease virus-based MERS-CoV candidate vaccine elicits high-level and lasting neutralizing antibodies in Bactrian camels," J. Integr. Agric., 16(10):2264-2273.

Liu et al., 2020, "Convalescent plasma treatment of severe COVID-19: A matched control study," medRxiv, 2020.05.20.20102236 (22 pages).

Liu et al., 2020, "High neutralizing antibody titer in intensive care unit patients with COVID-19," Emerg. Microbes. Infect., 9(1):1664-1670.

Liu et al., 2021, "Delta spike P681R mutation enhances SARS-CoV-2 fitness over Alpha variant," bioRxiv, 2021.08.12.456173 (29 pages).

Liu et al., 2021, "Reduced neutralization of SARS-CoV-2 B.1.617 by vaccine and convalescent serum," Cell, 184(16):4220-4236.e13 (31 pages).

Livak et al., 2001, "Analysis of relative gene expression data using real-time quantitative PCR and the 2(-Delta Delta C(T)) Method" Methods, 25(4):402-408.

Long et al., 2020, "Antibody responses to SARS-CoV-2 in patients with COVID-19," Nat. Med., 26(6):845-848.

* cited by examiner

RECOMBINANT VACCINE AGAINST COVID-19 BASED ON A PARAMYXOVIRUS VIRAL VECTOR

CROSS-REFERENCE TO RELATED APPLICATIONS

This application is a National Stage of International Patent Application No. PCT/IB2021/051491, filed 22 Feb. 2021, titled RECOMBINANT VACCINE AGAINST COVID-19 BASED ON A PARAMYXOVIRUS VIRAL VECTOR, published as International Patent Application Publication No. WO 2021/229311 A1, which claims the benefit of, and priority to, International Patent Application No. PCT/IB2020/054545, filed 13 May 2020, each of which is incorporated by reference herein in its entirety for all purposes.

INCORPORATION BY REFERENCE

In compliance with 37 C.F.R. § 1.52 (e), the sequence information contained in electronic file name SEQUENCE LISTING-LOZANO6.txt, which was created on 22 Feb. 2021 and 103 KB, is hereby incorporated by reference herein in its entirety.

FIELD OF THE INVENTION

The present invention is related to techniques used in the prevention and control of the coronavirus disease 2019 (COVID-19), and more particularly it is related to a recombinant viral vector vaccine that has inserted an exogenous nucleotide sequence encoding proteins with antigenic activity against severe acute respiratory syndrome coronavirus 2 (SARS-COV-2), and a pharmaceutically acceptable carrier, adjuvant and/or excipient.

BACKGROUND OF THE INVENTION

Coronaviruses (CoVs) are a family of viruses that cause the common cold and serious diseases such as Middle East Respiratory Syndrome (MERS-COV) and Severe Acute Respiratory Syndrome (SARS-COV). The Severe Acute Respiratory Syndrome Coronavirus 2 (SARS-COV-2) is the etiologic agent of the coronavirus disease 2019 (COVID-19) outbreak, which began in December 2019 in Wuhan, China. On Mar. 11, 2020, the World Health Organization (WHO) declared COVID-19 as a pandemic.

Currently there are no drugs or vaccines available to treat COVID-19, and a significant number of deaths have been reported primarily in elderly patients with comorbidities. By May 4, 2020, there were more than 3.4 million cases reported worldwide, with more than 239 thousand deaths, which continue increasing, primarily in Europe and the United States, which are countries with a larger part of elderly population who have acquired the infection. To date, the only effective measure to counteract the spread of COVID-19 consists of isolating the population, quarantining infected people, suspending most of the commercial activities and businesses, along with intensive clinical therapy for patients with severe symptoms. However, the adoption of such containment measures has dramatically impacted the economy of all the countries that today are fighting this pandemic.

In the way to finding a solution against this emerging infectious disease, the vectorized vaccines provide an approach of active (live) vaccine not involving the whole pathogen. According to information from the WHO website consulted on May 4, 2020), some institutions and pharmaceutical companies are developing recombinant vaccines against COVID-19 based on vectors of human adenovirus, MVA, VSV and measles, among others. In this regard, previously in the case of the SARS-COV virus, several vectorized vaccines were described with these vectors. However, one group found that ferrets immunized with an MVA/SARS-COV vaccine developed hepatitis (CZUB, Markus, et al. Evaluation of modified vaccinia virus Ankara based recombinant SARS vaccine in ferrets, *Vaccine*, 2005, vol. 23, no. 17-18, p. 2273-2279). Vaccine constructs against SARS-COV based on the replication of a defective type 5 human adenovirus expressing a partial or complete spike glycoprotein S of SARS-COV have been evaluated for their immunogenicity in rats and monkeys (LIU, Ran-Yi, et al., Adenoviral expression of a truncated S1 subunit of SARS-COV spike protein results in specific humoral immune responses against SARS-COV in rats. *Virus Research,* 2005, vol. 112, no. 1-2, p. 24-31; and GAO, Wentao, et al., "Effects of a SARS-associated coronavirus vaccine in monkeys". *The Lancet,* 2003, vol. 362, no. 9399, p. 1895-1896), but immunization depends on a high dose of vaccine, and safety and protective efficacy have not been demonstrated. Also has been described an attenuated version of the type 3 human parainfluenza virus, a common pediatric respiratory pathogen, for expressing the SARS-COV spike glycoprotein, which demonstrated that a single intranasal and intratracheal inoculation was immunogenic and protective against SARS-COV on a challenge in hamsters and African green monkeys (BISHT, Himani, et al., Severe acute syndrome respiratory coronavirus spike protein Expressed by attenuated vaccinia virus protectively immunizes mice, *Proceedings of the National Academy of Sciences,* 2004 vol. 101, no. 17, p. 6641-6646). However, a concern about any vector based on a common pathogen is that the adult population has significant immunity facing previous exposure that will restrict infection and replication of the viral vector and reduce its immunogenicity. Indeed, comparisons of immunogenicity of vaccines vectorized with vaccinia virus and those of vectors with type 5 human adenovirus in rodents, non-human primates, and humans demonstrated that pre-existing immunity to the vector greatly reduced the immunogenicity of these vaccines (KANESA-THASAN, Niranjan, et al. Safety and immunogenicity of NYVAC-JEV and ALVAC-JEV attenuated recombinant Japanese encephalitis virus-poxvirus vaccines in vaccinia-nonimmune and vacciniaimmune humans. *Vaccine,* 2000, vol. 19, no. 4-5, p. 483-491; SHARPE, Sally, et al. Induction of simian immunodeficiency virus (SIV)-specific CTL in rhesus macaques by vaccination with modified vaccinia virus Ankara expressing SIV transgenes: influence of pre-existing anti-vector immunity. *Journal of General Virology,* 2001, vol. 82, no. 9, p. 2215-2223; and ZHI, Yan, et al. Efficacy of severe acute respiratory syndrome vaccine based on a nonhuman primate adenovirus in the presence of immunity against human adenovirus. *Human gene therapy,* 2006, vol. 17, no. 5, p. 500-506).

On the other hand, the Newcastle disease virus (NDV) has been described as a vector that can potentially be used to develop vaccine vectors for humans, for example in patent documents WO2011059334, U.S. Pat. No. 9,476,033 or U.S. Pat. No. 10,308,913. NDV is an unsegmented negative strand RNA virus of the Paramyxoviridae family and its natural hosts are birds whereby is antigenically distinct from common human pathogens. The group of DiNapoli et al., 2007 (DINAPOLI, Joshua M., et al., Newcastle disease virus, a host range-restricted virus, as a vaccine vector for intranasal immunization against emerging pathogens, *Proceedings of the National Academy of Sciences,* 2007, vol. 104, no. 23, p. 9788-9793.) evaluated an NDV expressing the SARS-COV spike glycoprotein S as a topical vector of respiratory vaccine, with SARS-COV as the target pathogen by direct analysis of nasal and lung tissues collected by necropsy at the peak of SARS-COV replication. It was found that African green monkeys immunized through the respiratory tract with two doses of this vaccine developed a neutralizing antibody titer of SARS-COV comparable to the secondary response observed in animals that were immunized with an experimental vaccine different from SARS-COV and challenged with SARS-COV. When animals immunized with NDV expressing spike glycoprotein S were challenged with a high dose of SARS-COV, the direct viral analysis of lung tissues taken by necropsy at the peak of viral replication showed an average reduction of 236 or 1,102 times in the lung titer of SARS-COV compared to control animals.

Notwithstanding the above, the SARS-COV spike glycoprotein S presents important differences with that of SARS-COV-2 (WALLS, Alexandra C., et al. Structure, function, and antigenicity of the SARS-COV-2 spike glycoprotein. Cell, 2020). Spike glycoproteins(S) of coronavirus promote the entry into cells and are the primary target of antibodies. According to Wall et al., 2020, the SARS-COV-2 spike glycoprotein S harbors a furin cleavage site at the boundary between the S1/S2 subunits, which is processed during biogenesis and significantly differentiates this virus from SARS-COV and SARS-related coronaviruses. It is the first time that a coronavirus with a polybasic cleavage site for a protease is described. In addition, the spike glycoprotein S has a metastable prefusion conformation which becomes into a highly stable post fusion conformation, which facilitates the fusion of membrane but makes it very difficult to produce recombinantly. In this way, it is not possible to know or deduce whether a recombinant vectorized vaccine against COVID-19 based on NDV or some other virus will be effective for the treatment or prevention of COVID-19, and whether the construct of a viral vector that includes the SARS-COV-2 spike glycoprotein S will be stable, i.e. not lose the ability to replicate after several consecutives passages in cell lines to achieve a viral titer suitable for the manufacture of a vaccine on an industrial scale.

Moreover, for a recombinant vaccine has not been determined the most effective way to insert the SARS-COV-2 genes so as to produce an immune response that allows control of the pandemic, far less in a Newcastle virus vector.

Therefore, it is absolutely necessary to develop a vaccine against COVID-19 that provides a sufficient level of protection for an effective control of the current pandemic.

OBJECTS OF THE INVENTION

Taking into account the shortcomings of the prior art, it is an object of the present invention to provide a recombinant paramyxovirus viral vector vaccine against coronavirus disease 2019 (COVID-19) that is effective.

It is another object of the present invention to provide the use of a recombinant paramyxovirus viral vector vaccine to control COVID-19.

It is a further object of the present invention to provide a construct of paramyxovirus viral vector having inserted an exogenous nucleotide sequence encoding for proteins with antigenic activity against the acute respiratory syndrome coronavirus 2 (SARS-COV-2), which is stable after being subjected to consecutive passages in a cell line.

These and other objects are attained by a recombinant paramyxovirus viral vector vaccine against COVID-19 according to the present invention.

BRIEF DESCRIPTION OF THE INVENTION

For this, a recombinant vaccine has been invented that comprises a viral vector based on Newcastle disease virus having inserted an exogenous nucleotide sequence of severe acute respiratory syndrome coronavirus 2 (SARS-COV-2), capable of generating a cellular immune response, and a pharmaceutically acceptable carrier, adjuvant, and/or excipient.

DETAILED DESCRIPTION OF THE INVENTION

During development of the present invention, it has been unexpectedly found that a recombinant vaccine comprising a paramyxovirus viral vector capable of generating a cellular immune response, having inserted an exogenous nucleotide sequence encoding for antigenic sites of syndrome acute respiratory disease coronavirus 2 (SARS-COV-2), and a pharmaceutically acceptable carrier, adjuvant and/or excipient, provides a suitable protection against coronavirus disease 2019 (COVID-19).

The used viral vector can be active (live) or inactivated (dead), by inactivated being understood that the recombinant virus that functions as a viral vector and contains the nucleotide sequence encoding for antigenic sites of SARS-COV-2 has lost the property of replicate. Inactivation is achieved by physical or chemical procedures well known in the art, preferably by chemical inactivation with formaldehyde or beta-propiolactone (Office International des Epizooties 2008, Newcastle Disease. OIE Manual of Diagnostic Tests and Vaccines for Terrestrial Animals. Office International des Epizooties, France, p. 576-589). On the other hand, it is understood that an active or live virus maintains its ability to replicate.

Preferably, the used viral vector is a paramyxovirus which is selected from any paramyxovirus including any serotype, genotype or genetic class, including lentogenic, mesogenic and velogenic viruses. Likewise, it is preferred to use paramyxoviruses to which reverse genetic techniques can be performed to eliminate phenylalanine in position 117 and the basic amino acids in position close to position Q114 that give pathogenicity to paramyxoviruses, or paramyxoviruses included in the genus Avulavirus that infect birds, such as Newcastle disease virus (NDV) or Sendai virus. More preferably, the viral vector is NDV and said viral vector is preferably selected from lentogenic or mesogenic strains, such as LaSota, B1, QV4, Ulster, Roakin, Komarov strains, Preferably, the recombinant virus is from LaSota strain. Even more preferably, the NDV viral vector comprises SEQ ID NO:6 or SEQ ID NO:14.

With regard to the exogenous nucleotide sequence encoding for antigenic sites of SARS-COV-2, in the case of the present invention the used nucleotide sequence is preferably selected from a sequence encoding the SARS-COV-2 spike glycoprotein S or a sequence encoding a sequence derived thereof. The SARS-COV-2 spike glycoprotein S comprises two functional subunits responsible for binding to the host cell receptor (S1 subunit) and fusion of viral and cellular membranes (S2 subunit). In a preferred embodiment of the invention, the exogenous nucleotide sequence encoding for antigenic sites of SARS-COV-2 is selected from a sequence encoding the S1 subunit of SARS-COV-2 spike glycoprotein S, a sequence encoding the S2 subunit of SARS-COV-2 spike glycoprotein S, a sequence encoding the two of S1 and S2 subunits of SARS-COV-2 spike glycoprotein S, a sequence encoding at least one fragment of S1 or S2 subunits of SARS-Cov-2 spike glycoprotein S, a sequence having at least 80% of identity with the sequence encoding the S1 subunit of SARS-Cov-2 spike glycoprotein S, a sequence having at least 80% of identity with the sequence encoding the S2 subunit of SARS-COV-2 spike glycoprotein S, a sequence having at least 80% of identity with the sequence encoding the two of S1 and S2 subunits of SARS-COV-2 spike glycoprotein S, a sequence having at least 80% of identity with a sequence encoding at least one fragment of S1 or S2 subunits of SARS-CoV-2 spike glycoprotein S, a sequence encoding the two of S1 and S2 subunits of SARS-COV-2 spike glycoprotein S lacking of at least one epitope located between nucleotides corresponding to amino acids 1 to 460 of the sequence of S1, a sequence encoding the S1 subunit of SARS-COV-2 spike glycoprotein S lacking of at least one epitope located between nucleotides corresponding to amino acids 1 to 460 of the sequence of S1, or a sequence encoding the two of S1 and S2 subunits of SARS-CoV-2 spike glycoprotein S, stabilized in its prefusion form by including at least two substitutions of proline in S2 subunit. In a preferred embodiment, the epitope located between nucleotides corresponding to amino acids 1 to 460 of the sequence of S1 is selected from amino acid sequences SEQ ID NO:7, SEQ ID NO:8, SEQ ID NO:9 or SEQ ID NO:10. In other preferred embodiment, the exogenous nucleotide sequence encoding for antigenic sites of SARS-COV-2 is selected from a sequence with an identity of at least 80% with any of the sequences SEQ ID NO:1, SEQ ID NO:2, SEQ ID NO: 3, SEQ ID NO:4 or SEQ ID NO:5. In a further preferred embodiment, the sequence encoding the two of S1 and S2 subunits of SARS-COV-2 spike glycoprotein S stabilized in its prefusion form by including at least two substitutions of proline in S2 subunit, is selected from a sequence having at least 80% of identity with any sequence that translates into any of the amino acid sequences SEQ ID NO:11, SEQ ID NO:12 or SEQ ID NO:13.

The exogenous nucleotide sequence encoding the antigenic sites of SARS-COV-2 of the vaccine of the present invention can be prepared by chemical synthesis of the nucleotide sequence of interest so that it can subsequently be inserted into the NDV viral vector. The insertion of the exogenous nucleotide sequence is carried out using standard cloning techniques of molecular biology and can be inserted into any intergenic regions of NDV genome. The thus produced infectious clone is transfected into a cell culture for generating recombinant virus or parent virus.

The virus replicates through consecutive passages in any system suitable for growing, such as SPF chicken embryo, or commercial cell lines or expressly designed for growing of viruses, until reaching the concentration of the virus that is required to achieve the antigenic response, preferably between $10^{6.0}$ and $10^{10.0}$ CEID50% (Chicken Embryo Infectious Dose 50%)/mL. It is preferred that the virus be stable after at least three consecutive passages in the system used for growth once rescued from the cell culture, so that a stable production is achieved on an industrial scale. For virus isolation, the virus is removed from the system appropriate for growing and is separated from cellular or other components, typically by well-known clarification procedures such as filtration, ultrafiltration, gradient centrifugation, ultracentrifugation, and column chromatography, and can be further purified as desired using well known procedures, e.g., plaque assays.

In the embodiment in which the vaccine is active, it is a natural lentogenic active vaccine virus or one attenuated by methods already known in the art. On the other hand, when the vaccine is inactivated, once the viral concentration required to achieve the antigenic response has been reached, the virus is inactivated. Preferably, the inactivation is carried out by physical or chemical procedures well known in the art, preferably by chemical inactivation with formaldehyde, beta-propiolactone or binary ethyleneimine (BEI).

Pharmaceutically acceptable carriers for the vaccines of the present invention are preferably aqueous solutions or emulsions. More particularly, in the case of active virus vaccines aqueous solutions are preferred, and in the case of inactivated vaccines preferably the used carrier is compatible with an immune adjuvant used to enhance the immune response to the inactivated vaccine. In a further embodiment in which the vaccine is inactivated, the vaccine is preferably accompanied by a pharmaceutically acceptable adjuvant. In an embodiment in which an adjuvant is used, adjuvants based on squalenes are preferred; preferably those referred as MF-59® or AddaVax® or AS03®, TLR-9 receptor agonists, such as CpG-1018, or cationic lipids such as R-DO-TAP.

Regarding the administration of the vaccine, it can be administered intramuscularly, intranasally, subcutaneously, by spraying or nebulization, using the appropriate means and forms for each case and depending on whether it is an active vaccine or an inactivated vaccine. Preferably, the vaccine administration is carried out at least once intramuscularly and/or intranasally.

In a particularly preferred embodiment, the vaccine is administered at least twice to generate a higher immune response, either by maintaining the route of administration or changing the route of administration, with a virus concentration preferably between $10^{6.0}$ and $10^{8.5}$ CEID50%/mL per dose, according to the volume of vaccine to be applied according to the selected route of administration. Preferably the vaccine is administered twice intramuscularly either in active or inactivated form, twice intranasally in its active form, or once intranasally, followed by once intramuscularly. Administration of vaccines in an embodiment which is administered twice, can be carried out within a period of 7 to 35 days between the first and second administration, preferably within a period of 14 to 28 days between the first and second administration, and more preferably it is administered the first time by intranasal route in its active form and the second time by intramuscular route, either in its active or inactivated form.

In another aspect of the present invention, it has been found that it is possible to administer intranasally a dose of an active virus comprising antigenic sites of the severe acute respiratory syndrome coronavirus 2 (SARS-COV-2), preferably the recombinant paramyxovirus of the present invention, followed by a second intramuscular dose of a SARS-COV-2 antigen, achieving a highly efficient immune response. Preferably, the antigen of the second dose is the same active virus of the first dose, but once the immunization has been carried out by intranasal route, a skilled in the art can infer that it is possible to deliver intramuscularly any other SARS-COV-2 antigen. Still more preferably, the antigen of the second dose is the same virus of the first dose in its inactivated form.

Preferably, the vaccine of the present invention is formulated with a volume of 0.5 mL per dose that contains the virus concentration corresponding to its intramuscular application, either in its active or inactivated form. In an embodiment where the route of administration is intranasal, the preferred volume per dose is 0.2 mL.

The vaccine according to the principles of the present invention, additionally, does not cause adverse events in mammals.

The present invention will be better understood from the following examples, which are presented only for illustrative purposes to allow a thorough understanding of the preferred embodiments of the present invention, not implying that there are no other, non-illustrated embodiments that may be implemented based on the above detailed description.

Example 1

Generation of NDV LaSota Vectors

To clone the RNA genome of NDV strain LaSota and thus generate a viral vector in the form of plasmid DNA referred as pLS11801140 (SEQ ID NO:6), firstly extraction of total viral RNA from NDV strain LaSota was carried out by triazole method. From the purified RNA, the synthesis of cDNA (complementary DNA) of the viral genome was carried out, using the previously purified total RNA as a template. In order to clone all of the genes of NDV genome (15,183 base pairs (bp)), 7 fragments with "overlapping" ends and cohesive restriction sites were amplified by PCR. Fragment 1 (F1) spans from nucleotide (nt) 1-1755, F2 goes from nt 1-3321, F3 comprises from nt 1755-6580, F4 goes from 6,151-10,210, F5 spans from nt 7,381-11,351, F6 goes from 11,351-14,995 and F7 comprises from nt 14,701-15, 186. The 7 fragments were assembled within the cloning vector referred as pLS11801140 (SEQ ID NO:6) using standard ligation techniques, which allowed reconstruct the NDV LaSota genome, which after cloning contains a unique SacII restriction site between the P and M genes, which serves for cloning of any gene of interest in this viral region of the vector. In addition, another vector referred as pLS11801140_L289A (SEQ ID NO:14) was generated, for which the same process above described for pLS11801140 was followed, but including the amino acid L289A in the F gene of the NDV genome.

Example 2

Cloning of Various Exogenous Nucleotide Sequences of SARS-COV-2 in SacII Site of Vector pNDVLS11801140

To clone various exogenous nucleotide sequences derived from the SARS-COV-2 spike glycoprotein S, the following 6 versions of the SARS-COV-2 spike glycoprotein S gene were assembled in silico using the software Vector NTI®, based on the Wuhan-Hu-1 strain (accession number NC_045512.2):

Spike S1/S2 SARS-COV-2: Sequence of SARS-COV-2 spike glycoprotein S (with S1 and S2 subunits) not modified (SEQ ID NO:1).

Spike S1 SARS-COV-2/TMCyto: Sequence of S1 subunit of SARS-COV-2 spike glycoprotein S fused to the transmembrane and cytoplasmic sequence (TMCyto) of F gene of NDV (SEQ ID NO:2).

Spike S1/S2 SARS-COV-2/TMCyto: Sequence of ectodomain of SARS-COV-2 spike glycoprotein S fused to the transmembrane and cytoplasmic sequence (TMCyto) of F gene of NDV (SEQ ID NO:3).

Spike S1/S2 SARS-COV-2/PreF: Sequence of ectodomain of SARS-COV-2 spike glycoprotein S fused to the transmembrane and cytoplasmic sequence (TMCyto) of F gene of NDV, modified so that the NDV protein F acquired the pre-fusion conformation. The cleavage site of spike glycoprotein S was mutated from RRAR to A and 2 mutations of proline were introduced in amino acids K986P and V987P (SEQ ID NO:4).

Spike S1/S2 SARS-COV-2/PreF/-ADE: Sequence of ectodomain of SARS-COV-2 spike glycoprotein S fused to the transmembrane and cytoplasmic sequence (TMCyto) of F gene of NDV, modified so that the NDV protein F acquired the pre-fusion conformation and avoid antibody dependent infection (ADE) amplification. The cleavage site of spike glycoprotein S was mutated from RRAR to A and 2 mutations of proline were introduced in amino acids K986P and V987P, and a deletion of the epitope corresponding to amino acids located in positions 363 to 368 was synthetically introduced (SEQ ID NO:5).

Spike S1/S2 SARS-COV-2/Hexapro: Sequence of ectodomain of SARS-COV-2 spike glycoprotein S stabilized in its prefusion form and four additional prolines distributed in the synthetic gene to give greater stability to spike protein expressed by NDV (SEQ ID NO:11).

The above sequences were initially independently cloned into a pUC vector. The pUC inserts were then subcloned by standard genetic engineering techniques into the unique restriction site SacII, located between the P and M genes of genome of NDV LaSota contained in the plasmid pLS11801140 (SEQ ID NO:6). The plasmid pLS11801140 (SEQ ID NO:6) also contains all the transcription and translation signal sequences so that each of the five versions of the genes can be transcribed and translated and thus generate 6 different versions of the SARS-COV-2 spike glycoprotein S. As a result of the cloning process six NDV DNA. (complementary DNA) clones were generated, referred as, respectively:

pNDVLS/Spike S1/S2 SARS-Cov-2.

pNDVLS/Spike S1 SARS-COV-2/TMCyto.

pNDVLS/Spike S1/S2 SARS-COV-2/TMCyto.

pNDVLS/Spike S1/S2 SARS-COV-2/PreF.

pNDVLS/Spike S1/S2 SARS-COV-2/PreF/-ADE.

pNDVLS/Spike S1/S2 SARS-COV-2/Hexapro.

Each of the generated plasmids was characterized by PCR to detect the presence of each version of the SARS-COV-2 spike glycoprotein S. They were also characterized by restriction enzyme digestion, obtaining the expected restriction patterns. Stability and sequence of the PCR product of each version of SARS-COV-2 spike glycoprotein S were confirmed by sequencing.

Example 4

Generation of Recombinant Viruses

Each of the plasmids generated in the above example was transformed by a chemical method and then was independently propagated in E. coli for 16 hours under continuous stirring at 37° C. DNA of each clone was purified by standard molecular biology procedures. Ten micrograms (μg) of purified DNA were used in transfection experiments by using lipofectamine in Hep2 and A-549 cells. Forty-eight hours after transfection, each of the recombinant viruses generated from the 6 transfections was recovered from the supernatant and used in viral propagation assays in specific pathogen-free (SPF) embryonated chicken eggs for the subsequent preparation of the vaccines.

Example 5

Propagation of Recombinant Viruses

SPF embryonated chicken eggs were inoculated with the production seeds, with the infecting dose previously determined for each of the recombinant viruses prepared in the previous example. The embryos were incubated at 37° C. for a period of 48 hours, checking mortality daily. After this period, the live embryos were refrigerated from one day to the next, preferably for 24 hours; the amnio-allantoic fluid (FAA) was harvested under aseptic conditions and clarified by centrifugation. The FAA was used to characterize by hemagglutination the generation of recombinant virus rescued from the *E. coli* cellular culture and by RT-PCR, using specific primers to amplify the sequence located between the P and M genes, and demonstrate the presence of the various versions of the SARS-COV-2 spike glycoprotein S cloned in each of the recovered recombinant viruses. Once the identity was established by RT-PCR, the stability of the various inserts was established by sequencing each of them. From the transfection and propagation assays in SPF chicken embryonated eggs, the following 6 recombinant viruses were generated:

rNDVLS/Spike S1/S2 SARS-Cov-2.
rNDVLS/Spike S1 SARS-COV-2/TMCyto.
rNDVLS/Spike S1/S2 SARS-COV-2/TMCyto.
rNDVLS/Spike S1/S2 SARS-COV-2/PreF.
rNDVLS/Spike S1/S2 SARS-COV-2/PreF/-ADE.
rNDVLS/Spike S1/S2 SARS-COV-2/Hexapro.

Example 6

Manufacture of Active and Inactivated Vaccines Against COVID-19

The viruses prepared in the previous example were purified from FAA as previously described in the art (SANTRY, Lisa A., et al. Production and purification of high-titer Newcastle disease virus for use in preclinical mouse models of cancer. *Molecular Therapy—Methods & Clinical Development,* 2018, vol. 9, p. 181-191; and NESTOLA, Piergiuseppe, et al. Improved virus purification processes for vaccines and gene therapy. *Biotechnology and Bioengineering,* 2015, vol. 112, no. 5, p. 843-857.).

The active vaccines were prepared to be administered by intramuscular and intranasal routes in aqueous solution. For this, the FAA was mixed with a stabilizing solution (TPG) so that three vaccines were obtained with four different concentrations depending on the volume required to be applied in the vaccine: providing a minimum of $10^{7.0}$ CEID50%/mL per dose, providing a minimum of $10^{7.5}$ CEID50%/mL per dose, providing a minimum of $10^{8.0}$ CEID50%/mL per dose, and providing a minimum of $10^{8.5}$ CEID50%/mL per dose.

Table 1 shows the composition of 1 L of TPG stabilizing solution.

TABLE 1

| Component | Amount |
| --- | --- |
| Trehalose Dihydrate | 75.0 g |
| Dibasic Sodium Phosphate | 1.30 g |
| Monobasic Potassium Phosphate | 0.50 g |
| Monosodium glutamate | 0.90 g |
| Water for injection | 1,000 mL |

Similarly, viruses purified with the same technique used for active vaccines were inactivated by chemical inactivation with a 10% formaldehyde solution in PBS added dropwise, and a water-oil-water type emulsion was made as an adjuvant to perform a test on pigs. The oil phase corresponds to 25% of formulation, the internal aqueous phase to 25% of formulation, and the external aqueous phase to 50% of formulation. Sterile purified water and Span 80 and Tween 80 type surfactants were used for preparing the aqueous phase. Mineral oil and Span 80 and Tween 80 type surfactants were used for preparing the oily phase. Thus, four vaccines with four different concentrations were obtained: providing a minimum of $10^{7.0}$ CEID50%/mL per dose, providing a minimum of $10^{7.5}$ CEID50%/mL per dose, providing a minimum of $10^{8.0}$ CEID50%/mL per dose, and providing a minimum of $10^{8.5}$ CEID50%/mL per dose. To make the emulsion, the aqueous phase was slowly added to the oil phase under constant stirring. To achieve the specified particle size a homogenizer was used.

Example 7

Stability Tests of Constructs in Consecutive Passages

Example 7A—Stabilization of Protein S (Spike) with Two Prolines

Two of the constructs made according to example 5 were subjected to consecutive passages in SPF embryos as described in such example 5, and the recovered viruses were tested to confirm their stability and identity, particularly with regard to the obtained viral titer and permanency and integrity of the inserted SARS-COV-2 antigen.

The construct of example 5 referred as rNDVLS/Spike S1/S2 SARS-COV-2/PreF comprises the gene ectodomain, which will be fused to the Transmembrane and Cytoplasmic region (TMC or TMCyto) of the F (Fusion) gene of Newcastle virus. This fusion ensures that the Spike protein encoded by this chimeric gene (Ectodomain+TMCyto), is incorporated into the Newcastle capsid and is exposed on the viral surface as the main antigen. The nucleotide sequence of the chimeric gene in this version has codon usage optimized for human. The cleavage site for Furin (F) was removed and two prolines were introduced to the sequence to ensure the pre-fusion structure of the final protein.

According to literature and previous studies based on the SARS-COV virus, this structure with two prolines is able to stabilize the structure of the Spike protein for generating antibodies with the correct conformation to neutralize SARS-COV-2 virus.

Once generated, the obtained parent virus was characterized by RT-PCR to ensure the presence of the cloned Spike gene within the NDV genome. The identity and stability of Spike gene within the Newcastle genome were also confirmed by sequencing. Expression of the Spike protein expressed by the parent virus was also confirmed by immunoperoxidase.

This parent virus was propagated by two consecutive passages in a 10 days old SPF chicken embryo in order to increase the titer and generate the Master Seed, and one more passage in a chicken embryo to generate the Production Seed from which an experimental vaccine was formulated.

Characterization tests by RT-PCR of the master seed, production seed and generated experimental vaccine, resulted positive, with the band corresponding to the inserted Spike gene amplified. However, when the recombinant virus of each passage was sequenced, three mutations in the Spike gene were identified. A transcription stop codon was located in the coding sequence in subunit 2, and two more mutations in the carboxy terminal region.

In the immunoperoxidase analysis to detect expression of the Spike protein in the master seed, production seed and experimental vaccine, a gradual decrease in expression was observed. The more passages, the smaller amount of protein was detected by anti-Spike antibody, to such a degree that the experimental vaccine results in an almost zero percentage of Spike protein. These results indicated that the Spike gene may be detected by RT-PCR and remained inserted into the vector; however, with each passage in the chicken embryo the stability of the gene was disrupted.

Still, since the master seed had a good result of Spike expression by immunoperoxidase, this material was used to formulate the vaccine used in the pre-clinical trial in pigs.

However, the analysis of the sera of the 0 and 21 days old vaccinated pigs indicated that the Spike protein, expressed by the recombinant virus of rNDVLS/Spike S1/S2 SARS-COV-2/PreF version of the example 5, did not induce specific IgG antibodies, nor specific neutralizing antibodies against SARS-COV-2.

This result clearly shows that, despite the structure designed with two prolines in the sequence, the generation of the Spike protein was compromised, resulting in the expression of Spike protein with a three-dimensional structure not suitable for induction of neutralizing antibodies, contrary to what was expected.

Example 7B—Stabilization of Protein S (Spike) with 6 Prolines

The Spike gene of the rNDVLS/Spike S1/S2 SARS-COV-2/Hexapro version preserve the ectodomain of the Spike gene fused to Transmembrane and Cytoplasmic region (TMC or TMCyto) of the F (Fusion) gene of Newcastle virus. The nucleotide sequence of the chimeric gene has codon usage optimized for human. The cleavage site for Furin (F) was removed and six prolines were introduced into the sequence to ensure the Hexa-pro structure of the final protein.

The same process methodology was applied to generate the Hexa-pro parent virus and subsequent master seeds, production seed and experimental vaccine. With this design, the same tests conducted in accordance to example 7A, RT-PCR, sequencing, immunoperoxidase and SDS-PAGE (Coomassie), resulted positive for identity and stability of quimeric Spike Hexa-Pro protein, different from the construct of such example 7A.

The recombinant virus rNDVLS/Spike S1/S2 SARS-COV-2/Hexapro from example 5 was used in pre-clinical trials in SPF pigs, with positive results for detection of IgG antibodies and neutralizing antibodies against SARS-COV-2.

Example 8

Study to Assess the Safety and Immunogenicity Level Produced in Pigs by the Active Vaccine Against COVID-19

A study was carried out to evaluate the safety and immunogenicity of the vaccine in accordance to the principles of the present invention in SPF pigs.

For this study, a virus was designed using the plasmid pLS11801140_L289A (SEQ ID NO: 14) generated in example 1 with the Spike S1/S2 SARS-COV-2/Hexapro version, following the process previously described in examples 2-6.

The vaccine was formulated in four doses of $10^{7.0}$ CEID50%/mL, $10^{7.5}$ CEID50%/mL, $10^{8.0}$ CEID50%/mL, $10^{8.5}$ CEID50%/mL of live or active virus per dose by different routes of administration (oral, intramuscular and its combination) with two applications of the doses. The safety level was determined by measuring the presence or absence of adverse reactions after the vaccine application. The immunogenicity was evaluated by comparing the immune response generated after the application of the two doses of vaccine by means of an ELISA test for detecting neutralizing antibodies (GenScript) against the RBD protein of SARS-COV-2 (28 dpv). Table 3 shows the study design.

TABLE 3

| Vaccine | Route IN | Route IM | Application volume | Number of applications | Group | Pigs |
|---|---|---|---|---|---|---|
| $10^{8.0}$ CEID50%/mL active virus | XX | | 2.0 mL | 2 (0 and 21 days) | 1 | 8 |
| $10^{7.5}$ CEID50%/mL active virus | XX | | 2.0 mL | 2 (0 and 21 days) | 2 | 6 |
| $10^{7.0}$ CEID50%/mL active virus | XX | | 2.0 mL | 2 (0 and 21 days) | 3 | 6 |
| $10^{8.5}$ CEID50%/mL active virus | | XX | 1.0 mL | 2 (0 and 21 days) | 4 | 6 |
| $10^{8.0}$ CEID50%/mL active virus | | XX | 1.0 mL | 2 (0 and 21 days) | 5 | 6 |
| $10^{7.5}$ CEID50%/mL active virus | | XX | 1.0 mL | 2 (0 and 21 days) | 6 | 6 |
| $10^{7.0}$ CEID50%/mL active virus | | XX | 1.0 mL | 2 (0 and 21 days) | 7 | 6 |
| $10^{7.5}$ CEID50%/mL active virus | X | X | 2.0 mL/1.0 mL | 2 (0 days) | 8 | 6 |
| $10^{7.5}$ CEID50%/mL active virus | X | X | 2.0 mL/1.0 mL | 2 (0 and 21 days) | 9 | 6 |
| $10^{8.0}$ CEID50%/mL active virus | | XX | 1.0 mL | 2 (0 and 21 days) | 10 | 6 | wherein:
IN = Intranasal,
IM = Intramuscular,
X = 1 dose

A total of 62 SPF pigs of similar age/body weight (3-4 weeks old) were used in the study in different experimental groups. Animals were randomly placed according to their weight in isolation cubicles. No relevant adverse reactions were observed in any of the animals.

Animals were observed for clinical signs throughout the study period. The monitored clinical signs were abnormal respiration, abnormal behavior, and rectal temperature each morning. For animal welfare reasons the animals were observed more than once a day.

In the clinical report only in group 10 (inactivated vaccine) was observed that one of the piglets presented an adverse reaction 30 seconds post vaccination, showing salivation, depression and muscle tremors; the piglet was immediately treated, damped with cold water and the response was evaluated; 5 minutes after the adverse reaction, the pig did not show serious clinical manifestations, remained depressed for 1 hour and returned to normal. With the second vaccine application this pig did not show any kind of post vaccinal adverse reaction.

There were no evident clinical manifestations in the daily check-ups in any of the piglets in all groups throughout the test. This indicates that the used vaccines, with different titles and routes of application, were safe and complied with the safety test.

To determine the viral load, samples (nasal swabs on day 0 pre vaccination, 1 day after the first vaccination and 1 day after the second vaccination) were taken to assess the vaccine presence based on the load of genetic material of the vaccine virus. The genetic load was also assessed after sacrifice in lung tissue samples by RT-PCRtrq against the vector virus (NDV) and detecting the insert encoding the SARS-COV-2 Spike protein in the same vector.

All samples were negative for detection of genetic material against the vector virus (NDV), both in the baseline sampling and 24 hours after the first vaccination.

For the assessment of antibodies against SARS-COV-2 Spike, a commercial ELISA kit (GenScript) authorized by the FDA was used, which detects in a non-functional way neutralizing antibodies against RBD of SARS-COV-2 virus.

The degree of immunogenicity induced by vaccination was assessed by production of neutralizing antibodies (GenScript cPass) against RBD protein of SARS-COV-2. Serological samples were taken at day 0, 21, and 28 after the first vaccination. The results for the groups at 35 days after the first vaccination are shown in the following table 4.

TABLE 4

| Group | Elisa-Serum Virus-Neutralization | | | Mean Inhibition | Mean Title (ELISA-VSN) |
| | (+) | (−) | (%) Positive | % | |
|---|---|---|---|---|---|
| Group 1 | 8 | 0 | 100 | 79.29 | 1:190 (log$_2$ = 7.57) |
| Group 2 | 4 | 2 | 66.66 | 55.52 | — |
| Group 3 | 5 | 1 | 83.33 | 59.98 | — |
| Group 4 | 6 | 10 | 100 | 95.39 | — |
| Group 5 | 6 | 0 | 100 | 92.10 | 1:1,667 (log$_2$ = 10.70) |
| Group 6 | 6 | 0 | 100 | 92.85 | 1:700 (log$_2$ = 9.45) |
| Group 7 | 6 | 0 | 100 | 91.06 | 1:200 (log2 = 7.64) |
| Group 8 | 4 | 1 | 80 | 32.06 | — |
| Group 9 | 6 | 0 | 100 | 94.90 | 1:1,100 (log$_2$ = 10.10) |
| Group 10 | 6 | 10 | 100 | 96.04 | 1:1,800 (log$_2$ = 10.81) |
| Cx (+) Hum | two | 10 | 100 | 94.21 | 1:600 (log$_2$ = 9.22 |
| Cx (+) Kit | NA | NA | NA | 94.42 | 1 = 900 (log$_2$ = 9.81) |

It should be noted that in order to compare these results, serum from a patient affected by SARS-COV-2 who had the disease at the same time the test conducting was included, identified as Cx (+), and it was observed that for several groups the mean titers were even higher than those of the convalescent patient.

Additionally, for Group 1 which received two intranasal vaccines, the same test was conducted using oral fluids in order to detect the possibility of local immunity, the synergistic effect of which is observed in Group 9 which received the first dose by intranasal route and the second dose by intramuscular route. In this regard, although there are no comparable results, the antibody levels in oral fluids positive for Group 1 at day 28 and 35 suggest the possibility of prevention of infection by SARS-COV-2 virus in the primary infection route (upper respiratory mucosa) when two doses are administered intranasally.

Similarly, fourteen days after the second application, day 35 after the first vaccination, all surviving animals were humanitarily sacrificed and lung, lymph nodes, liver, kidney and spleen samples were collected to determine the presence of the vaccine virus by RT-PCRtrq, as well as for histopathologic assessment of possible pulmonary lesions using the planimetry technique and macro- and microscopic changes of the lung, present in the lung for the intranasal route, and in the area of intramuscular application.

After humanitarian sacrifice and necropsy of the pigs it was detected that the lungs of all the animals did not show lesions suggestive of viral infection and therefore from the used active vaccine. In the area of intramuscular vaccine application, no active or chronic inflammatory processes were detected, nor the presence of areas of fibrosis or abscesses, so indicating that the application of the vaccine by intranasal or intramuscular route did not generate lesions in the lung level or tissue level in the area of vaccine application.

From this example it can be seen that, in accordance with the principles of the present invention, it is possible to obtain a stable recombinant virus for large-scale industrial production, which can exhibit safety and immunogenicity in a mammalian animal model by various routes of administration in its active or inactivated form.

In this same example it is demonstrated that it is possible to administer by intranasal route a dose of an active virus comprising antigenic sites of SARS-COV-2, such as in the embodiment tested in example 8, followed by a second dose by intramuscular route of the same recombinant virus. From this experiment, a person skilled in the art can infer that it is possible to administer any other SARS-COV-2 antigen by intramuscular route to obtain protection, since it has been shown that application of the vaccine by intranasal route with a first dose was sufficient to stimulate a systemic response to the virus antigen by intramuscular route, which could be achieved by administering a different vaccine.

Therefore, even when specific embodiments of the invention have been illustrated and described, it should be emphasized that numerous modifications are possible, such as the used virus as the viral vector, and the used exogenous viral sequence. Therefore, the present invention should not be construed as restricted except as required by the prior art and appended claims.

The invention claimed is:

1. A recombinant Newcastle disease virus (NDV) comprising a NDV viral vector comprising SEQ ID NO:6 or SEQ ID NO:14 and an exogenous nucleotide sequence encoding for antigenic sites of severe acute respiratory syndrome coronavirus 2 (SARS-COV-2), wherein the exogenous nucleotide sequence comprises an ectodomain of a spike (S) protein of SARS-COV-2 fused to a transmembrane domain and a cytoplasmic domain of a NDV fusion (F) protein, wherein the polybasic cleavage site of the ectodo-main of the S protein is mutated to an alanine and amino acids that correspond to amino acids 817, 892, 899, 942, 986 and 987 of the ectodomain of the S protein of SEQ ID NO:11 are mutated to prolines, whereby the NDV viral vector and the antigenic sites are stable after at least 3 consecutive passages in chicken embryo.

2. The recombinant NDV according to claim 1, wherein the recombinant NDV is used in an active form.

3. The recombinant NDV according to claim 1, wherein the recombinant NDV is used in an inactivated form.

4. The recombinant NDV according to claim 1, wherein the NDV viral vector comprises SEQ ID NO:6.

5. The recombinant NDV according to claim 1, wherein the NDV viral vector comprises SEQ ID NO:14.

6. The recombinant NDV according to claim 1, wherein the S protein ectodomain nucleotide sequence is a sequence having at least 80% identity with any sequence that translates into the amino acid sequence of the exodomain of the S protein of SEQ ID NO: 11 and still comprises all of the S protein mutations of claim 1.

7. The recombinant NDV according to claim 1, wherein the S protein ectodomain nucleotide sequence is any sequence that translates into the amino acid sequence of the exodomain of the S protein of SEQ ID NO: 11.

8. A coronavirus disease 2019 (COVID-19) vaccine comprising:

a recombinant Newcastle disease virus (NDV) comprising an NDV viral vector comprising SEQ ID NO:6 or SEQ ID NO:14 and an exogenous nucleotide sequence encoding for antigenic sites of severe acute respiratory syndrome coronavirus 2 (SARS-CoV-2), wherein the exogenous nucleotide sequence comprises an ectodomain of a spike (S) protein of SARS-COV-2 fused to a transmembrane domain and a cytoplasmic domain of a NDV fusion (F) protein, wherein the polybasic cleavage site of the ectodomain of the S protein is mutated to an alanine and amino acids that correspond to amino acids 817, 892, 899, 942, 986 and 987 of the ectodomain of the S protein of SEQ ID NO:11 are mutated to prolines, whereby the NDV viral vector and the antigenic sites are stable after at least 3 consecutive passages in chicken embryo, and a pharmaceutically acceptable carrier, adjuvant and/or excipient.

9. The COVID-19 vaccine according to claim 8, wherein the recombinant NDV is live.

10. The COVID-19 vaccine according to claim 8, wherein the recombinant NDV is inactivated.

11. The COVID-19 vaccine according to claim 8, wherein the NDV viral vector comprises SEQ ID NO:6.

12. The COVID-19 vaccine according to claim 8, wherein the NDV viral vector comprises SEQ ID NO:14.

13. The COVID-19 vaccine according to claim 8, wherein the S protein ectodomain nucleotide sequence is a sequence having at least 80% identity with any sequence that translates into the amino acid sequence of the exodomain of the S protein of SEQ ID NO: 11 and still comprises all of the S protein mutations of claim 12.

14. The COVID-19 vaccine according to claim 8, wherein the S protein ectodomain nucleotide sequence is any sequence that translates into the amino acid sequence of the exodomain of the S protein of SEQ ID NO: 11.

15. The COVID-19 vaccine according to claim 8, wherein the pharmaceutically acceptable carrier comprises an aqueous solution or an emulsion.

16. The COVID-19 vaccine according to claim 15, wherein the emulsion is a water-oil emulsion, an oil-water emulsion, or a water-oil-water emulsion.

17. The COVID-19 vaccine according to claim 15, wherein the emulsion is a water-oil-water emulsion.

18. The COVID-19 vaccine according to claim 8, wherein the recombinant NDV is an active virus in a concentration between $10^{6.0}$ and $10^{10.0}$ CEID50%/mL per volume dose.

19. The COVID-19 vaccine according to claim 8, wherein the recombinant NDV is an active virus in a concentration between $10^{6.0}$ and $10^{8.5}$ CEID50%/mL per dose.

20. The COVID-19 vaccine according to claim 18, wherein the volume per dose is 0.2 to 2 mL.

21. The COVID-19 vaccine according to claim 8, wherein the COVID-19 vaccine is adapted to be administrable intramuscularly, intranasally, subcutaneously, by spraying, or by nebulization.

22. The COVID-19 vaccine according to claim 21, wherein the COVID-19 vaccine is adapted to be administrable intramuscularly or intranasally.

23. A method for treating or preventing coronavirus disease 2019 (COVID-19) in a subject, the method comprising administering to the subject an effective amount of the recombinant Newcastle disease virus (NDV) of claim 1.

24. The method of claim 23, wherein the recombinant NDV is administered in a dose between $10^{6.0}$ and $10^{10.0}$ CEID50%/mL in a volume between 0.2 and 2 mL.

25. The method of claim 24, wherein the recombinant NDV is administered in a dose between $10^{6.5}$ and $10^{8.5}$ CEID50%/mL.

26. The method of claim 23, wherein the recombinant NDV is administered intramuscularly, intranasally, subcutaneously, by spraying, or by nebulization.

27. The method of claim 24, wherein the recombinant NDV is administered intranasally in a dose between $10^{7.5}$ and $10^{8.5}$ CEID50%/mL.

28. The method of claim 24, wherein the recombinant NDV is administered intramuscularly in a dose between $10^{7.0}$ and $10^{8.5}$ CEID50%/mL.

29. The method of claim 26, wherein the recombinant NDV is administered in a first dose and a second dose.

30. The method of claim 29, wherein the recombinant NDV is administered 7 to 35 days apart between the first dose and the second dose.

31. The method of claim 30, wherein the recombinant NDV is administered 21 to 28 days apart between the first dose and the second dose.

32. The method of claim 29, wherein the first dose is administered intranasally and the second dose is administered intramuscularly.

33. The method of claim 23, wherein the recombinant NDV generates mucosal immunity against infection by SARS-COV-2.

34. A method for treatment or prevention of coronavirus disease 2019 (COVID-19) caused by SARS-COV-2 in a subject, the method comprising administering a first dose, followed by a second dose, of an effective amount of the recombinant NDV of claim 1 to the subject, wherein the first dose is an active recombinant NDV administered intranasally and the second dose is an active recombinant NDV or an inactivated recombinant NDV administered intramuscularly.

35. The method of claim 34, wherein the second dose is the active recombinant NDV.

36. The method of claim 34, wherein the second dose is the inactivated recombinant NDV.

* * * * *

SEQUENCE LISTING

<160> NUMBER OF SEQ ID NOS: 14

<210> SEQ ID NO 1
<211> LENGTH: 3870
<212> TYPE: DNA
<213> ORGANISM: SARS-CoV2

<400> SEQUENCE: 1
ccgcggttag aaaaaatacg ggtagaaccg ccaccatgtt tgtttttctt gtttttattgc      60

```
cactagtctc tagtcagtgt gttaatctta caaccagaac tcaattaccc cctgcataca      120
ctaattcttt cacacgtggt gtttattacc ctgacaaagt tttcagatcc tcagttttac      180
attcaactca ggacttgttc ttacctttct tttccaatgt tacttggttc catgctatac      240
atgtctctgg gaccaatggt actaagaggt ttgataaccc tgtcctacca tttaatgatg      300
gtgtttattt tgcttccact gagaagtcta acataataag aggctggatt tttggtacta      360
ctttagattc gaagacccag tccctactta ttgttaataa cgctactaat gttgttatta      420
aagtctgtga atttcaattt tgtaatgatc cattttggg tgtttattac cacaagaaca       480
acaaaagttg gatggaaagt gagttcagag tttattctag tgcgaataat tgcacttttg      540
aatatgtctc tcagcctttt cttatggacc ttgaaggaaa acagggtaat ttcaagaatc      600
ttagggaatt tgtgtttaag aatattgatg gttattttaa aatatattct aagcacacgc      660
ctattaattt agtgcgtgat ctccctcagg gttttttcggc tttagaacca ttggtagatt      720
tgccaatagg tattaacatc actaggtttc aaactttact tgctttacat agaagttatt      780
tgactcctgg tgattcttct tcaggttgga cagctggtgc tgcagcttat tatgtgggtt      840
atcttcaacc taggactttt ctattaaaat ataatgaaaa tggaaccatt acagatgctg      900
tagactgtgc acttgaccct ctctcagaaa caaagtgtac gttgaaatcc ttcactgtag      960
agaaaggaat ctatcaaact tctaacttta gagtccaacc aacagaatct attgttagat     1020
ttcctaatat tacaaacttg tgccctttg gtgaagtttt taacgccacc agatttgcat      1080
ctgtttatgc ttggaacagg aagagaatca gcaactgtgt tgctgattat tctgtcctat     1140
ataattccgc atcattttcc acttttaagt gttatggagt gtctcctact aaattaaatg     1200
atctctgctt tactaatgtc tatgcagatt catttgtaat tagaggtgat gaagtcagac     1260
aaatcgctcc agggcaaact ggaaagattg ctgattataa ttataaatta ccagatgatt     1320
ttacaggctg cgttatagct tggaattcta caatcttga ttctaaggtt ggtggtaatt      1380
ataattacct gtatagattg tttaggaagt ctaatctcaa acctttgag agagatattt      1440 caactgaaat ctatcaggcc ggtagcacac cttgtaatgg tgttgaaggt tttaattgtt     1500
actttccttt acaatcatat ggtttccaac ccactaatgg tgttggttac caaccataca     1560
gagtagtagt actttctttt gaacttctac atgcaccagc aactgtttgt ggacctaaga     1620
agtctactaa tttggttaag aacaaatgtg tcaatttcaa cttcaatggt ttaacaggca     1680
caggtgttct tactgagtct aacaagaagt ttctgccttt ccaacaattt ggcagagaca     1740
ttgctgacac tactgatgct gtccgtgatc cacagacact tgagattctt gacattacac     1800
catgttcttt tggtggtgtc agtgttataa caccaggaac aaatacttct aaccaggttg     1860
ctgttcttta tcaggatgtt aactgcacag aagtccctgt tgctattcat gcagatcaac     1920
ttactcctac ttggcgtgtt tattctacag gttctaatgt ttttcaaaca cgtgcaggct     1980
gtttaatagg ggctgaacat gtcaacaact catatgagtg tgacataccc attggtgcag     2040
gtatatgcgc tagttatcag actcagacta attctcctcg gcgggcacgt agtgtagcta     2100
gtcaatccat cattgcctac actatgtcac ttggtgcaga aaattcagtt gcttactcta     2160
ataactctat tgccataccc acaaatttta ctattagtgt taccacagaa attctaccag     2220
tgtctatgac caagacatca gtagattgta caatgtacat ttgtggtgat tcaactgaat     2280
gcagcaatct tttgttgcaa tatggcagtt tttgtacaca attaaaccgt gctttaactg     2340
gaatagctgt tgaacaagac aagaacaccc aagaagtttt tgcacaagtc aaacaaattt     2400
acaaaacacc accaattaaa gatttggtg gttttaattt ttcacaaata ttaccagatc     2460
```

-continued

```
catcaaaacc aagcaagagg tcatttattg aagatctact tttcaacaaa gtgacacttg      2520
cagatgctgg cttcatcaaa caatatggtg attgccttgg tgatattgct gctagagacc      2580
tcatttgtgc acaaaagttt aacggcctta ctgtttttgcc acctttgctc acagatgaaa     2640
tgattgctca atacacttct gcactgttag cgggtacaat cacttctggt tggacctttg      2700
gtgcaggtgc tgcattacaa ataccatttg ctatgcaaat ggcttatagg tttaatggta      2760
ttggagttac acagaatgtt ctctatgaga accagaaatt gattgccaac caatttaata      2820
gtgctattgg caaaattcaa gactcacttt cttccacagc aagtgcactt ggaaaacttc      2880
aagatgtggt caaccaaaat gcacaagctt taaacacgct tgttaaacaa cttagctcca      2940
attttggtgc aatttcaagt gttttaaatg atatcctttc acgtcttgac aaagttgagg      3000
ctgaagtgca aattgatagg ttgatcacag gcagacttca aagtttgcag acatatgtga      3060
ctcaacaatt aattagagct gcagaaatca gagcttctgc taatcttgct gctactaaaa      3120
tgtcagagtg tgtacttgga caatcaaaga gagttgattt ttgtggaaag ggctatcatc      3180
ttatgtcctt ccctcagtca gcacctcatg gtgtagtctt cttgcatgtg acttatgtcc      3240
ctgcacaaga aaagaacttc acaactgctc ctgccatttg tcatgatgga aaagcacact      3300
ttcctcgtga aggtgtcttt gtttcaaatg gcacacactg gtttgtaaca caaaggaatt      3360
tttatgaacc acaaatcatt actacagaca acacatttgt gtctggtaac tgtgatgttg      3420
taataggaat tgtcaacaac acagtttatg atcctttgca acctgaatta gactcattca      3480
aggaggagtt agataaatat tttaagaatc atacatcacc agatgttgat ttaggtgaca      3540
tctctggcat taatgcttca gttgtaaaca ttcagaaaga aattgaccgc ctcaatgagg      3600
ttgccaagaa tttaaatgaa tctctcatcg atctccaaga acttggaaag tatgagcagt      3660
atataaaatg gccatggtac atttggctag gtttttatagc tggcttgatt gccatagtaa      3720
tggtgacaat tatgctttgc tgtatgacca gttgctgtag ttgtctcaag ggctgttgtt      3780
cttgtggatc ctgctgcaaa tttgatgaag acgactctga gccagtgctc aaaggagtca      3840
aattacatta cacataataa tgaaccgcgg                                       3870
```

```
<210> SEQ ID NO 2
<211> LENGTH: 2268
<212> TYPE: DNA
<213> ORGANISM: SARS-CoV2

<400> SEQUENCE: 2
```

```
ccgcggttag aaaaaatacg ggtagaaccg ccaccatgtt tgttttttctt gttttattgc        60 cactagtctc tagtcagtgt gttaatctta caaccagaac tcaattaccc cctgcataca       120
ctaattcttt cacacgtggt gtttattacc ctgacaaagt tttcagatcc tcagttttac       180
attcaactca ggacttgttc ttacctttct tttccaatgt tacttggttc catgctatac       240
atgtctctgg gaccaatggt actaagaggt ttgataaccc tgtcctacca tttaatgatg       300
gtgtttattt tgcttccact gagaagtcta acataataag aggctggatt tttggtacta       360
ctttagattc gaagacccag tccctactta ttgttaataa cgctactaat gttgttatta       420
aagtctgtga atttcaattt gtaatgatc cattttttggg tgtttattac cacaagaaca       480
acaaaagttg gatggaaagt gagttcagag tttattctag tgcgaataat gcacttttg        540 aatatgtctc tcagcctttt cttatggacc ttgaaggaaa acagggtaat ttcaagaatc       600
ttagggaatt tgtgtttaag aatattgatg gttatttaa aatatattct aagcacacgc        660
```

-continued

```
ctattaattt agtgcgtgat ctccctcagg gttttttcggc tttagaacca ttggtagatt      720
tgccaatagg tattaacatc actaggtttc aaactttact tgctttacat agaagttatt      780
tgactcctgg tgattcttct tcaggttgga cagctggtgc tgcagcttat tatgtgggtt      840
atcttcaacc taggactttt ctattaaaat ataatgaaaa tggaaccatt acagatgctg      900
tagactgtgc acttgacct ctctcagaaa caaagtgtac gttgaaatcc ttcactgtag      960
agaaaggaat ctatcaaact tctaacttta gagtccaacc aacagaatct attgttagat     1020
ttcctaatat tacaaacttg tgcccttttg gtgaagtttt taacgccacc agatttgcat     1080
ctgtttatgc ttggaacagg aagagaatca gcaactgtgt tgctgattat tctgtcctat     1140
ataattccgc atcattttcc actttttaagt gttatggagt gtctcctact aaaattaaatg     1200 atctctgctt tactaatgtc tatgcagatt catttgtaat tagaggtgat gaagtcagac     1260
aaatcgctcc agggcaaact ggaaagattg ctgattataa ttataaaatta ccagatgatt     1320 ttacaggctg cgttatagct tggaattcta caatcttga ttctaaggtt ggtggtaatt     1380
ataattacct gtatagattg tttaggaagt ctaatctcaa acctttttgag agagatattt     1440 caactgaaat ctatcaggcc ggtagcacac cttgtaatgg tgttgaaggt tttaattgtt     1500
actttccttt acaatcatat ggtttccaac ccactaatgg tgttggttac caaccataca     1560
gagtagtagt actttctttt gaacttctac atgcaccagc aactgtttgt ggacctaaga     1620
agtctactaa tttggttaag aacaaatgtg tcaatttcaa cttcaatggt ttaacaggca     1680
caggtgttct tactgagtct aacaagaagt ttctgccttt ccaacaattt ggcagagaca     1740
ttgctgacac tactgatgct gtccgtgatc cacagacact tgagattctt gacattacac     1800
catgttcttt tggtggtgtc agtgttataa caccaggaac aaatacttct aaccaggttg     1860
ctgttcttta tcaggatgtt aactgcacag aagtccctgt tgctattcat gcagatcaac     1920
ttactcctac ttggcgtgtt tattctacag gttctaatgt ttttcaaaca cgtgcaggct     1980
gtttaatagg ggctgaacat gtcaacaact catatgagtg tgacataccc attggtgcag     2040
gtatatgcgc tagttatcag actcagacta attctcctcg gcgggcacgt gttaacctca     2100
ttacctatat cgttttgact atcatatctc ttgtttttgg tatacttagc ctgattctag     2160
catgctacct aatgtacaag caaaaggcgc aacaaaagac cttattatgg cttgggaata     2220
ataccctaga tcagatgaga gccactacaa agatgtaatg aaccgcgg               2268
```

<210> SEQ ID NO 3
<211> LENGTH: 3852
<212> TYPE: DNA
<213> ORGANISM: SARS-CoV2

<400> SEQUENCE: 3

```
ccgcggttag aaaaaatacg ggtagaaccg ccaccatgtt tgttttttctt gtttttattgc       60 cactagtctc tagtcagtgt gttaatctta caaccagaac tcaattaccc cctgcataca      120
ctaattcttt cacacgtggt gtttattacc ctgacaaagt tttcagatcc tcagttttac      180
attcaactca ggacttgttc ttacctttct tttccaatgt tacttggttc catgctatac      240
atgtctctgg gaccaatggt actaagaggt ttgataaccc cgtcctacca tttaatgatg      300
gtgtttattt tgcttccact gagaagtcta acataataag aggctggatt tttggtacta      360
ctttagattc gaagacccag tccctactta ttgttaataa cgctactaat gttgttatta      420
aagtctgtga atttcaattt gtaatgatc cattttgggg tgtttattac cacaagaaca      480
acaaaagttg gatggaaagt gagttcagag tttattctag tgcgaataat tgcacttttg      540
```

```
aatatgtctc tcagcctttt cttatggacc ttgaaggaaa acagggtaat ttcaagaatc      600
ttagggaatt tgtgtttaag aatattgatg gttattttaa aatatattct aagcacacgc      660
ctattaattt agtgcgtgat ctccctcagg gtttttcggc tttagaacca ttggtagatt      720
tgccaatagg tattaacatc actaggtttc aaactttact tgctttacat agaagttatt      780
tgactcctgg tgattcttct tcaggttgga cagctggtgc tgcagcttat tatgtgggtt      840
atcttcaacc taggactttt ctattaaaat ataatgaaaa tggaaccatt acagatgctg      900
tagactgtgc acttgaccct ctctcagaaa caaagtgtac gttgaaatcc ttcactgtag      960
agaaaggaat ctatcaaact tctaacttta gagtccaacc aacagaatct attgttagat     1020
ttcctaatat tacaaacttg tgcccttttg gtgaagtttt taacgccacc agatttgcat     1080
ctgtttatgc ttggaacagg aagagaatca gcaactgtgt tgctgattat tctgtcctat     1140
ataattccgc atcattttcc acttttaagt gttatggagt gtctcctact aaaattaaatg    1200 atctctgctt tactaatgtc tatgcagatt catttgtaat tagaggtgat gaagtcagac     1260
aaatcgctcc agggcaaact ggaaagattg ctgattataa ttataaatta ccagatgatt     1320
ttacaggctg cgttatagct tggaattcta acaatcttga ttctaaggtt ggtggtaatt     1380
ataattacct gtatagattg tttaggaagt ctaatctcaa accttttgag agagatattt     1440
caactgaaat ctatcaggcc ggtagcacac cttgtaatgg tgttgaaggt tttaattgtt     1500
actttccttt acaatcatat ggtttccaac ccactaatgg tgttggttac caaccataca     1560
gagtagtagt actttctttt gaacttctac atgcaccagc aactgtttgt ggacctaaga     1620
agtctactaa tttggttaag aacaaatgtg tcaatttcaa cttcaatggt ttaacaggca     1680
caggtgttct tactgagtct aacaagaagt ttctgccttt ccaacaattt ggcagagaca     1740
ttgctgacac tactgatgct gtccgtgatc cacagacact tgagattctt gacattacac     1800
catgttcttt tggtggtgtc agtgttataa caccaggaac aaatacttct aaccaggttg     1860
ctgttcttta tcaggatgtt aactgcacag aagtccctgt tgctattcat gcagatcaac     1920
ttactcctac ttggcgtgtt tattctacag gttctaatgt ttttcaaaca cgtgcaggct     1980
gtttaatagg ggctgaacat gtcaacaact catatgagtg tgacataccc attggtgcag     2040
gtatatgcgc tagttatcag actcagacta attctcctcg gcgggcacgt agtgtagcta     2100
gtcaatccat cattgcctac actatgtcac ttggtgcaga aaattcagtt gcttactcta     2160
ataactctat tgccataccc acaaatttta ctattagtgt taccacagaa attctaccag     2220
tgtctatgac caagacatca gtagattgta caatgtacac ttgtggtgat tcaactgaat     2280
gcagcaatct tttgttgcaa tatggcagtt tttgtacaca attaaaccgt gctttaactg     2340
gaatagctgt tgaacaagac aagaacaccc aagaagtttt tgcacaagtc aaacaaattt     2400
acaaaacacc accaattaaa gattttggtg gttttaattt ttcacaaata ttaccagatc     2460
catcaaaacc aagcaagagg tcatttattg aagatctact tttcaacaaa gtgacacttg     2520
cagatgctgg cttcatcaaa caatatggtg attgccttgg tgatattgct gctagagacc     2580
tcatttgtgc acaaaagttt aacggcctta ctgttttgcc acctttgctc acagatgaaa     2640
tgattgctca atacacttct gcactgttag cgggtacaat cacttctggt tggacctttg     2700
gtgcaggtgc tgcattacaa ataccatttg ctatgcaaat ggcttatagg tttaatggta     2760
ttggagttac acagaatgtt ctctatgaga accagaaatt gattgccaac caatttaata     2820
gtgctattgg caaaattcaa gactcacttt cttccacagc aagtgcactt ggaaaacttc     2880
```

```
aagatgtggt caaccaaaat gcacaagctt taaacacgct tgttaaacaa cttagctcca      2940
attttggtgc aatttcaagt gttttaaatg atatcctttc acgtcttgac aaagttgagg      3000
ctgaagtgca aattgatagg ttgatcacag gcagacttca aagtttgcag acatatgtga      3060
ctcaacaatt aattagagct gcagaaatca gagcttctgc taatcttgct gctactaaaa      3120
tgtcagagtg tgtacttgga caatcaaaga gagttgattt ttgtggaaag ggctatcatc      3180
ttatgtcctt ccctcagtca gcacctcatg gtgtagtctt cttgcatgtg acttatgtcc      3240
ctgcacaaga aaagaacttc acaactgctc ctgccatttg tcatgatgga aaagcacact      3300
ttcctcgtga aggtgtcttt gtttcaaatg gcacacactg gtttgtaaca caaaggaatt      3360
tttatgaacc acaaatcatt actacagaca acacatttgt gtctggtaac tgtgatgttg      3420
taataggaat tgtcaacaac acagtttatg atcctttgca acctgaatta gactcattca      3480
aggaggagtt agataaatat tttaagaatc atacatcacc agatgttgat ttaggtgaca      3540
tctctggcat taatgcttca gttgtaaaca ttcagaaaga aattgaccgc ctcaatgagg      3600
ttgccaagaa tttaaatgaa tctctcatcg atctccaaga acttggaaag tatgagcagt      3660
atataaaatg gccagttaac ctcattacct atatcgtttt gactatcata tctcttgttt      3720
ttggtatact tagcctgatt ctagcatgct acctaatgta caagcaaaag gcgcaacaaa      3780
agaccttatt atggcttggg aataataccc tagatcagat gagagccact acaaagatgt      3840
aatgaaccgc gg                                                          3852

<210> SEQ ID NO 4
<211> LENGTH: 3858
<212> TYPE: DNA
<213> ORGANISM: SARS-CoV2

<400> SEQUENCE: 4
ccgcggttag aaaaaatacg ggtagaaccg ccaccatgtt cgtgtttctg gtgctgctgc        60
ctctggtgtc cagccagtgt gtgaacctga ccacaagaac ccagctgcct ccagcctaca       120
ccaacagctt taccagaggc gtgtactacc ccgacaaggt gttcagatcc agcgtgctgc       180
actctaccca ggacctgttc ctgccttttct tcagcaacgt gacctggttc cacgccatcc       240
acgtgtccgg caccaatggc accaagagat cgacaaccc cgtgctgccc ttcaacgacg       300
gggtgtactt tgccagcacc gagaagtcca acatcatcag aggctggatc ttcggcacca       360
cactggacag caagacccag agcctgctga tcgtgaacaa cgccaccaac gtggtcatca       420
aagtgtgcga gttccagttc tgcaacgacc ccttcctggg cgtctactat cacaagaaca       480
acaagagctg gatggaaagc gagttccggg gtgtacagcag cgccaacaac tgcaccttcg       540
agtacgtgtc ccagcctttc ctgatggacc tggaaggcaa gcaggcaac ttcaagaacc       600 tgcgcgagtt cgtgttcaag aacatcgacg gctacttcaa gatctacagc aagcacaccc       660
ctatcaacct cgtgcgggat ctgcctcagg gcttctctgc tctggaaccc ctggtggatc       720
tgcccatcgg catcaacatc acccggtttc agacactgct ggccctgcac agaagctacc       780
tgacacctgg cgatagcagc agcggatgga cagctggtgc cgccgcttac tatgtgggct       840
acctgcagcc tagaacctttt ctgctgaagt acaacgagaa cggcaccatc accgacgccg       900
tggattgtgc tctggatcct ctgagcgaga caaagtgcac cctgaagtcc ttcaccgtgg       960
aaaagggcat ctaccagacc agcaacttcc gggtgcagcc caccgaatcc atcgtgcggt      1020
tccccaatat caccaatctg tgccccttcg gcgaggtgtt caatgccacc agattcgcct      1080
ctgtgtacgc ctggaaccgg aagcggatca gcaattgcgt ggccgactac tccgtgctgt      1140
```

```
acaactccgc cagcttcagc accttcaagt gctacggcgt gtccctacc  aagctgaacg   1200 acctgtgctt cacaaacgtg tacgccgaca gcttcgtgat ccggggagat gaagtgcggc   1260
agattgcccc tggacagaca ggcaagatcg ccgactacaa ctacaagctg cccgacgact   1320
tcaccggctg tgtgattgcc tggaacagca acaacctgga ctccaaagtc ggcggcaact   1380
acaattacct gtaccggctg ttccggaagt ccaatctgaa gcccttcgag cgggacatct   1440
ccaccgagat ctatcaggcc ggcagcaccc cttgtaacgg cgtggaaggc ttcaactgct   1500
acttcccact gcagtcctac ggctttcagc ccacaaatgg cgtgggctat cagccctaca   1560
gagtggtggt gctgagcttc gaactgctgc atgcccctgc cacagtgtgc ggccctaaga   1620
aaagcaccaa tctcgtgaag aacaaatgcg tgaacttcaa cttcaacggc ctgaccggca   1680
ccggcgtgct gacagagagc aacaagaagt tcctgccatt ccagcagttt ggccgggata   1740
tcgccgatac cacagacgcc gttagagatc cccagacact ggaaatcctg gacatcaccc   1800
cttgcagctt cggcggagtg tctgtgatca cccctggcac caacaccagc aatcaggtgg   1860
cagtgctgta ccaggacgtg aactgtaccg aagtgcccgt ggccattcac gccgatcagc   1920
tgacacctac atggcgggtg tactccaccg gcagcaatgt gtttcagacc agagccggct   1980
gtctgatcgg agccgagcac gtgaacaata gctacgagtg cgacatcccc atcggcgctg   2040
gcatctgtgc cagctaccag acacagacaa acagccccgc ctctgtggcc agccagagca   2100
tcattgccta cacaatgtct ctgggcgccg agaacagcgt ggcctactcc aacaactcta   2160
tcgctatccc caccaacttc accatcagcg tgaccacaga gatcctgcct gtgtccatga   2220
ccaagaccag cgtggactgc accatgtaca tctgcggcga ttccaccgag tgctccaacc   2280
tgctgctgca gtacggcagc ttctgcaccc agctgaatag agccctgaca gggatcgccg   2340
tggaacagga caagaacacc caagaggtgt tcgcccaagt gaagcagatc tacaagaccc   2400 ctccctatcaa ggacttcggc ggcttcaatt tcagccagat tctgcccgat cctagcaagc   2460
ccagcaagcg gagcttcatc gaggacctgc tgttcaacaa agtgacactg gccgacgccg   2520
gcttcatcaa gcagtatggc gattgtctgg gcgacattgc cgccagggat ctgatttgcg   2580
cccagaagtt taacggactg acagtgctgc ctcctctgct gaccgatgag atgatcgccc   2640
agtacacatc tgccctgctg gccggcacaa tcacaagcgg ctggacattt ggagctggcg   2700
ccgctctgca gatccccttt gctatgcaga tggcctaccg gttcaacggc atcggagtga   2760
cccagaatgt gctgtacgag aaccagaagc tgatcgccaa ccagttcaac agcgccatcg   2820
gcaagatcca ggacagcctg agcagcacag caagcgccct gggaaagctg caggacgtgg   2880
tcaaccagaa tgcccaggca ctgaacaccc tggtcaagca gctgtcctcc aacttcggcg   2940
ccatcagctc tgtgctgaac gatatcctga gcagactgga ccctcctgaa gccgaggtgc   3000
agatcgacag actgatcacc ggaaggctgc agtccctgca gacctacgtt acccagcagc   3060
tgatcagagc cgccgagatt agagcctctg ccaatctggc cgccaccaag atgtctgagt   3120
gtgtgctggg ccagagcaag agagtggact tttgcggcaa gggctaccac ctgatgagct   3180
tccctcagtc tgcccctcac ggcgtggtgt tcctgcacgt gacatacgtg cccgctcaag   3240
agaagaattt caccaccgct ccagccatct gccacgacgg caaagcccac tttcctagag   3300
aaggcgtgtt cgtgtccaac ggcacccatt ggttcgtgac ccagcggaac ttctacgagc   3360
cccagatcat caccaccgac aacaccttcg tgtctggcaa ctgcgacgtc gtgatcggca   3420
ttgtgaacaa taccgtgtac gaccctctgc agcccgagct ggacagcttc aaagaggaac   3480
```

```
tggataagta ctttaagaac cacacaagcc ccgacgtgga cctgggcgat atcagcggaa   3540
tcaatgccag cgtcgtgaac atccagaaag agatcgaccg gctgaacgag gtggccaaga   3600
atctgaacga gagcctgatc gacctgcaag aactggggaa gtacgagcag tacatcaagt   3660
ggccctggta catttggcta ggttttatag ctggcttgat tgccatagta atggtgacaa   3720
ttatgctttg ctgtatgacc agttgctgta gttgtctcaa gggctgttgt tcttgtggat   3780
cctgctgcaa atttgatgaa gacgactctg agccagtgct caaaggagtc aaattacatt   3840
acacataatg aaccgcgg                                                  3858

<210> SEQ ID NO 5
<211> LENGTH: 3840
<212> TYPE: DNA
<213> ORGANISM: SARS-CoV2

<400> SEQUENCE: 5
ccgcggttag aaaaaatacg ggtagaaccg ccaccatgtt cgtgtttctg gtgctgctgc     60
ctctggtgtc cagccagtgt gtgaacctga ccacaagaac ccagctgcct ccagcctaca    120
ccaacagctt taccagaggc gtgtactacc ccgacaaggt gttcagatcc agcgtgctgc    180
actctaccca ggacctgttc ctgcctttct tcagcaacgt gacctggttc cacgccatcc    240
acgtgtccgg caccaatggc accaagagat tcgacaaccc cgtgctgccc ttcaacgacg    300
gggtgtactt tgccagcacc gagaagtcca acatcatcag aggctggatc ttcggcacca    360
cactggacag caagacccag agcctgctga tcgtgaacaa cgccaccaac gtggtcatca    420
aagtgtgcga gttccagttc tgcaacgacc ccttcctggg cgtctactat cacaagaaca    480
acaagagctg gatggaaagc gagttccggg gtacagcag cgccaacaac tgcaccttcg    540
agtacgtgtc ccagcctttc ctgatggacc tggaaggcaa gcagggcaac ttcaagaacc    600
tgcgcgagtt cgtgttcaag aacatcgacg gctacttcaa gatctacagc aagcacaccc    660
ctatcaacct cgtgcgggat ctgcctcagg gcttctctgc tctggaaccc ctggtggatc    720
tgcccatcgg catcaacatc acccggtttc agacactgct ggccctgcac agaagctacc    780
tgacacctgg cgatagcagc agcggatgga cagctggtgc cgccgcttac tatgtgggct    840
acctgcagcc tagaacctttt ctgctgaagt acaacgagaa cggcaccatc accgacgccg    900
tggattgtgc tctggatcct ctgagcgaga caaagtgcac cctgaagtcc ttcaccgtgg    960
aaaagggcat ctaccagacc agcaacttcc gggtgcagcc caccgaatcc atcgtgcggt   1020
tccccaatat caccaatctg tgccccttcg gcgaggtgtt caatgccacc agattcgcct   1080
ctgtgtagat cagcaattgc gtggccgact actccgtgct gtacaactcc gccagcttca   1140
gcaccttcaa gtgctacggc gtgtccccta ccaagctgaa cgacctgtgc ttcacaaacg   1200
tgtacgccga cagcttcgtg atccggggag atgaagtgcg gcagattgcc cctggacaga   1260
caggcaagat cgccgactac aactacaagc tgcccgacga cttcaccggc tgtgtgattg   1320
cctggaacag caacaacctg gactccaaag tcggcggcaa ctacaattac ctgtaccggc   1380
tgttccggaa gtccaatctg aagcccttcg agcgggacat ctccaccgag atctatcagg   1440
ccggcagcac cccttgtaac ggcgtggaag cttcaactg ctacttccca ctgcagtcct   1500
acggctttca gcccacaaat ggcgtgggct atcagcccta cagagtggtg gtgctgagct   1560
tcgaactgct gcatgcccct gccacagtgt gcggccctaa gaaaagcacc aatctcgtga   1620
agaacaaatg cgtgaacttc aacttcaacg gcctgaccgg caccggcgtg ctgacagaga   1680
gcaacaagaa gttcctgcca ttccagcagt ttggccggga tatcgccgat accacagacg   1740
```

```
ccgttagaga tccccagaca ctggaaatcc tggacatcac cccttgcagc ttcggcggag        1800
tgtctgtgat cacccctggc accaacacca gcaatcaggt ggcagtgctg taccaggacg        1860
tgaactgtac cgaagtgccc gtggccattc acgccgatca gctgacacct acatggcggg        1920
tgtactccac cggcagcaat gtgtttcaga ccagagccgg ctgtctgatc ggagccgagc        1980
acgtgaacaa tagctacgag tgcgacatcc ccatcggcgc tggcatctgt gccagctacc        2040
agacacagac aaacagcccc gcctctgtgg ccagccagag catcattgcc tacacaatgt        2100
ctctgggcgc cgagaacagc gtggcctact ccaacaactc tatcgctatc cccaccaact        2160
tcaccatcag cgtgaccaca gagatcctgc ctgtgtccat gaccaagacc agcgtggact        2220
gcaccatgta catctgcggc gattccaccg agtgctccaa cctgctgctg cagtacggca        2280
gcttctgcac ccagctgaat agagccctga cagggatcgc cgtggaacag gacaagaaca        2340
cccaagaggt gttcgcccaa gtgaagcaga tctacaagac ccctcctatc aaggacttcg        2400
gcggcttcaa tttcagccag attctgcccg atcctagcaa gcccagcaag cggagcttca        2460
tcgaggacct gctgttcaac aaagtgacac tggccgacgc cggcttcatc aagcagtatg        2520
gcgattgtct gggcgacatt gccgccaggg atctgatttg cgcccagaag tttaacggac        2580
tgacagtgct gcctcctctg ctgaccgatg agatgatcgc ccagtacaca tctgccctgc        2640
tggccggcac aatcacaagc ggctggacat ttggagctgg cgccgctctg cagatcccct        2700
ttgctatgca gatggcctac cggttcaacg gcatcggagt gacccagaat gtgctgtacg        2760
agaaccagaa gctgatcgcc aaccagttca cagcgccat cggcaagatc caggacagcc        2820
tgagcagcac agcaagcgcc ctgggaaagc tgcaggacgt ggtcaaccag aatgcccagg        2880
cactgaacac cctggtcaag cagctgtcct ccaacttcgg cgccatcagc tctgtgctga        2940
acgatatcct gagcagactg gaccctcctg aagccgaggt gcagatcgac agactgatca        3000
ccggaaggct gcagtccctg cagacctacg ttacccagca gctgatcaga gccgccgaga        3060
ttagagcctc tgccaatctg gccgccacca agatgtctga gtgtgtgctg ggccagagca        3120
agagagtgga cttttgcggc aagggctacc acctgatgag cttccctcag tctgcccctc        3180
acggcgtggt gtttctgcac gtgacatacg tgcccgctca agagaagaat ttcaccaccg        3240
ctccagccat ctgccacgac ggcaaagccc actttcctag agaaggcgtg ttcgtgtcca        3300
acggcaccca ttggttcgtg acccagcgga acttctacga gccccagatc atcaccaccg        3360
acaacacctt cgtgtctggc aactgcgacg tcgtgatcgg cattgtgaac aataccgtgt        3420
acgaccctct gcagcccgag ctggacagct caaagagga actggataag tactttaaga        3480
accacacaag ccccgacgtg gacctgggcg atatcagcgg aatcaatgcc agcgtcgtga        3540
acatccagaa agagatcgac cggctgaacg aggtggccaa gaatctgaac gagagcctga        3600
tcgacctgca agaactgggg aagtacgagc agtacatcaa gtggccctgg tacatttggc        3660
taggttttat agctggcttg attgccatag taatggtgac aattatgctt tgctgtatga        3720
ccagttgctg tagttgtctc aagggctgtt gttcttgtgg atcctgctgc aaatttgatg        3780
aagacgactc tgagccagtg ctcaaaggag tcaaattaca ttacacataa tgaaccgcgg        3840
```

<210> SEQ ID NO 6
<211> LENGTH: 18394
<212> TYPE: DNA
<213> ORGANISM: NDV LaSota

<400> SEQUENCE: 6

-continued

```
tcttccgctt cctcgctcac tgactcgctg cgctcggtcg ttcggctgcg gcgagcggta        60
tcagctcact caaaggcggt aatacggtta tccacagaat cagggggataa cgcaggaaag       120 aacatgtgag caaaaggcca gcaaaaggcc aggaaccgta aaaaggccgc gttgctggcg       180 ttttttccata ggctccgccc ccctgacgag catcacaaaa atcgacgctc aagtcagagg       240
tggcgaaacc cgacaggact ataaagatac caggcgtttc cccctggaag ctccctcgtg       300
cgctctcctg ttccgaccct gccgcttacc ggatacctgt ccgcctttct cccttcggga       360
agcgtggcgc tttctcatag ctcacgctgt aggtatctca gttcggtgta ggtcgttcgc       420
tccaagctgg gctgtgtgca cgaacccccc gttcagcccg accgctgcgc cttatccggt       480
aactatcgtc ttgagtccaa cccggtaaga cacgacttat cgccactggc agcagccact       540
ggtaacagga ttagcagagc gaggtatgta ggcggtgcta cagagttctt gaagtggtgg       600
cctaactacg gctacactag aagaacagta tttggtatct gcgctctgct gaagccagtt       660
accttcggaa aaagagttgg tagctcttga tccggcaaac aaaccaccgc tggtagcggt       720
ggtttttttg tttgcaagca gcagattacg cgcagaaaaa aaggatctca agaagatcct       780
ttgatctttt ctacggggtc tgacgctcag tggaacgaaa actcacgtta agggattttg       840
gtcatgagat tatcaaaaag gatcttcacc tagatccttt taaattaaaa atgaagtttt       900
aaatcaatct aaagtatata tgagtaaact tggtctgaca gttaccaatg cttaatcagt       960
gaggcaccta tctcagcgat ctgtctattt cgttcatcca tagttgcctg actccccgtc      1020
gtgtagataa ctacgatacg ggagggctta ccatctggcc ccagtgctgc aatgataccg      1080
cgagacccac gctcaccggc tccagattta tcagcaataa accagccagc cggaagggcc      1140
gagcgcagaa gtggtcctgc aactttatcc gcctccatcc agtctattaa ttgttgccgg      1200
gaagctagag taagtagttc gccagttaat agtttgcgca acgttgttgc cattgctaca      1260
ggcatcgtgg tgtcacgctc gtcgtttggt atggcttcat tcagctccgg ttcccaacga      1320
tcaaggcgag ttacatgatc ccccatgttg tgcaaaaaag cggttagctc cttcggtcct      1380
ccgatcgttg tcagaagtaa gttggccgca gtgttatcac tcatggttat ggcagcactg      1440
cataattctc ttactgtcat gccatccgta agatgctttt ctgtgactgg tgagtactca      1500
accaagtcat tctgagaata gtgtatgcgg cgaccgagtt gctcttgccc ggcgtcaata      1560
cgggataata ccgcgccaca tagcagaact ttaaaagtgc tcatcattgg aaaacgttct      1620
tcggggcgaa aactctcaag gatcttaccg ctgttgagat ccagttcgat gtaacccact      1680
cgtgcaccca actgatcttc agcatctttt actttcacca gcgtttctgg gtgagcaaaa      1740
acaggaaggc aaaatgccgc aaaaaaggga ataagggcga cacggaaatg ttgaatactc      1800
atactcttcc tttttcaata ttattgaagc atttatcagg gttattgtct catgagcgga      1860
tacatatttg aatgtattta gaaaaataaa caaatagggg ttccgcgcac atttccccga      1920
aaagtgccac ctgacgtcta agaaaccatt attatcatga cattaaccta taaaaatagg      1980
cgtatcacga ggccctttcg tctcgcgcgt ttcggtgatg acggtgaaaa cctctgacac      2040
atgcagctcc cggagacggt cacagcttgt ctgtaagcgg atgccgggag cagacaagcc      2100
cgtcagggcg cgtcagcggg tgttggcggg tgtcggggct ggcttaacta tgcggcatca      2160
gagcagattg tactgagagt gcaccataaa attgtaaacg ttaatatttt gttaaaattc      2220
gcgttaaatt tttgttaaat cagctcattt tttaaccaat aggccgaaat cggcaaaatc      2280
ccttataaat caaaagaata gcccgagata gggttgagtg ttgttccagt ttggaacaag      2340
agtccactat taaagaacgt ggactccaac gtcaaagggc gaaaaaccgt ctatcagggc      2400
```

-continued

```
gatggcccac tacgtgaacc atcacccaaa tcaagttttt tggggtcgag gtgccgtaaa   2460
gcactaaatc ggaaccctaa agggagcccc cgatttagag cttgacgggg aaagccggcg   2520
aacgtggcga gaaaggaagg gaagaaagcg aaaggagcgg gcgctagggc gctggcaagt   2580
gtagcggtca cgctgcgcgt aaccaccaca cccgccgcgc ttaatgcgcc gctacagggc   2640
gcgtactatg gttgctttga cgtatgcggt gtgaaatacc gcacagatgc gtaaggagaa   2700
aataccgcat caggcgccat tcgccattca ggctgcgcaa ctgttgggaa gggcgatcgg   2760
tgcgggcctc ttcgctatta cgccagctgg cgaagggggg atgtgctgca aggcgattaa   2820
gttgggtaac gccagggttt tcccagtcac gacgttgtaa aacgacggcc agtgccaagc   2880
ttaccaaaca gagaatccgt gagttacgat aaaaggcgaa ggagcaattg aagtcgcacg   2940
ggtagaaggt gtgaatctcg agtgcgagcc cgaagcacaa actcgagaaa gccttctgcc   3000
aacatgtctt ccgtatttga tgagtacgaa cagctcctcg cggctcagac tcgccccaat   3060
ggagctcatg gagggggaga aaaagggagt accttaaaag tagacgtccc ggtattcact   3120
cttaacagtg atgacccaga agatagatgg agctttgtgg tattctgcct ccggattgct   3180
gttagcgaag atgccaacaa accactcagg caaggtgctc tcatatctct tttatgctcc   3240
cactcacagg taatgaggaa ccatgttgcc cttgcaggga aacagaatga agccacattg   3300
gccgtgcttg agattgatgg ctttgccaac ggcacgcccc agttcaacaa taggagtgga   3360
gtgtctgaag agagagcaca gagatttgcg atgatagcag gatctctccc tcgggcatgc   3420
agcaacggaa ccccgttcgt cacagccggg gccgaagatg atgcaccaga agacatcacc   3480
gataccctgg agaggatcct ctctatccag gctcaagtat gggtcacagt agcaaaagcc   3540
atgactgcgt atgagactgc agatgagtcg gaaacaaggc gaatcaataa gtatatgcag   3600
caaggcaggg tccaaaagaa atacatcctc taccccgtat gcaggagcac aatccaactc   3660
acgatcagac agtctcttgc agtccgcatc tttttggtta gcgagctcaa gagaggccgc   3720
aacacggcag gtggtacctc tacttattat aacctggtag gggacgtaga ctcatacatc   3780
aggaataccg ggcttactgc attcttcttg acactcaagt acggaatcaa caccaagaca   3840
tcagcccttg cacttagtag cctctcaggc gacatccaga agatgaagca gctcatgcgt   3900
ttgtatcgga tgaaaggaga taatgcgccg tacatgacat tacttggtga tagtgaccag   3960
atgagctttg cgcctgccga gtatgcacaa ctttactcct ttgccatggg tatggcatca   4020
gtcctagata aaggtactgg gaaataccaa tttgccaggg actttatgag cacatcattc   4080
tggagacttg gagtagagta cgctcaggct cagggaagta gcattaacga ggatatggct   4140
gccgagctaa agctaacccc agcagcaagg aggggcctgg cagctgctgc ccaacgggtc   4200
tccgaggaga ccagcagcat agacatgcct actcaacaag tcggagtcct cactgggctt   4260
agcgaggggg ggtcccaagc tctacaaggc ggatcgaata gatcgcaagg gcaaccagaa   4320 gccgggatg gggagaccca attcctggat ctgatgagag cggtagcaaa tagcatgagg   4380
gaggcgccaa actctgcaca gggcactccc caatcggggc ctcccccaac tcctgggcca   4440
tcccaagata cgacaccga ctgggggtat tgatggacaa aacccagcct gcttccacaa    4500
aaacatccca atgccctcac ccgtagtcga ccctcgatt tgcggctcta tatgaccaca    4560
ccctcaaaca aacatccccc tctttcctcc ctcccctgc tgtacaacta cgtacgccct    4620
agataccaca ggcacaatgc ggctcactaa caatcaaaac agagccgagg gaattagaaa    4680
aaagtacggg tagaagaggg atattcagag atcagggcaa gtctcccgag tctctgctct    4740
```

```
ctcctctacc tgatagacca ggacaaacat ggccaccttt acagatgcag agatcgacga    4800
gctatttgag acaagtggaa ctgtcattga caacataatt acagcccagg gtaaaccagc    4860
agagactgtt ggaaggagtg caatcccaca aggcaagacc aaggtgctga gcgcagcatg    4920
ggagaagcat gggagcatcc agccaccggc cagtcaagac aaccccgatc gacaggacag    4980
atctgacaaa caaccatcca cacccgagca aacgaccccg catgacagcc cgccggccac    5040
atccgccgac cagcccccca cccaggccac agacgaagcc gtcgacacac agctcaggac    5100
cggagcaagc aactctctgc tgttgatgct tgacaagctc agcaataaat cgtccaatgc    5160
taaaaagggc ccatggtcga gcccccaaga ggggaatcac caacgtccga ctcaacagca    5220
ggggagtcaa cccagtcgcg gaaacagtca ggaaagaccg cagaaccaag tcaaggccgc    5280
ccctggaaac cagggcacag acgtgaacac agcatatcat ggacaatggg aggagtcaca    5340
actatcagct ggtgcaaccc ctcatgctct ccgatcaagg cagagccaag acaatacct    5400 tgtatctgcg gatcatgtcc agccaccgt agactttgtg caagcgatga tgtctatgat    5460
ggaggcgata tcacagagag taagtaaggt tgactatcag ctagatcttg tcttgaaaca    5520
gacatcctcc atccctatga tgcggtccga aatccaacag ctgaaaacat ctgttgcagt    5580
catggaagcc aacttgggaa tgatgaagat tctggatccc ggttgtgcca acatttcatc    5640
tctgagtgat ctacgggcag ttgcccgatc tcacccggtt ttagtttcag gccctggaga    5700
cccctctccc tatgtgacac aaggaggcga aatggcactt aataaacttt cgcaaccagt    5760
gccacatcca tctgaattga ttaaacccgc cactgcatgc gggcctgata taggagtgga    5820
aaaggacact gtccgtgcat tgatcatgtc acgcccaatg cacccgagtt cttcagccaa    5880
gctcctaagc aagttagatg cagccgggtc gatcgaggaa atcaggaaaa tcaagcgcct    5940
tgctctaaat ggctaattac tactgccaca cgtagcgggt ccctgtccac tcggcatcac    6000
acggaatctg caccgagttc cccccgcgg acccaaggtc caactctcca agcggcaatc    6060
ctctctcgct tcctcagccc cactgaatga tcgcgtaacc gtaattaatc tagctacatt    6120
taagattaag aaaaaatacg ggtagaattg gagtgcccca attgtgccaa gatggactca    6180
tctaggacaa ttgggctgta ctttgattct gcccattctt ctagcaacct gttagcattt    6240
ccgatcgtcc tacaagacac aggagatggg aagaagcaaa tcgccccgca atataggatc    6300
cagcgccttg acttgtggac tgatagtaag gaggactcag tattcatcac cacctatgga    6360
ttcatctttc aagttgggaa tgaagaagcc accgtcggca tgatcgatga taaacccaag    6420
cgcgagttac tttccgctgc gatgctctgc ctaggaagcg tcccaaatac cggagacctt    6480
attgagctgg caagggcctg tctcactatg atagtcacat gcaagaagag tgcaactaat    6540
actgagagaa tggtttttctc agtagtgcag gcaccccaag tgctgcaaag ctgtagggtt    6600
gtggcaaaca atactcatc agtgaatgca gtcaagcacg tgaaagcgcc agagaagatt    6660
cccgggagtg aaccctaga atacaaggtg aactttgtct ccttgactgt ggtaccgaag    6720
agggatgtct acaagatccc agctgcagta ttgaaggttt ctggctcgag tctgtacaat    6780
cttgcgctca atgtcactat taatgtggag gtagacccga ggagtccttt ggttaaatct    6840
ctgtctaagt ctgacagcgg atactatgct aacctcttct tgcatattgg acttatgacc    6900
actgtagata ggaaggggaa gaaagtgaca tttgacaagc tggaaaagaa aataaggagc    6960
cttgatctat ctgtcgggct cagtgatgtg ctcgggcctt ccgtgttggt aaaagcaaga    7020
ggtgcacgga ctaagctttt ggcaccttc ttctctagca gtgggacagc ctgctatccc    7080
atagcaaatg cttctcctca ggtggccaag atactctgga gtcaaaccgc gtgcctgcgg    7140
```

```
agcgttaaaa tcattatcca agcaggtacc caacgcgctg tcgcagtgac cgccgaccac    7200
gaggttacct ctactaagct ggagaagggg cacacccttg ccaaatacaa tccttttaag    7260
aaataagctg cgtctctgag attgcgctcc gcccactcac ccagatcatc atgacacaaa    7320
aaactaatct gtcttgatta tttacagtta gtttacctgt ctatcaagtt agaaaaaaca    7380
cgggtagaag attctggatc ccggttggcg ccctccaggt gcaagatggg ctccagacct    7440
tctaccaaga acccagcacc tatgatgctg actatccggg ttgcgctggt actgagttgc    7500
atctgtccgg caaactccat tgatggcagg cctcttgcag ctgcaggaat tgtggttaca    7560
ggagacaaag ccgtcaacat atacacctca tcccagacag gatcaatcat agttaagctc    7620
ctcccgaatc tgcccaagga taaggaggca tgtgcgaaag ccccttgga tgcatacaac    7680 aggacattga ccactttgct cacccccctt ggtgactcta tccgtaggat acaagagtct    7740
gtgactacat ctggagggcg gagacagagg cgctttatag gcgccattat tggcggtgtg    7800
gctcttgggg ttgcaactgc cgcacaaata acagcggccg cagctctgat acaagccaaa    7860
caaaatgctg ccaacatcct ccgacttaaa gagagcattg ccgcaaccaa tgaggctgtg    7920
catgaggtca ctgacggatt atcgcaacta gcagtggcag ttgggaagat gcagcagttt    7980
gttaatgacc aatttaataa aacagctcag gaattagact gcatcaaaat tgcacagcaa    8040
gttggtgtag agctcaacct gtacctaacc gaattgacta cagtattcgg accacaaatc    8100
acttcacctg ctttaaacaa gctgactatt caggcacttt acaatctagc tggtggaaat    8160
atggattact tattgactaa gttaggtgta gggaacaatc aactcagctc attaatcggt    8220
agcggcttaa tcaccggtaa ccctattcta tacgactcac agactcaact cttgggtata    8280
caggtaactc taccttcagt cgggaaccta aataatatgc gtgccaccta cttggaaacc    8340
ttatccgtaa gcacaaccag gggatttgcc tcggcacttg tcccaaaagt ggtgacacag    8400
gtcggttctg tgatagaaga acttgacacc tcatactgta tagaaactga cttagattta    8460
tattgtacaa gaatagtaac gttccctatg tcccctggta tttattcctg cttgagcggc    8520
aatacgtcgg cctgtatgta ctcaaagacc gaaggcgcac ttactacacc atacatgact    8580
atcaaaggtt cagtcatcgc caactgcaag atgacaacat gtagatgtgt aaaccccccg    8640
ggtatcatat cgcaaaacta tggagaagcc gtgtctctaa tagataaaca atcatgcaat    8700
gttttatcct taggcgggat aacttttaagg ctcagtgggg aattcgatgt aacttatcag    8760
aagaatatct caatacaaga ttctcaagta ataataacag gcaatcttga tatctcaact    8820
gagcttggga atgtcaacaa ctcgatcagt aatgctttga ataagttaga ggaaagcaac    8880
agaaaactag acaaagtcaa tgtcaaactg actagcacat ctgctctcat tacctatatc    8940 gtttttgacta tcatatctct tgtttttggt atacttagcc tgattctagc atgctaccta    9000
atgtacaagc aaaaggcgca acaaaagacc ttattatggc ttgggaataa tactctagat    9060
cagatgagag ccactacaaa aatgtgaaca cagatgagga acgaaggttt ccctaatagt    9120
aatttgtgtg aaagttctgg tagtctgtca gttcagagag ttaagaaaaa actaccggtt    9180
gtagatgacc aaaggacgat atacgggtag aacggtaaga gaggccgccc ctcaattgcg    9240
agccaggctt cacaacctcc gttctaccgc ttcaccgaca acagtcctca atcatggacc    9300
gcgccgttag ccaagttgcg ttagagaatg atgaaagaga ggcaaaaaat acatggcgct    9360
tgatattccg gattgcaatc ttattcttaa cagtagtgac cttggctata tctgtagcct    9420
cccttttata tagcatgggg gctagcacac ctagcgatct tgtaggcata ccgactagga    9480
```

-continued

```
tttccagggc agaagaaaag attacatcta cacttggttc caatcaagat gtagtagata   9540
ggatatataa gcaagtggcc cttgagtctc cgttggcatt gttaaatact gagaccacaa   9600
ttatgaacgc aataacatct ctctcttatc agattaatgg agctgcaaac aacagtgggt   9660 gggggggcacc tatccatgac ccagattata taggggggat aggcaaagaa ctcattgtag   9720
atgatgctag tgatgtcaca tcattctatc cctctgcatt tcaagaacat ctgaatttta   9780
tcccggcgcc tactacagga tcaggttgca ctcgaatacc ctcatttgac atgagtgcta   9840
cccattactg ctacacccat aatgtaatat tgtctggatg cagagatcac tcacattcat   9900
atcagtattt agcacttggt gtgctccgga catctgcaac agggagggta ttcttttcta   9960
ctctgcgttc catcaacctg gacgacaccc aaaatcggaa gtcttgcagt gtgagtgcaa  10020
ctcccctggg ttgtgatatg ctgtgctcga aagtcacgga gacagaggaa gaagattata  10080
actcagctgt ccctacgcgg atggtacatg ggaggttagg gttcgacggc cagtaccacg  10140
aaaaggacct agatgtcaca acattattcg gggactgggt ggccaactac ccaggagtag  10200
ggggtggatc ttttattgac agccgcgtat ggttctcagt ctacgaggg ttaaaaccca  10260 attcacccag tgacactgta caggaaggga aatatgtgat atacaagcga tacaatgaca  10320
catgcccaga tgagcaagac taccagattc gaatggccaa gtcttcgtat aagcctggac  10380
ggtttggtgg aaacgcata cagcaggcta tcttatctat caaggtgtca acatccttag  10440
gcgaagaccc ggtactgact gtaccgccca acacagtcac actcatgggg gccgaaggca  10500
gaattctcac agtagggaca tctcatttct tgtatcaacg agggtcatca tacttctctc  10560
ccgcgttatt atatcctatg acagtcagca acaaaacagc cactcttcat agtccttata  10620
cattcaatgc cttcactcgg ccaggtagta tcccttgcca ggcttcagca agatgcccca  10680
actcgtgtgt tactggagtc tatacagatc catatcccct aatcttctat agaaaccaca  10740
ccttgcgagg ggtattcggg acaatgcttg atggtgtaca agcaagactt aaccctgcgt  10800
ctgcagtatt cgatagcaca tcccgcagtc gcattactcg agtgagttca agcagtacca  10860
aagcagcata cacaacatca acttgtttta aagtggtcaa gactaataag acctattgtc  10920
tcagcattgc tgaaatatct aatactctct cggagaatt cagaatcgtc ccgttactag  10980
ttgagatcct caaagatgac ggggttagag aagccaggtc tggctagttg agtcaattat  11040
aaaggagttg gaaagatggc attgtatcac ctatcttctg cgacatcaag aatcaaaccg  11100
aatgccggcg cgtgctcgaa ttccatgttg ccagttgacc acaatcagcc agtgctcatg  11160
cgatcagatt aagccttgtc aatagtctct tgattaagaa aaaatgtaag tggcaatgag  11220
atacaaggca aaacagctca tggttaacaa tacgggtagg acatggcgag ctccggtcct  11280
gaaagggcag agcatcagat tatcctacca gagtcacacc tgtcttcacc attggtcaag  11340
cacaaactac tctattactg gaaattaact gggctaccgc ttcctgatga atgtgacttc  11400
gaccacctca ttctcagccg acaatggaaa aaaatacttg aatcggcctc tcctgatact  11460
gagagaatga taaaactcgg aagggcagta caccaaactc ttaaccacaa ttccagaata  11520
accggagtgc tccaccccag gtgtttagaa gaactggcta atattgaggt cccagattca  11580
accaacaaat ttcggaagat tgagaagaag atccaaattc acaacacgag atatggagaa  11640
ctgttcacaa ggctgtgtac gcatatagag aagaaactgc tggggtcatc ttggtctaac  11700
aatgtccccc ggtcagagga gttcagcagc attcgtacgg atccggcatt ctggtttcac  11760
tcaaaatggt ccacagccaa gtttgcatgg ctccatataa aacagatcca gaggcatctg  11820
atggtggcag ctaggacaag gtctgcggcc aacaaattgg tgatgctaac ccataaggta  11880
```

-continued

```
ggccaagtct ttgtcactcc tgaacttgtc gttgtgacgc atacgaatga gaacaagttc   11940
acatgtctta cccaggaact tgtattgatg tatgcagata tgatggaggg cagagatatg   12000
gtcaacataa tatcaaccac ggcggtgcat ctcagaagct tatcagagaa aattgatgac   12060
attttgcggt taatagacgc tctggcaaaa gacttgggta tcaagtcta cgatgttgta   12120 tcactaatgg agggatttgc atacggagct gtccagctac tcgagccgtc aggtacattt   12180
gcaggagatt tcttcgcatt caacctgcag gagcttaaag acattctaat tggcctcctc   12240
cccaatgata tagcagaatc cgtgactcat gcaatcgcta ctgtattctc tggtttagaa   12300
cagaatcaag cagctgagat gttgtgtctg ttgcgtctgt ggggtcaccc actgcttgag   12360
tcccgtattg cagcaaaggc agtcaggagc caaatgtgcg caccgaaaat ggtagacttt   12420
gatatgatcc ttcaggtact gtctttcttc aagggaacaa tcatcaacgg gtacagaaag   12480
aagaatgcag gtgtgtggcc gcgagtcaaa gtggatacaa tatatgggaa ggtcattggg   12540
caactacatg cagattcagc agagatttca cacgatatca tgttgagaga gtataagagt   12600
ttatctgcac ttgaatttga gccatgtata gaatatgacc ctgtcaccaa cctgagcatg   12660
ttcctaaaag acaaggcaat cgcacacccc aacgataatt ggcttgcctc gtttaggcgg   12720
aaccttctct ccgaagacca gaagaaacat gtaaaagaag caacttcgac taatcgcctc   12780
ttgatagagt ttttagagtc aaatgatttt gatccatata aagagatgga atatctgacg   12840
acccttgagt accttagaga tgacaatgtg gcagtatcat actcgctcaa ggagaaggaa   12900
gtgaaagtta atggacggat cttcgctaag ctgacaaaga agttaaggaa ctgtcaggtg   12960
atggcggaag ggatcctagc cgatcagatt gcacctttct ttcagggaaa tggagtcatt   13020
caggatagca tatccttgac caagagtatg ctagcgatga gtcaactgtc ttttaacagc   13080
aataagaaac gtatcactga ctgtaaagaa agagtatctt caaaccgcaa tcatgatccg   13140
aaaagcaaga accgtcggag agttgcaacc ttcataacaa ctgacctgca aaagtactgt   13200
cttaattgga gatatcagac aatcaaattg ttcgctcatg ccatcaatca gttgatgggc   13260
ctacctcact tcttcgaatg gattcaccta agactgatgg acactacgat gttcgtagga   13320
gaccctttca atcctccaag tgaccctact gactgtgacc tctcaagagt ccctaatgat   13380
gacatatata ttgtcagtgc cagaggggggt atcgaaggat tatgccagaa gctatggaca   13440
atgatctcaa ttgctgcaat ccaacttgct gcagctagat cgcattgtcg tgttgcctgt   13500
atggtacagg gtgataatca agtaatagca gtaacgagag aggtaagatc agacgactct   13560
ccggagatgg tgttgacaca gttgcatcaa gccagtgata atttcttcaa ggaattaatt   13620
catgtcaatc atttgattgg ccataatttg aaggatcgtg aaaccatcag gtcagacaca   13680 ttcttccatat acagcaaacg aatcttcaaa gatggagcaa tcctcagtca agtcctcaaa   13740
aattcatcta aattagtgct agtgtcaggt gatctcagtg aaaacaccgt aatgtcctgt   13800
gccaacattg cctctactgt agcacggcta tgcgagaacg ggcttcccaa agacttctgt   13860
tactatttaa actatataat gagttgtgtg cagacatact ttgactctga gttctccatc   13920
accaacaatt cgcaccccga tcttaatcag tcgtggattg aggacatctc ttttgtgcac   13980
tcatatgttc tgactcctgc ccaattaggg ggactgagta accttcaata ctcaaggctc   14040
tacactagaa atatcggtga cccgggggact actgcttttg cagagatcaa gcgactagaa   14100
gcagtgggat tactgagtcc taacattatg actaatatct taactaggcc gcctgggaat   14160
ggagattggg ccagtctgtg caacgaccca tactctttca attttgagac tgttgcaagc   14220
```

```
ccaaatattg ttcttaagaa acatacgcaa agagtcctat ttgaaacttg ttcaaatccc   14280
ttattgtctg gagtgcacac agaggataat gaggcagaag agaaggcatt ggctgaattc   14340
ttgcttaatc aagaggtgat tcatccccgc gttgcgcatg ccatcatgga ggcaagctct   14400
gtaggtagga gaaagcaaat tcaagggctt gttgacacaa caaacaccgt aattaagatt   14460
gcgcttacta ggaggccatt aggcatcaag aggctgatgc ggatagtcaa ttattctagc   14520
atgcatgcaa tgctgtttag agacgatgtt ttttcctcca gtagatccaa ccacccctta   14580
gtctcttcta atatgtgttc tctgacactg gcagactatg cacggaatag aagctggtca   14640
cctttgacgg gaggcaggaa aatactgggt gtatctaatc ctgatacgat agaactcgta   14700
gagggtgaga ttcttagtgt aagcggaggg tgtacaagat gtgacagcgg agatgaacaa   14760
tttacttggt tccatcttcc aagcaatata gaattgaccg atgacaccag caagaatcct   14820
ccgatgaggg taccatatct cgggtcaaag acacaggaga ggagagctgc ctcacttgca   14880
aaaatagctc atatgtcgcc acatgtaaag gctgccctaa gggcatcatc cgtgttgatc   14940
tgggcttatg gggataatga agtaaattgg actgctgctc ttacgattgc aaaatctcgg   15000
tgtaatgtaa acttagagta tcttcggtta ctgtcccctt tacccacggc tgggaatctt   15060
caacatagac tagatgatgg tataaactcag atgacattca cccctgcatc tctctacagg   15120
gtgtcacctt acattcacat atccaatgat tctcaaaggc tgttcactga agaaggagtc   15180
aaagagggga atgtggttta ccaacagatc atgctcttgg gtttatctct aatcgaatcg   15240
atctttccaa tgacaacaac caggacatat gatgagatca cactgcacct acatagtaaa   15300
tttagttgct gtatcagaga agcacctgtt gcggttcctt tcgagctact tggggtggta   15360
ccggaactga ggacagtgac ctcaaataag tttatgtatg atcctagccc tgtatcggag   15420
ggagactttg cgagacttga cttagctatc ttcaagagtt atgagcttaa tctggagtca   15480
tatcccacga tagagctaat gaacattctt tcaatatcca gcgggaagtt gattggccag   15540
tctgtggttt cttatgatga agataccctcc ataaagaatg acgccataat agtgtatgac   15600
aatacccgaa attggatcag tgaagctcag aattcagatg tggtccgcct atttgaatat   15660
gcagcacttg aagtgctcct cgactgttct taccaactct attacctgag agtaagaggc   15720
ctggacaata ttgtcttata tatgggtgat ttatacaaga atatgccagg aattctactt   15780
tccaacattg cagctacaat atctcatccc gtcattcatt caaggttaca tgcagtgggc   15840
ctggtcaacc atgacggatc acaccaactt gcagatacgg attttatcga aatgtctgca   15900
aaactattag tatcttgcac ccgacgtgtg atctccggct tatattcagg aaataagtat   15960
gatctgctgt tcccatctgt cttagatgat aacctgaatg agaagatgct tcagctgata   16020
tcccggttat gctgtctgta cacggtactc tttgctacaa caagagaaat cccgaaaata   16080
agaggcttaa ctgcagaaga gaaatgttca atactcactg agtatttact gtcggatgct   16140 gtgaaccat tacttagccc cgatcaagtg agctctatca tgtctcctaa cataattaca   16200
ttcccagcta atctgtacta catgtctcgg aagagcctca atttgatcag ggaaagggag   16260
gacagggata ctatcctggc gttgttgttc ccccaagagc cattattaga gttcccttct   16320
gtgcaagata ttggtgctcg agtgaaagat ccattcaccc gacaacctgc ggcatttttg   16380
caagagttag atttgagtgc tccagcaagg tatgacgcat tcacacttag tcagattcat   16440
cctgaactca catctccaaa tccggaggaa gactacttag tacgatactt gttcagaggg   16500
atagggactg catcttcctc ttggtataag gcatctcatc tcctttctgt acccgaggta   16560
agatgtgcaa gacacgggaa ctccttatac ttagctgaag ggagcggagc catcatgagt   16620
```

-continued

```
cttctcgaac tgcatgtacc acatgaaact atctattaca atacgctctt ttcaaatgag    16680 atgaacccc cgcaacgaca tttcgggccg accccaactc agtttttgaa ttcggttgtt    16740
tataggaatc tacaggcgga ggtaacatgc aaagatggat ttgtccaaga gttccgtcca    16800
ttatggagag aaaatacaga ggaaagcgac ctgacctcag ataaagtagt ggggtatatt    16860
acatctgcag tgccctacag atctgtatca ttgctgcatt gtgacattga aattcctcca    16920
gggtccaatc aaagcttact agatcaacta gctatcaatt tatctctgat tgccatgcat    16980
tctgtaaggg agggcggggt agtaatcatc aaagtgttgt atgcaatggg atactacttt    17040
catctactca tgaacttgtt tgctccgtgt tccacaaaag gatatattct ctctaatggt    17100
tatgcatgtc gaggagatat ggagtgttac ctggtatttg tcatgggtta cctgggcggg    17160
cctacatttg tacatgaggt ggtgaggatg gcgaaaactc tggtcagcg gcacggtacg    17220 cttttgtcta aatcagatga gatcacactg accaggttat tcacctcaca gcggcagcgt    17280
gtgacagaca tcctatccag tcctttacca agattaataa agtacttgag gaagaatatt    17340
gacactgcgc tgattgaagc cgggggacag cccgtccgtc cattctgtgc ggagagtctg    17400
gtgagcacgc tagcgaacat aactcagata acccagatca tcgctagtca cattgacaca    17460
gttatccggt ctgtgatata tatggaagct gagggtgatc tcgctgacac agtatttcta    17520
tttacccctt acaatctctc tactgacggg aaaaagagga catcacttaa acagtgcacg    17580
agacagatcc tagaggttac aatactaggt cttagagtcg aaaatctcaa taaaataggc    17640
gatataatca gcctagtgct taaaggcatg atctccatgg aggaccttat cccactaagg    17700
acatacttga agcatagtac ctgccctaaa tatttgaagg ctgtcctagg tattaccaaa    17760
ctcaaagaaa tgtttacaga cacttctgta ctgtacttga ctcgtgctca acaaaaattc    17820
tacatgaaaa ctataggcaa tgcagtcaaa ggatattaca gtaactgtga ctcttaacga    17880
aaatcacata ttaataggct ccttttttgg ccaattgtat tcttgttgat ttaatcatat    17940
tatgttagaa aaaagttgaa ccctgactcc ttaggactcg aattcgaact caaataaatg    18000
tcttaaaaaa aggttgcgca caattattct tgagtgtagt ctcgtcattc accaaatctt    18060
tgtttggtgc gcgcagatct gtcatgatga tcattgcaat tggatccata tatagggccc    18120
gggttataat tacctcaggt cgacgtccca tggccattcg aattcgtaat catggtcata    18180
gctgtttcct gtgtgaaatt gttatccgct cacaattcca cacaacatac gagccggaag    18240
cataaagtgt aaagcctggg gtgcctaatg agtgagctaa ctcacattaa ttgcgttgcg    18300
ctcactgccc gctttccagt cgggaaacct gtcgtgccag ctgcattaat gaatcggcca    18360
acgcgcgggg agaggcggtt tgcgtattgg gcgc                                18394
```

```
<210> SEQ ID NO 7
<211> LENGTH: 6
<212> TYPE: PRT
<213> ORGANISM: SARS-CoV2

<400> SEQUENCE: 7

Asn Phe Leu Pro Arg Pro
1               5

<210> SEQ ID NO 8
<211> LENGTH: 6
<212> TYPE: PRT
<213> ORGANISM: SARS-CoV2

<400> SEQUENCE: 8
```

-continued

```
Thr Phe Leu Ala Arg Gly
1               5

<210> SEQ ID NO 9
<211> LENGTH: 6
<212> TYPE: PRT
<213> ORGANISM: SARS-CoV2

<400> SEQUENCE: 9

Arg Pro Ser Lys Arg Pro
1               5

<210> SEQ ID NO 10
<211> LENGTH: 6
<212> TYPE: PRT
<213> ORGANISM: SARS-CoV2

<400> SEQUENCE: 10

Leu Phe Leu Pro Arg Val
1               5

<210> SEQ ID NO 11
<211> LENGTH: 1288
<212> TYPE: PRT
<213> ORGANISM: SARS-CoV-2

<400> SEQUENCE: 11

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
                20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240
```

-continued

```
Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
            275             280             285

Val Asp Cys Ala Leu Asp Pro Leu Ser Glu Thr Lys Cys Thr Leu Lys
    290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
                325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Ala Asp Tyr Ser Val Leu
            355             360             365

Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
                405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
            435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
                485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
            515             520             525

Lys Ser Thr Asn Leu Val Lys Asn Lys Cys Val Asn Phe Asn Phe Asn
    530             535             540

Gly Leu Thr Gly Thr Gly Val Leu Thr Glu Ser Asn Lys Lys Phe Leu
545             550             555             560

Pro Phe Gln Gln Phe Gly Arg Asp Ile Ala Asp Thr Thr Asp Ala Val
                565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
    610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
                645             650             655

Asn Asn Ser Tyr Glu Cys Asp Ile Pro Ile Gly Ala Gly Ile Cys Ala
```

-continued

```
              660              665              670
Ser Tyr Gln Thr Gln Thr Asn Ser Pro Gly Ser Ala Ser Ser Val Ala
        675              680              685

Ser Gln Ser Ile Ile Ala Tyr Thr Met Ser Leu Gly Ala Glu Asn Ser
        690              695              700

Val Ala Tyr Ser Asn Asn Ser Ile Ala Ile Pro Thr Asn Phe Thr Ile
705              710              715              720

Ser Val Thr Thr Glu Ile Leu Pro Val Ser Met Thr Lys Thr Ser Val
                725              730              735

Asp Cys Thr Met Tyr Ile Cys Gly Asp Ser Thr Glu Cys Ser Asn Leu
            740              745              750

Leu Leu Gln Tyr Gly Ser Phe Cys Thr Gln Leu Asn Arg Ala Leu Thr
        755              760              765

Gly Ile Ala Val Glu Gln Asp Lys Asn Thr Gln Glu Val Phe Ala Gln
        770              775              780

Val Lys Gln Ile Tyr Lys Thr Pro Pro Ile Lys Asp Phe Gly Gly Phe
785              790              795              800

Asn Phe Ser Gln Ile Leu Pro Asp Pro Ser Lys Pro Ser Lys Arg Ser
                805              810              815

Pro Ile Glu Asp Leu Leu Phe Asn Lys Val Thr Leu Ala Asp Ala Gly
            820              825              830

Phe Ile Lys Gln Tyr Gly Asp Cys Leu Gly Asp Ile Ala Ala Arg Asp
        835              840              845

Leu Ile Cys Ala Gln Lys Phe Asn Gly Leu Thr Val Leu Pro Pro Leu
    850              855              860

Leu Thr Asp Glu Met Ile Ala Gln Tyr Thr Ser Ala Leu Leu Ala Gly
865              870              875              880

Thr Ile Thr Ser Gly Trp Thr Phe Gly Ala Gly Pro Ala Leu Gln Ile
                885              890              895

Pro Phe Pro Met Gln Met Ala Tyr Arg Phe Asn Gly Ile Gly Val Thr
            900              905              910

Gln Asn Val Leu Tyr Glu Asn Gln Lys Leu Ile Ala Asn Gln Phe Asn
        915              920              925

Ser Ala Ile Gly Lys Ile Gln Asp Ser Leu Ser Ser Thr Pro Ser Ala
    930              935              940

Leu Gly Lys Leu Gln Asp Val Val Asn Gln Asn Ala Gln Ala Leu Asn
945              950              955              960

Thr Leu Val Lys Gln Leu Ser Ser Asn Phe Gly Ala Ile Ser Ser Val
                965              970              975

Leu Asn Asp Ile Leu Ser Arg Leu Asp Pro Pro Glu Ala Glu Val Gln
            980              985              990

Ile Asp Arg Leu Ile Thr Gly Arg  Leu Gln Ser Leu Gln  Thr Tyr Val
        995              1000              1005

Thr Gln  Gln Leu Ile Arg Ala  Ala Glu Ile Arg Ala  Ser Ala Asn
    1010              1015              1020

Leu Ala  Ala Thr Lys Met Ser  Glu Cys Val Leu Gly  Gln Ser Lys
    1025              1030              1035

Arg Val  Asp Phe Cys Gly Lys  Gly Tyr His Leu Met  Ser Phe Pro
    1040              1045              1050

Gln Ser  Ala Pro His Gly Val  Val Phe Leu His Val  Thr Tyr Val
    1055              1060              1065

Pro Ala  Gln Glu Lys Asn Phe  Thr Thr Ala Pro Ala  Ile Cys His
    1070              1075              1080
```

```
Asp Gly Lys Ala His Phe Pro  Arg Glu Gly Val Phe  Val Ser Asn
    1085              1090              1095

Gly Thr His Trp Phe Val Thr  Gln Arg Asn Phe Tyr  Glu Pro Gln
    1100              1105              1110

Ile Ile Thr Thr Asp Asn Thr  Phe Val Ser Gly Asn  Cys Asp Val
    1115              1120              1125

Val Ile Gly Ile Val Asn Asn  Thr Val Tyr Asp Pro  Leu Gln Pro
    1130              1135              1140

Glu Leu Asp Ser Phe Lys Glu  Glu Leu Asp Lys Tyr  Phe Lys Asn
    1145              1150              1155

His Thr Ser Pro Asp Val Asp  Leu Gly Asp Ile Ser  Gly Ile Asn
    1160              1165              1170

Ala Ser Val Val Asn Ile Gln  Lys Glu Ile Asp Arg  Leu Asn Glu
    1175              1180              1185

Val Ala Lys Asn Leu Asn Glu  Ser Leu Ile Asp Leu  Gln Glu Leu
    1190              1195              1200

Gly Lys Tyr Glu Gln Gly Ser  Gly Tyr Ile Pro Glu  Ala Pro Arg
    1205              1210              1215

Asp Gly Gln Ala Tyr Val Arg  Lys Asp Gly Glu Trp  Val Leu Leu
    1220              1225              1230

Ser Thr Phe Leu Gly Arg Ser  Leu Glu Val Leu Phe  Gln Gly Pro
    1235              1240              1245

Gly His His His His His His  His His Ser Ala Trp  Ser His Pro
    1250              1255              1260

Gln Phe Glu Lys Gly Gly Gly  Ser Gly Gly Gly Gly  Ser Gly Gly
    1265              1270              1275

Ser Ala Trp Ser His Pro Gln  Phe Glu Lys
    1280              1285
```

```
<210> SEQ ID NO 12
<211> LENGTH: 1288
<212> TYPE: PRT
<213> ORGANISM: SARS-CoV-2

<400> SEQUENCE: 12

Met Phe Val Phe Leu Val Leu  Leu Pro Leu Val Ser  Ser Gln Cys Val
1               5               10               15

Asn Leu Thr Thr Arg Thr Gln  Leu Pro Pro Ala Tyr  Thr Asn Ser Phe
            20              25              30

Thr Arg Gly Val Tyr Tyr Pro  Asp Lys Val Phe Arg  Ser Ser Val Leu
        35              40              45

His Ser Thr Gln Asp Leu Phe  Leu Pro Phe Phe Ser  Asn Val Thr Trp
    50              55              60

Phe His Ala Ile His Val Ser  Gly Thr Asn Gly Thr  Lys Arg Phe Asp
65              70              75              80

Asn Pro Val Leu Pro Phe Asn  Asp Gly Val Tyr Phe  Ala Ser Thr Glu
            85              90              95

Lys Ser Asn Ile Ile Arg Gly  Trp Ile Phe Gly Thr  Thr Leu Asp Ser
        100             105             110

Lys Thr Gln Ser Leu Leu Ile  Val Asn Asn Ala Thr  Asn Val Val Ile
        115             120             125

Lys Val Cys Glu Phe Gln Phe  Cys Asn Asp Pro Phe  Leu Gly Val Tyr
    130             135             140

Tyr His Lys Asn Asn Lys Ser  Trp Met Glu Ser Glu  Phe Arg Val Tyr
```

-continued

```
145              150              155              160

Ser Ser Ala Asn Asn Cys Thr Phe Glu Tyr Val Ser Gln Pro Phe Leu
             165              170              175

Met Asp Leu Glu Gly Lys Gln Gly Asn Phe Lys Asn Leu Arg Glu Phe
             180              185              190

Val Phe Lys Asn Ile Asp Gly Tyr Phe Lys Ile Tyr Ser Lys His Thr
             195              200              205

Pro Ile Asn Leu Val Arg Asp Leu Pro Gln Gly Phe Ser Ala Leu Glu
     210              215              220

Pro Leu Val Asp Leu Pro Ile Gly Ile Asn Ile Thr Arg Phe Gln Thr
225              230              235              240

Leu Leu Ala Leu His Arg Ser Tyr Leu Thr Pro Gly Asp Ser Ser Ser
             245              250              255

Gly Trp Thr Ala Gly Ala Ala Ala Tyr Tyr Val Gly Tyr Leu Gln Pro
             260              265              270

Arg Thr Phe Leu Leu Lys Tyr Asn Glu Asn Gly Thr Ile Thr Asp Ala
             275              280              285

Val Asp Cys Ala Leu Asp Pro Leu Ser Glu Thr Lys Cys Thr Leu Lys
     290              295              300

Ser Phe Thr Val Glu Lys Gly Ile Tyr Gln Thr Ser Asn Phe Arg Val
305              310              315              320

Gln Pro Thr Glu Ser Ile Val Arg Phe Pro Asn Ile Thr Asn Leu Cys
             325              330              335

Pro Phe Gly Glu Val Phe Asn Ala Thr Arg Phe Ala Ser Val Tyr Ala
             340              345              350

Trp Asn Arg Lys Arg Ile Ser Asn Cys Val Ala Asp Tyr Ser Val Leu
             355              360              365

Tyr Asn Ser Ala Ser Phe Ser Thr Phe Lys Cys Tyr Gly Val Ser Pro
     370              375              380

Thr Lys Leu Asn Asp Leu Cys Phe Thr Asn Val Tyr Ala Asp Ser Phe
385              390              395              400

Val Ile Arg Gly Asp Glu Val Arg Gln Ile Ala Pro Gly Gln Thr Gly
             405              410              415

Lys Ile Ala Asp Tyr Asn Tyr Lys Leu Pro Asp Asp Phe Thr Gly Cys
             420              425              430

Val Ile Ala Trp Asn Ser Asn Asn Leu Asp Ser Lys Val Gly Gly Asn
             435              440              445

Tyr Asn Tyr Leu Tyr Arg Leu Phe Arg Lys Ser Asn Leu Lys Pro Phe
     450              455              460

Glu Arg Asp Ile Ser Thr Glu Ile Tyr Gln Ala Gly Ser Thr Pro Cys
465              470              475              480

Asn Gly Val Glu Gly Phe Asn Cys Tyr Phe Pro Leu Gln Ser Tyr Gly
             485              490              495

Phe Gln Pro Thr Asn Gly Val Gly Tyr Gln Pro Tyr Arg Val Val Val
             500              505              510

Leu Ser Phe Glu Leu Leu His Ala Pro Ala Thr Val Cys Gly Pro Lys
             515              520              525

Lys Ser Thr Asn Leu Val Lys Asn Lys Cys Val Asn Phe Asn Phe Asn
     530              535              540

Gly Leu Thr Gly Thr Gly Val Leu Thr Glu Ser Asn Lys Lys Phe Leu
545              550              555              560

Pro Phe Gln Gln Phe Gly Arg Asp Ile Ala Asp Thr Thr Asp Ala Val
             565              570              575
```

-continued

```
Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
            610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gly Ser Ala Ser Ser Val Ala
            675                 680                 685

Ser Gln Ser Ile Ile Ala Tyr Thr Met Ser Leu Gly Ala Glu Asn Ser
            690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
            770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Pro Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
            850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Pro Ala Leu Gln Ile
                885                 890                 895

Pro Phe Pro Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Pro Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990
```

-continued

```
Ile Asp Arg Leu Ile Thr Gly Arg  Leu Gln Ser Leu Gln  Thr Tyr Val
        995                1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Gly Ser  Gly Tyr Ile Pro Glu  Ala Pro Arg
    1205                1210                1215

Asp Gly  Gln Ala Tyr Val Arg  Lys Asp Gly Glu Trp  Val Leu Leu
    1220                1225                1230

Ser Thr  Phe Leu Gly Arg Ser  Leu Glu Val Leu Phe  Gln Gly Pro
    1235                1240                1245

Gly His  His His His His His  His His Ser Ala Trp  Ser His Pro
    1250                1255                1260

Gln Phe  Glu Lys Gly Gly Gly  Ser Gly Gly Gly Gly  Ser Gly Gly
    1265                1270                1275

Ser Ala  Trp Ser His Pro Gln  Phe Glu Lys
    1280                1285
```

```
<210> SEQ ID NO 13
<211> LENGTH: 1288
<212> TYPE: PRT
<213> ORGANISM: SARS-CoV-2

<400> SEQUENCE: 13

Met Phe Val Phe Leu Val Leu Leu Pro Leu Val Ser Ser Gln Cys Val
1               5                  10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60
```

-continued

```
Phe His Ala Ile His Val Ser Gly Thr Asn Gly Thr Lys Arg Phe Asp
65              70              75              80

Asn Pro Val Leu Pro Phe Asn Asp Gly Val Tyr Phe Ala Ser Thr Glu
                85              90              95

Lys Ser Asn Ile Ile Arg Gly Trp Ile Phe Gly Thr Thr Leu Asp Ser
        100             105             110

Lys Thr Gln Ser Leu Leu Ile Val Asn Asn Ala Thr Asn Val Val Ile
        115             120             125

Lys Val Cys Glu Phe Gln Phe Cys Asn Asp Pro Phe Leu Gly Val Tyr
    130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
                165             170             175

Met Asp Leu Glu Gly Lys Gln Gly Asn Phe Lys Asn Leu Arg Glu Phe
        180             185             190

Val Phe Lys Asn Ile Asp Gly Tyr Phe Lys Ile Tyr Ser Lys His Thr
        195             200             205

Pro Ile Asn Leu Val Arg Asp Leu Pro Gln Gly Phe Ser Ala Leu Glu
        210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
        275             280             285

Val Asp Cys Ala Leu Asp Pro Leu Ser Glu Thr Lys Cys Thr Leu Lys
    290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
            325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Ala Asp Tyr Ser Val Leu
        355             360             365

Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
        420             425             430

Val Ile Ala Trp Asn Ser Asn Asn Leu Asp Ser Lys Val Gly Gly Asn
        435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480
```

-continued

```
Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
            515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
    545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
    625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gly Ser Ala Ser Ser Val Ala
            675                 680                 685

Ser Gln Ser Ile Ile Ala Tyr Thr Met Ser Leu Gly Ala Glu Asn Ser
        690                 695                 700

Val Ala Tyr Ser Asn Asn Ser Ile Ala Ile Pro Thr Asn Phe Thr Ile
    705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
    785                 790                 795                 800

Asn Phe Ser Gln Ile Leu Pro Asp Pro Ser Lys Pro Ser Lys Arg Ser
                805                 810                 815

Pro Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
            835                 840                 845

Leu Ile Cys Ala Gln Lys Phe Asn Gly Leu Thr Val Leu Pro Pro Leu
        850                 855                 860

Leu Thr Asp Glu Met Ile Ala Gln Tyr Thr Ser Ala Leu Leu Ala Gly
    865                 870                 875                 880

Thr Ile Thr Ser Gly Trp Thr Phe Gly Ala Gly Pro Ala Leu Gln Ile
                885                 890                 895

Pro Phe Pro Met Gln Met Ala Tyr Arg Phe Asn Gly Ile Gly Val Thr
```

-continued

```
                    900             905             910
Gln Asn Val Leu Tyr Glu Asn Gln Lys Leu Ile Ala Asn Gln Phe Asn
                915             920             925
Ser Ala Ile Gly Lys Ile Gln Asp Ser Leu Ser Ser Thr Pro Ser Ala
            930             935             940
Leu Gly Lys Leu Gln Asp Val Val Asn Gln Asn Ala Gln Ala Leu Asn
945             950             955             960
Thr Leu Val Lys Gln Leu Ser Ser Asn Phe Gly Ala Ile Ser Ser Val
                965             970             975
Leu Asn Asp Ile Leu Ser Arg Leu Asp Pro Pro Glu Ala Glu Val Gln
            980             985             990
Ile Asp Arg Leu Ile Thr Gly Arg  Leu Gln Ser Leu Gln  Thr Tyr Val
            995             1000            1005
Thr Gln  Gln Leu Ile Arg Ala  Ala Glu Ile Arg Ala  Ser Ala Asn
    1010            1015            1020
Leu Ala  Ala Thr Lys Met Ser  Glu Cys Val Leu Gly  Gln Ser Lys
    1025            1030            1035
Arg Val  Asp Phe Cys Gly Lys  Gly Tyr His Leu Met  Ser Phe Pro
    1040            1045            1050
Gln Ser  Ala Pro His Gly Val  Val Phe Leu His Val  Thr Tyr Val
    1055            1060            1065
Pro Ala  Gln Glu Lys Asn Phe  Thr Thr Ala Pro Ala  Ile Cys His
    1070            1075            1080
Asp Gly  Lys Ala His Phe Pro  Arg Glu Gly Val Phe  Val Ser Asn
    1085            1090            1095
Gly Thr  His Trp Phe Val Thr  Gln Arg Asn Phe Tyr  Glu Pro Gln
    1100            1105            1110
Ile Ile  Thr Thr Asp Asn Thr  Phe Val Ser Gly Asn  Cys Asp Val
    1115            1120            1125
Val Ile  Gly Ile Val Asn Asn  Thr Val Tyr Asp Pro  Leu Gln Pro
    1130            1135            1140
Glu Leu  Asp Ser Phe Lys Glu  Glu Leu Asp Lys Tyr  Phe Lys Asn
    1145            1150            1155
His Thr  Ser Pro Asp Val Asp  Leu Gly Asp Ile Ser  Gly Ile Asn
    1160            1165            1170
Ala Ser  Val Val Asn Ile Gln  Lys Glu Ile Asp Arg  Leu Asn Glu
    1175            1180            1185
Val Ala  Lys Asn Leu Asn Glu  Ser Leu Ile Asp Leu  Gln Glu Leu
    1190            1195            1200
Gly Lys  Tyr Glu Gln Gly Ser  Gly Tyr Ile Pro Glu  Ala Pro Arg
    1205            1210            1215
Asp Gly  Gln Ala Tyr Val Arg  Lys Asp Gly Glu Trp  Val Leu Leu
    1220            1225            1230
Ser Thr  Phe Leu Gly Arg Ser  Leu Glu Val Leu Phe  Gln Gly Pro
    1235            1240            1245
Gly His  His His His His His  His His Ser Ala Trp  Ser His Pro
    1250            1255            1260
Gln Phe  Glu Lys Gly Gly Gly  Ser Gly Gly Gly Gly  Ser Gly Gly
    1265            1270            1275
Ser Ala  Trp Ser His Pro Gln  Phe Glu Lys
    1280            1285
```

<210> SEQ ID NO 14

<211> LENGTH: 18394
<212> TYPE: DNA
<213> ORGANISM: NDV LaSota

<400> SEQUENCE: 14

```
tcttccgctt cctcgctcac tgactcgctg cgctcggtcg ttcggctgcg gcgagcggta      60
tcagctcact caaaggcggt aatacggtta tccacagaat caggggataa cgcaggaaag     120
aacatgtgag caaaaggcca gcaaaaggcc aggaaccgta aaaaggccgc gttgctggcg     180 ttttccata ggctccgccc ccctgacgag catcacaaaa atcgacgctc aagtcagagg     240
tggcgaaacc cgacaggact ataaagatac caggcgtttc ccctggaag ctccctcgtg     300 cgctctcctg ttccgacct gccgcttacc ggatacctgt ccgcctttct cccttcggga     360
agcgtggcgc tttctcatag ctcacgctgt aggtatctca gttcggtgta ggtcgttcgc     420
tccaagctgg gctgtgtgca cgaaccccccc gttcagcccg accgctgcgc cttatccggt     480
aactatcgtc ttgagtccaa cccggtaaga cacgacttat cgccactggc agcagccact     540
ggtaacagga ttagcagagc gaggtatgta ggcggtgcta cagagttctt gaagtggtgg     600
cctaactacg gctacactag aagaacagta tttggtatct gcgctctgct gaagccagtt     660
accttcggaa aaagagttgg tagctcttga tccggcaaac aaaccaccgc tggtagcggt     720
ggtttttttg tttgcaagca gcagattacg cgcagaaaaa aaggatctca agaagatcct     780 ttgatcttt ctacggggtc tgacgctcag tggaacgaaa actcacgtta agggattttg     840
gtcatgagat tatcaaaaag gatcttcacc tagatccttt taaattaaaa atgaagtttt     900
aaatcaatct aaagtatata tgagtaaact tggtctgaca gttaccaatg cttaatcagt     960
gaggcaccta tctcagcgat ctgtctattt cgttcatcca tagttgcctg actccccgtc    1020
gtgtagataa ctacgatacg ggagggctta ccatctggcc ccagtgctgc aatgataccg    1080
cgagacccac gctcaccggc tccagattta tcagcaataa accagccagc cggaagggcc    1140
gagcgcagaa gtggtcctgc aactttatcc gcctccatcc agtctattaa ttgttgccgg    1200
gaagctagag taagtagttc gccagttaat agtttgcgca acgttgttgc cattgctaca    1260
ggcatcgtgg tgtcacgctc gtcgtttggt atggcttcat tcagctccgg ttcccaacga    1320
tcaaggcgag ttacatgatc ccccatgttg tgcaaaaaag cggttagctc cttcggtcct    1380
ccgatcgttg tcagaagtaa gttggccgca gtgttatcac tcatggttat ggcagcactg    1440
cataattctc ttactgtcat gccatccgta agatgctttt ctgtgactgg tgagtactca    1500
accaagtcat tctgagaata gtgtatgcgg cgaccgagtt gctcttgccc ggcgtcaata    1560
cgggataata ccgcgccaca tagcagaact ttaaaagtgc tcatcattgg aaaacgttct    1620
tcggggcgaa aactctcaag gatcttaccg ctgttgagat ccagttcgat gtaacccact    1680
cgtgcaccca actgatcttc agcatctttt actttcacca gcgtttctgg gtgagcaaaa    1740
acaggaaggc aaaatgccgc aaaaaaggga ataaggcga cacggaaatg ttgaatactc    1800
atactcttcc tttttcaata ttattgaagc atttatcagg gttattgtct catgagcgga    1860
tacatatttg aatgtattta gaaaaataaa caaatagggg ttccgcgcac atttccccga    1920
aaagtgccac ctgacgtcta agaaaccatt attatcatga cattaaccta taaaaatagg    1980
cgtatcacga ggccctttcg tctcgcgcgt ttcggtgatg acggtgaaaa cctctgacac    2040
atgcagctcc cggagacggt cacagcttgt ctgtaagcgg atgccgggag cagacaagcc    2100
cgtcagggcg cgtcagcggg tgttggcggg tgtcggggct ggcttaacta tgcggcatca    2160
gagcagattg tactgagagt gcaccataaa attgtaaacg ttaatatttt gttaaaattc    2220
```

-continued

```
gcgttaaatt tttgttaaat cagctcattt tttaaccaat aggccgaaat cggcaaaatc      2280
ccttataaat caaaagaata gcccgagata gggttgagtg ttgttccagt ttggaacaag      2340
agtccactat taaagaacgt ggactccaac gtcaaagggc gaaaaaccgt ctatcagggc      2400
gatggcccac tacgtgaacc atcacccaaa tcaagttttt tggggtcgag gtgccgtaaa      2460
gcactaaatc ggaaccctaa agggagcccc cgatttagag cttgacgggg aaagccggcg      2520
aacgtggcga gaaaggaagg gaagaaagcg aaaggagcgg gcgctagggc gctggcaagt      2580
gtagcggtca cgctgcgcgt aaccaccaca cccgccgcgc ttaatgcgcc gctacagggc      2640
gcgtactatg gttgctttga cgtatgcggt gtgaaatacc gcacagatgc gtaaggagaa      2700
aataccgcat caggcgccat tcgccattca ggctgcgcaa ctgttgggaa gggcgatcgg      2760
tgcgggcctc ttcgctatta cgccagctgg cgaaaggggg atgtgctgca aggcgattaa      2820
gttgggtaac gccagggttt tcccagtcac gacgttgtaa aacgacggcc agtgccaagc      2880
ttaccaaaca gagaatccgt gagttacgat aaaaggcgaa ggagcaattg aagtcgcacg      2940
ggtagaaggt gtgaatctcg agtgcgagcc cgaagcacaa actcgagaaa gccttctgcc      3000
aacatgtctt ccgtatttga tgagtacgaa cagctcctcg cggctcagac tcgccccaat      3060
ggagctcatg gaggggggaga aaaagggagt accttaaaag tagacgtccc ggtattcact      3120
cttaacagtg atgacccaga agatagatgg agctttgtgg tattctgcct ccggattgct      3180
gttagcgaag atgccaacaa accactcagg caaggtgctc tcatatctct tttatgctcc      3240
cactcacagg taatgaggaa ccatgttgcc cttgcaggga aacagaatga agccacattg      3300
gccgtgcttg agattgatgg ctttgccaac ggcacgcccc agttcaacaa taggagtgga      3360
gtgtctgaag agagagcaca gagatttgcg atgatagcag gatctctccc tcggcatgc       3420 agcaacggaa ccccgttcgt cacagccggg gccgaagatg atgcaccaga agacatcacc      3480
gataccctgg agaggatcct ctctatccag gctcaagtat gggtcacagt agcaaaagcc      3540
atgactgcgt atgagactgc agatgagtcg gaaacaaggc gaatcaataa gtatatgcag      3600
caaggcaggg tccaaaagaa atacatcctc taccccgtat gcaggagcac aatccaactc      3660
acgatcagac agtctcttgc agtccgcatc tttttggtta gcgagctcaa gagaggccgc      3720
aacacggcag gtggtacctc tacttattat aacctggtag gggacgtaga ctcatacatc      3780
aggaataccg ggcttactgc attcttcttg acactcaagt acggaatcaa caccaagaca      3840
tcagcccttg cacttagtag cctctcaggc gacatccaga agatgaagca gctcatgcgt      3900
ttgtatcgga tgaaaggaga taatgcgccg tacatgacat tacttggtga tagtgaccag      3960
atgagctttg cgcctgccga gtatgcacaa ctttactcct ttgccatggg tatggcatca      4020
gtcctagata aaggtactgg gaaataccaa tttgccaggg actttatgag cacatcattc      4080
tggagacttg gagtagagta cgctcaggct caggggaagta gcattaacga ggatatggct      4140
gccgagctaa agctaacccc agcagcaagg aggggcctgg cagctgctgc ccaacgggtc      4200
tccgaggaga ccagcagcat agacatgcct actcaacaag tcggagtcct cactgggctt      4260
agcgaggggg ggtcccaagc tctacaaggc ggatcgaata gatcgcaagg gcaaccagaa      4320 gccgggggatg gggagaccca attcctggat ctgatgagag cggtagcaaa tagcatgagg      4380
gaggcgccaa actctgcaca gggcactccc caatcggggc ctcccccaac tcctgggcca      4440
tcccaagata acgacaccga ctgggggtat tgatggacaa aacccagcct gcttccacaa      4500
aaacatccca atgccctcac ccgtagtcga cccctcgatt tgcggctcta tatgaccaca      4560
```

-continued

```
ccctcaaaca aacatccccc tctttcctcc ctccccctgc tgtacaacta cgtacgccct    4620
agataccaca ggcacaatgc ggctcactaa caatcaaaac agagccgagg gaattagaaa    4680
aaagtacggg tagaagaggg atattcagag atcagggcaa gtctcccgag tctctgctct    4740
ctcctctacc tgatagacca ggacaaacat ggccaccttt acagatgcag agatcgacga    4800
gctatttgag acaagtggaa ctgtcattga caacataatt acagcccagg gtaaaccagc    4860
agagactgtt ggaaggagtg caatcccaca aggcaagacc aaggtgctga gcgcagcatg    4920
ggagaagcat gggagcatcc agccaccggc cagtcaagac aaccccgatc gacaggacag    4980
atctgacaaa caaccatcca cacccgagca aacgaccccg catgacagcc cgccggccac    5040
atccgccgac cagcccccca cccaggccac agacgaagcc gtcgacacac agctcaggac    5100
cggagcaagc aactctctgc tgttgatgct tgacaagctc agcaataaat cgtccaatgc    5160
taaaaagggc ccatggtcga gcccccaaga ggggaatcac caacgtccga ctcaacagca    5220
ggggagtcaa cccagtcgcg gaaacagtca ggaaagaccg cagaaccaag tcaaggccgc    5280
ccctggaaac cagggcacag acgtgaacac agcatatcat ggacaatggg aggagtcaca    5340
actatcagct ggtgcaaccc ctcatgctct ccgatcaagg cagagccaag acaataccct    5400
tgtatctgcg gatcatgtcc agccacctgt agactttgtg caagcgatga tgtctatgat    5460
ggaggcgata tcacagagag taagtaaggt tgactatcag ctagatcttg tcttgaaaca    5520
gacatcctcc atccctatga tgcggtccga aatccaacag ctgaaaacat ctgttgcagt    5580
catggaagcc aacttgggaa tgatgaagat tctggatccc ggttgtgcca acatttcatc    5640
tctgagtgat ctacgggcag ttgcccgatc tcacccggtt ttagtttcag gccctggaga    5700
cccctctccc tatgtgacac aaggaggcga aatggcactt aataaacttt cgcaaccagt    5760
gccacatcca tctgaattga ttaaacccgc cactgcatgc gggcctgata taggagtgga    5820
aaaggacact gtccgtgcat tgatcatgtc acgcccaatg cacccgagtt cttcagccaa    5880
gctcctaagc aagttagatg cagccgggtc gatcgaggaa atcaggaaaa tcaagcgcct    5940
tgctctaaat ggctaattac tactgccaca cgtagcgggt ccctgtccac tcggcatcac    6000
acggaatctg caccgagttc cccccgcgg acccaaggtc caactctcca agcggcaatc    6060
ctctctcgct tcctcagccc cactgaatga tcgcgtaacc gtaattaatc tagctacatt    6120
taagattaag aaaaaatacg ggtagaattg gagtgcccca attgtgccaa gatggactca    6180
tctaggacaa ttgggctgta ctttgattct gcccattctt ctagcaacct gttagcattt    6240
ccgatcgtcc tacaagacac aggagatggg aagaagcaaa tcgccccgca atataggatc    6300
cagcgccttg acttgtggac tgatagtaag gaggactcag tattcatcac cacctatgga    6360
ttcatctttc aagttgggaa tgaagaagcc accgtcggca tgatcgatga taaacccaag    6420
cgcgagttac tttccgctgc gatgctctgc ctaggaagcg tcccaaatac cggagacctt    6480
attgagctgg caagggcctg tctcactatg atagtcacat gcaagaagag tgcaactaat    6540
actgagagaa tggtttttctc agtagtgcag gcaccccaag tgctgcaaag ctgtagggtt    6600
gtggcaaaca aatactcatc agtgaatgca gtcaagcacg tgaaagcgcc agagaagatt    6660
cccgggagtg gaaccctaga atacaaggtg aactttgtct ccttgactgt ggtaccgaag    6720
agggatgtct acaagatccc agctgcagta ttgaaggttt ctggctcgag tctgtacaat    6780
cttgcgctca atgtcactat taatgtggag gtagacccga ggagtccttt ggttaaatct    6840
ctgtctaagt ctgacagcgg atactatgct aacctcttct tgcatattgg acttatgacc    6900
actgtagata ggaaggggaa gaaagtgaca tttgacaagc tggaaaagaa aataaggagc    6960
```

-continued

```
cttgatctat ctgtcgggct cagtgatgtg ctcgggcctt ccgtgttggt aaaagcaaga    7020
ggtgcacgga ctaagctttt ggcacctttc ttctctagca gtgggacagc ctgctatccc    7080
atagcaaatg cttctcctca ggtggccaag atactctgga gtcaaaccgc gtgcctgcgg    7140
agcgttaaaa tcattatcca agcaggtacc caacgcgctg tcgcagtgac cgccgaccac    7200
gaggttacct ctactaagct ggagaagggg cacacccttg ccaaatacaa tccttttaag    7260
aaataagctg cgtctctgag attgcgctcc gcccactcac ccagatcatc atgacacaaa    7320
aaactaatct gtcttgatta tttacagtta gtttacctgt ctatcaagtt agaaaaaaca    7380
cgggtagaag attctggatc ccggttggcg ccctccaggt gcaagatggg ctccagacct    7440
tctaccaaga acccagcacc tatgatgctg actatccggg ttgcgctggt actgagttgc    7500
atctgtccgg caaactccat tgatggcagg cctcttgcag ctgcaggaat tgtggttaca    7560
ggagacaaag ccgtcaacat atacacctca tcccagacag gatcaatcat agttaagctc    7620
ctcccgaatc tgcccaagga taaggaggca tgtgcgaaag ccccccttgga tgcatacaac   7680 aggacattga ccactttgct cacccccctt ggtgactcta tccgtaggat acaagagtct    7740
gtgactacat ctggagggcg gagacagagg cgctttatag gcgccattat tggcggtgtg    7800
gctcttgggg ttgcaactgc cgcacaaata acagcggccg cagctctgat acaagccaaa    7860
caaaatgctg ccaacatcct ccgacttaaa gagagcattg ccgcaaccaa tgaggctgtg    7920
catgaggtca ctgacggatt atcgcaacta gcagtggcag ttgggaagat gcagcagttt    7980
gttaatgacc aatttaataa aacagctcag gaattagact gcatcaaaat tgcacagcaa    8040
gttggtgtag agctcaacct gtacctaacc gaattgacta cagtattcgg accacaaatc    8100
acttcacctg ctttaaacaa gctgactatt caggcacttt acaatctagc tggtggaaat    8160
atggattact tattgactaa gttaggtgta gggaacaatc aactcagctc attaatcggt    8220
agcggcttaa tcaccggtaa ccctattcta tacgactcac agactcaact cttgggtata    8280
caggtaactg ccccttcagt cgggaaccta aataatatgc gtgccaccta cttggaaacc    8340
ttatccgtaa gcacaaccag gggatttgcc tcggcacttg tcccaaaagt ggtgacacag    8400
gtcggttctg tgatagaaga acttgacacc tcatactgta tagaaactga cttagattta    8460
tattgtacaa gaatagtaac gttccctatg tccctggta tttattcctg cttgagcggc    8520
aatacgtcgg cctgtatgta ctcaaagacc gaaggcgcac ttactacacc atacatgact    8580
atcaaaggtt cagtcatcgc caactgcaag atgacaacat gtagatgtgt aaacccccg     8640 ggtatcatat cgcaaaacta tggagaagcc gtgtctctaa tagataaaca atcatgcaat    8700
gttttatcct taggcgggat aactttaagg ctcagtgggg aattcgatgt aacttatcag    8760
aagaatatct caatacaaga ttctcaagta ataataacag gcaatcttga tatctcaact    8820
gagcttggga atgtcaacaa ctcgatcagt aatgctttga taagttaga ggaaagcaac     8880 agaaaactag acaaagtcaa tgtcaaactg actagcacat ctgctctcat tacctatatc    8940
gttttgacta tcatatctct tgttttggt atacttagcc tgattctagc atgctaccta     9000
atgtacaagc aaaaggcgca acaaaagacc ttattatggc ttgggaataa tactctagat    9060
cagatgagag ccactacaaa aatgtgaaca cagatgagga acgaaggttt ccctaatagt    9120
aatttgtgtg aaagttctgg tagtctgtca gttcagagag ttaagaaaaa actaccggtt    9180
gtagatgacc aaaggacgat atacgggtag aacggtaaga gaggccgccc ctcaattgcg    9240
agccaggctt cacaacctcc gttctaccgc ttcaccgaca acagtcctca atcatggacc    9300
```

```
gcgccgttag ccaagttgcg ttagagaatg atgaaagaga ggcaaaaaat acatggcgct    9360
tgatattccg gattgcaatc ttattcttaa cagtagtgac cttggctata tctgtagcct    9420
cccttttata tagcatgggg gctagcacac ctagcgatct tgtaggcata ccgactagga    9480
tttccagggc agaagaaaag attacatcta cacttggttc caatcaagat gtagtagata    9540
ggatatataa gcaagtggcc cttgagtctc cgttggcatt gttaaatact gagaccacaa    9600
ttatgaacgc aataacatct ctctcttatc agattaatgg agctgcaaac aacagtgggt    9660 gggggcacc tatccatgac ccagattata taggggggat aggcaaagaa ctcattgtag    9720
atgatgctag tgatgtcaca tcattctatc cctctgcatt tcaagaacat ctgaatttta    9780
tcccggcgcc tactacagga tcaggttgca ctcgaatacc ctcatttgac atgagtgcta    9840
cccattactg ctacacccat aatgtaatat tgtctggatg cagagatcac tcacattcat    9900
atcagtattt agcacttggt gtgctccgga catctgcaac agggagggta ttctttttcta    9960 ctctgcgttc catcaacctg gacgacaccc aaaatcggaa gtcttgcagt gtgagtgcaa   10020
ctcccctggg ttgtgatatg ctgtgctcga aagtcacgga gacagaggaa gaagattata   10080
actcagctgt ccctacgcgg atggtacatg ggaggttagg gttcgacggc cagtaccacg   10140
aaaaggacct agatgtcaca acattattcg gggactgggt ggccaactac ccaggagtag   10200
ggggtggatc ttttattgac agccgcgtat ggttctcagt ctacggaggg ttaaaaccca   10260
attcacccag tgacactgta caggaaggga aatatgtgat atacaagcga tacaatgaca   10320
catgcccaga tgagcaagac taccagattc gaatggccaa gtcttcgtat aagcctggac   10380
ggtttggtgg gaaacgcata cagcaggcta tcttatctat caaggtgtca acatccttag   10440
gcgaagaccc ggtactgact gtaccgccca acacagtcac actcatgggg gccgaaggca   10500
gaattctcac agtagggaca tctcatttct tgtatcaacg agggtcatca tacttctctc   10560
ccgcgttatt atatcctatg acagtcagca acaaaacagc cactcttcat agtccttata   10620
cattcaatgc cttcactcgg ccaggtagta tcccttgcca ggcttcagca agatgcccca   10680
actcgtgtgt tactggagtc tatacagatc catatcccct aatcttctat agaaaccaca   10740
ccttgcgagg ggtattcggg acaatgcttg atggtgtaca agcaagactt aaccctgcgt   10800
ctgcagtatt cgatagcaca tcccgcagtc gcattactcg agtgagttca agcagtacca   10860
aagcagcata cacaacatca acttgtttta aagtggtcaa gactaataag acctattgtc   10920
tcagcattgc tgaaatatct aatactctct tcggagaatt cagaatcgtc ccgttactag   10980
ttgagatcct caaagatgac ggggttagag aagccaggtc tggctagttg agtcaattat   11040
aaaggagttg gaaagatggc attgtatcac ctatcttctg cgacatcaag aatcaaaccg   11100
aatgccggcg cgtgctcgaa ttccatgttg ccagttgacc acaatcagcc agtgctcatg   11160
cgatcagatt aagccttgtc aatagtctct tgattaagaa aaaatgtaag tggcaatgag   11220
atacaaggca aaacagctca tggttaacaa tacgggtagg acatggcgag ctccggtcct   11280
gaaagggcag agcatcagat tatcctacca gagtcacacc tgtcttcacc attggtcaag   11340
cacaaactac tctattactg gaaattaact gggctaccgc ttcctgatga atgtgacttc   11400
gaccacctca ttctcagccg acaatggaaa aaaatacttg aatcggcctc tcctgatact   11460
gagagaatga taaaactcgg aagggcagta caccaaactc ttaaccacaa ttccagaata   11520
accggagtgc tccaccccag gtgtttagaa gaactggcta atattgaggt cccagattca   11580
accaacaaat ttcggaagat tgagaagaag atccaaattc acaacacgag atatggagaa   11640
ctgttcacaa ggctgtgtac gcatatagag aagaaactgc tggggtcatc ttggtctaac   11700
```

-continued

```
aatgtccccc ggtcagagga gttcagcagc attcgtacgg atccggcatt ctggtttcac   11760
tcaaaatggt ccacagccaa gtttgcatgg ctccatataa aacagatcca gaggcatctg   11820
atggtggcag ctaggacaag gtctgcggcc aacaaattgg tgatgctaac ccataaggta   11880
ggccaagtct ttgtcactcc tgaacttgtc gttgtgacgc atacgaatga gaacaagttc   11940
acatgtctta cccaggaact tgtattgatg tatgcagata tgatggaggg cagagatatg   12000
gtcaacataa tatcaaccac ggcggtgcat ctcagaagct tatcagagaa aattgatgac   12060
attttgcggt taatagacgc tctggcaaaa gacttgggta atcaagtcta cgatgttgta   12120
tcactaatgg agggatttgc atacggagct gtccagctac tcgagccgtc aggtacattt   12180
gcaggagatt tcttcgcatt caacctgcag gagcttaaag acattctaat tggcctcctc   12240
cccaatgata tagcagaatc cgtgactcat gcaatcgcta ctgtattctc tggtttagaa   12300
cagaatcaag cagctgagat gttgtgtctg ttgcgtctgt ggggtcaccc actgcttgag   12360
tcccgtattg cagcaaaggc agtcaggagc caaatgtgcg caccgaaaat ggtagacttt   12420
gatatgatcc ttcaggtact gtctttcttc aagggaacaa tcatcaacgg gtacagaaag   12480
aagaatgcag gtgtgtggcc gcgagtcaaa gtggatacaa tatatgggaa ggtcattggg   12540
caactacatg cagattcagc agagatttca cacgatatca tgttgagaga gtataagagt   12600
ttatctgcac ttgaatttga gccatgtata gaatatgacc ctgtcaccaa cctgagcatg   12660
ttcctaaaag acaaggcaat cgcacacccc aacgataatt ggcttgcctc gtttaggcgg   12720
aaccttctct ccgaagacca gaagaaacat gtaaaagaag caacttcgac taatcgcctc   12780
ttgatagagt ttttagagtc aaatgatttt gatccatata aagagatgga atatctgacg   12840
acccttgagt accttagaga tgacaatgtg gcagtatcat actcgctcaa ggagaaggaa   12900
gtgaaagtta atggacggat cttcgctaag ctgacaaaga agttaaggaa ctgtcaggtg   12960
atggcggaag ggatcctagc cgatcagatt gcacctttct ttcagggaaa tggagtcatt   13020
caggatagca tatccttgac caagagtatg ctagcgatga gtcaactgtc ttttaacagc   13080
aataagaaac gtatcactga ctgtaaagaa agagtatctt caaaccgcaa tcatgatccg   13140
aaaagcaaga accgtcggag agttgcaacc ttcataacaa ctgacctgca aaagtactgt   13200
cttaattgga gatatcagac aatcaaattg ttcgctcatg ccatcaatca gttgatgggc   13260
ctacctcact tcttcgaatg gattcaccta agactgatgg acactacgat gttcgtagga   13320
gaccctttca atcctccaag tgaccctact gactgtgacc tctcaagagt ccctaatgat   13380
gacatatata ttgtcagtgc cagagggggt atcgaaggat tatgccagaa gctatggaca   13440
atgatctcaa ttgctgcaat ccaacttgct gcagctagat cgcattgtcg tgttgcctgt   13500
atggtacagt gtgataatca gtaaatagca gtaacgagag aggtaagatc agacgactct   13560
ccggagatgg tgttgacaca gttgcatcaa gccagtgata atttcttcaa ggaattaatt   13620
catgtcaatc atttgattgg ccataatttg aaggatcgtg aaaccatcag gtcagacaca   13680
ttcttcatat acagcaaacg aatcttcaaa gatggagcaa tcctcagtca agtcctcaaa   13740
aattcatcta aattagtgct agtgtcaggt gatctcagtg aaaacaccgt aatgtcctgt   13800
gccaacattg cctctactgt agcacggcta tgcgagaacg gcttcccaa agacttctgt   13860 tactatttaa actatataat gagttgtgtg cagacatact ttgactctga gttctccatc   13920
accaacaatt cgcaccccga tcttaatcag tcgtggattg aggacatctc ttttgtgcac   13980
tcatatgttc tgactcctgc ccaattaggg ggactgagta accttcaata ctcaaggctc   14040
```

```
tacactagaa atatcggtga cccgggggact actgcttttg cagagatcaa gcgactagaa   14100
gcagtgggat tactgagtcc taacattatg actaatatct taactaggcc gcctgggaat   14160
ggagattggg ccagtctgtg caacgaccca tactctttca attttgagac tgttgcaagc   14220
ccaaatattg ttcttaagaa acatacgcaa agagtcctat ttgaaacttg ttcaaatccc   14280
ttattgtctg gagtgcacac agaggataat gaggcagaag agaaggcatt ggctgaattc   14340
ttgcttaatc aagaggtgat tcatccccgc gttgcgcatg ccatcatgga ggcaagctct   14400
gtaggtagga gaaagcaaat tcaagggctt gttgacacaa caaacaccgt aattaagatt   14460
gcgcttacta ggaggccatt aggcatcaag aggctgatgc ggatagtcaa ttattctagc   14520
atgcatgcaa tgctgtttag agacgatgtt ttttcctcca gtagatccaa ccaccccctta   14580 gtctcttcta atatgtgttc tctgacactg gcagactatg cacggaatag aagctggtca   14640
cctttgacgg gaggcaggaa aatactgggt gtatctaatc ctgatacgat agaactcgta   14700
gagggtgaga ttcttagtgt aagcggaggg tgtacaagat gtgacagcgg agatgaacaa   14760
tttacttggt tccatcttcc aagcaatata gaattgaccg atgacaccag caagaatcct   14820
ccgatgaggg taccatatct cgggtcaaag acacaggaga ggagagctgc ctcacttgca   14880
aaaatagctc atatgtcgcc acatgtaaag gctgccctaa gggcatcatc cgtgttgatc   14940
tgggcttatg gggataatga agtaaattgg actgctgctc ttacgattgc aaaatctcgg   15000
tgtaatgtaa acttagagta tcttcggtta ctgtccccctt tacccacggc tgggaatctt   15060
caacatagac tagatgatgg tataactcag atgacattca cccctgcatc tctctacagg   15120
gtgtcacctt acattcacat atccaatgat tctcaaaggc tgttcactga agaaggagtc   15180
aaagagggga atgtggttta ccaacagatc atgctcttgg gtttatctct aatcgaatcg   15240
atctttccaa tgacaacaac caggacatat gatgagatca cactgcacct acatagtaaa   15300
tttagttgct gtatcagaga agcacctgtt gcggttcctt tcgagctact tggggtggta   15360
ccggaactga ggacagtgac ctcaaataag tttatgtatg atcctagccc tgtatcggag   15420
ggagactttg cgagacttga cttagctatc ttcaagagtt atgagcttaa tctggagtca   15480
tatcccacga tagagctaat gaacattctt tcaatatcca gcgggaagtt gattggccag   15540
tctgtggttt cttatgatga agatacctcc ataaagaatg acgccataat agtgtatgac   15600
aatacccgaa attggatcag tgaagctcag aattcagatg tggtccgcct atttgaatat   15660
gcagcacttg aagtgctcct cgactgttct taccaactct attacctgag agtaagaggc   15720
ctggacaata ttgtcttata tatgggtgat ttatacaaga atatgccagg aattctactt   15780
tccaacattg cagctacaat atctcatccc gtcattcatt caaggttaca tgcagtgggc   15840
ctggtcaacc atgacggatc acaccaactt gcagatacgg atttttatcga aatgtctgca   15900 aaactattag tatcttgcac ccgacgtgtg atctccggct tatattcagg aaataagtat   15960
gatctgctgt tccatctgt cttagatgat aacctgaatg agaagatgct tcagctgata   16020
tcccggttat gctgtctgta cacggtactc tttgctacaa caagagaaat cccgaaaata   16080
agaggcttaa ctgcagaaga gaaatgttca atactcactg agtatttact gtcggatgct   16140
gtgaaaccat tacttagccc cgatcaagtg agctctatca tgtctcctaa cataattaca   16200
ttcccagcta atctgtacta catgtctcgg aagagcctca atttgatcag ggaaagggag   16260 gacaggggata ctatcctggc gttgttgttc ccccaagagc cattattaga gttcccttct   16320
gtgcaagata ttggtgctcg agtgaaagat ccattcaccc gacaacctgc ggcattttttg   16380 caagagttag atttgagtgc tccagcaagg tatgacgcat tcacacttag tcagattcat   16440
```

-continued

```
cctgaactca catctccaaa tccggaggaa gactacttag tacgatactt gttcagaggg  16500
atagggactg catcttcctc ttggtataag gcatctcatc tcctttctgt acccgaggta  16560
agatgtgcaa gacacgggaa ctccttatac ttagctgaag ggagcggagc catcatgagt  16620
cttctcgaac tgcatgtacc acatgaaact atctattaca atacgctctt ttcaaatgag  16680
atgaaccccc cgcaacgaca tttcgggccg accccaactc agtttttgaa ttcggttgtt  16740
tataggaatc tacaggcgga ggtaacatgc aaagatggat ttgtccaaga gttccgtcca  16800
ttatggagag aaaatacaga ggaaagcgac ctgacctcag ataaagtagt ggggtatatt  16860
acatctgcag tgccctacag atctgtatca ttgctgcatt gtgacattga aattcctcca  16920
gggtccaatc aaagcttact agatcaacta gctatcaatt tatctctgat tgccatgcat  16980
tctgtaaggg agggcggggt agtaatcatc aaagtgttgt atgcaatggg atactacttt  17040
catctactca tgaacttgtt tgctccgtgt tccacaaaag gatatattct ctctaatggt  17100
tatgcatgtc gaggagatat ggagtgttac ctggtatttg tcatgggtta cctgggcggg  17160
cctacatttg tacatgaggt ggtgaggatg gcgaaaactc tggtgcagcg gcacggtacg  17220
cttttgtcta aatcagatga gatcacactg accaggttat tcacctcaca gcggcagcgt  17280
gtgacagaca tcctatccag tcctttacca agattaataa agtacttgag gaagaatatt  17340
gacactgcgc tgattgaagc cggggacag cccgtccgtc cattctgtgc ggagagtctg  17400
gtgagcacgc tagcgaacat aactcagata acccagatca tcgctagtca cattgacaca  17460
gttatccggt ctgtgatata tatggaagct gagggtgatc tcgctgacac agtatttcta  17520
tttacccctt acaatctctc tactgacggg aaaaagagga catcacttaa acagtgcacg  17580
agacagatcc tagaggttac aatactaggt cttagagtcg aaaatctcaa taaaataggc  17640
gatataatca gcctagtgct taaaggcatg atctccatgg aggaccttat cccactaagg  17700
acatacttga agcatagtac ctgccctaaa tatttgaagg ctgtcctagg tattaccaaa  17760
ctcaaagaaa tgtttacaga cacttctgta ctgtacttga ctcgtgctca acaaaaattc  17820
tacatgaaaa ctataggcaa tgcagtcaaa ggatattaca gtaactgtga ctcttaacga  17880
aaatcacata ttaataggct cctttttttgg ccaattgtat tcttgttgat ttaatcatat  17940
tatgttagaa aaaagttgaa ccctgactcc ttaggactcg aattcgaact caaataaatg  18000
tcttaaaaaa aggttgcgca caattattct tgagtgtagt ctcgtcattc accaaatctt  18060
tgtttggtgc gcgcagatct gtcatgatga tcattgcaat tggatccata tatagggccc  18120
gggttataat tacctcaggt cgacgtccca tggccattcg aattcgtaat catggtcata  18180
gctgtttcct gtgtgaaatt gttatccgct cacaattcca cacaacatac gagccggaag  18240
cataaagtgt aaagcctggg gtgcctaatg agtgagctaa ctcacattaa ttgcgttgcg  18300
ctcactgccc gctttccagt cgggaaacct gtcgtgccag ctgcattaat gaatcggcca  18360
acgcgcgggg agaggcggtt tgcgtattgg gcgc                              18394
```